(12) United States Patent
Kolczewski et al.

(10) Patent No.: US 8,183,380 B2
(45) Date of Patent: *May 22, 2012

(54) 2-AMINOQUINOLINES

(75) Inventors: Sabine Kolczewski, Loerrach (DE); Claus Riemer, Freiburg (DE); Olivier Roche, Folgensbourg (FR); Lucinda Steward, Basel (CH); Juergen Wichmann, Steinen (DE); Thomas Woltering, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 464 days.

This patent is subject to a terminal disclaimer.

(21) Appl. No.: 12/393,058

(22) Filed: Feb. 26, 2009

(65) Prior Publication Data

US 2009/0227570 A1 Sep. 10, 2009

(30) Foreign Application Priority Data

Mar. 5, 2008 (EP) .................................. 08152327

(51) Int. Cl.
*C07D 215/38* (2006.01)
(52) U.S. Cl. ................. 546/159; 546/163; 514/313
(58) Field of Classification Search .............. 546/159, 546/163; 514/313
See application file for complete search history.

(56) References Cited

U.S. PATENT DOCUMENTS

| | | |
|---|---|---|
| 2007/0299074 A1 | 12/2007 | Netz et al. |
| 2009/0088451 A1 * | 4/2009 | Kolczewski et al. ........... 514/313 |
| 2009/0227583 A1 * | 9/2009 | Kolczewski et al. ....... 514/235.2 |
| 2009/0233927 A1 * | 9/2009 | Kolczewski et al. ....... 514/235.2 |

FOREIGN PATENT DOCUMENTS

| | | |
|---|---|---|
| WO | WO 2003/045313 | 6/2003 |
| WO | WO 2004/096771 | 11/2004 |
| WO | WO 2005/082871 | 9/2005 |

OTHER PUBLICATIONS

Hoyer et al., Pharmacol. Rev. vol. 46, pp. 157-204 (1994).
Rees et al., FEBS Lett. vol. 355, pp. 242-246 (1994).
Francken et al., Eur. J. Pharmacol. vol. 361, pp. 299-309 (1998).
Noda et al., J. Neurochem. vol. 84, pp. 222-232 (2003).
Thomas, D. R., Pharmacol. Ther. vol. 111(3) pp. 707-714 (2006).
Doly et al., The Journal of Comparative Neurology vol. 476 pp. 316-329 (2004).
Dubertret et al., J. of Psychiatric Research vol. 35 pp. 371-376 (2004).
Garcia-Ladona et al., 36th Annual Meeting Soc. Neurosci. Oct. 14-18, Atlanta Abstract 33.1 (2006).
Drescher et al., 36th Annual Meeting Soc. Neurosci. Oct. 14-18, Atlanta Abstract 33.2 (2006).
Thomas, Neuropharmacology vol. 51(3) pp. 566-577 (2006).
Barnes et al., Neuropharmacology vol. 38 pp. 1083-1152 (1999).
Pasqualetti et al., Mol. Brain Res. vol. 56 pp. 1-8 (1998).
Wang et al., Neurosci. Lett. vol. 278 pp. 9-12 (2000).
Birkett et al., Neuroreport vol. 11 pp. 2017-2020 (2000).
Iwata et al., Mol. Psychiatry vol. 6 pp. 217-219 (2001).
Duncan et al., Brain Research vol. 869, pp. 178-185 (2000).
Sprouse et al., Synapse, vol. 54(2) pp. 111-118 (2004).

* cited by examiner

*Primary Examiner* — D M Seaman
(74) *Attorney, Agent, or Firm* — George W. Johnston; Patricia S. Rocha-Tramaloni; Kimberly J. Prior

(57) ABSTRACT

The present invention is concerned with 2-aminoquinoline derivatives of formula I

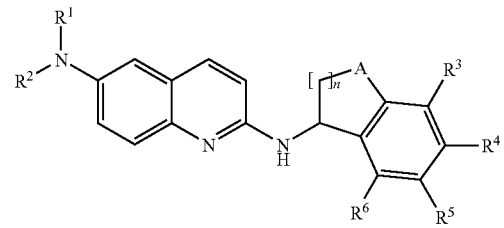

where $R^1$, $R^2$, $R^3$, $R^4$, $R^5$, $R^6$, A, and n are as defined in the specification and claims, their use 5-$HT_{5A}$ receptor antagonists, their manufacture, and pharmaceutical compositions containing them.

54 Claims, No Drawings

2-AMINOQUINOLINES

PRIORITY TO RELATED APPLICATION(S)

This application claims the benefit of European Patent Application No. 08152327.6, filed Mar. 5, 2008, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-$HT_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-$HT_{5A}$ serotonin receptor has been described in *FEBS Letters*, 355, 242-246 (1994). The sequence is not closely related to that of any previously known serotonin receptor, with the best homology being 35% to the human 5-$HT_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the 5-$HT_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The *Pharmacology & Therapeutics*, 111, 707-714 (2006) describes potential therapeutic utility of 5-$HT_{5A}$ receptor ligands for the treatment of circadian rhythm, sleep disturbances, mood disorders, schizophrenia, cognitive disorders and autism. The *Journal of Comparative Neurology*, 476, 316-329 (2004) suggests based on the localisation pattern of the 5-$HT_{5A}$ receptor in the rat spinal cord that 5-$HT_{5A}$ receptors may play a role in central motor control, nociception and autonomic function such as stress induced urinary incontinence and overactive bladder.

The *Journal of Psychiatric Research*, 38, 371-376 (2004) describes evidence for a potential significant role of the 5-$HT_{5A}$ gene in schizophrenia and more specifically in patients with later age at onset.

SUMMARY OF THE INVENTION

The present invention provides 2-aminoquinoline derivatives. In particular, the present invention provides compounds of formula (I)

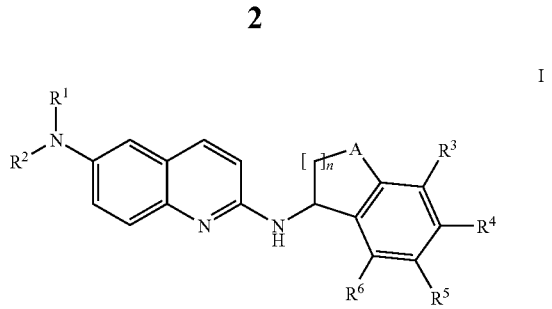

wherein
A is —$CH_2$— or —O—;
$R^1$ is hydrogen or alkyl;
$R^2$ is hydrogen,
  heterocycloalkyl,
  —$(CH_2)_a$—$R^a$, wherein $R^a$ is hydrogen, alkoxy, hydroxy, cyano, or $NR^iR^{ii}$, wherein $R^i$ and $R^{ii}$ are each independently hydrogen, alkyl or C(O)O-alkyl,
  allyl,
  —C(NH)—S—$R^b$, wherein $R^b$ is alkyl, cycloalkyl, haloalkyl, hydroxyalkyl, cyanoalkyl, or alkenyl,
  —C($NR^c$)$NR^dR^e$, wherein $R^c$, $R^d$, and $R^e$ are each independently hydrogen, alkyl, cycloalkyl, heterocycloalkyl, or wherein $R^d$ and $R^e$ together with the nitrogen to which they are bound form a heterocycloalkyl,
  —C(O)$R^f$, wherein $R^f$ is alkyl, —$(CH_2)_b$-cycloalkyl, —$(CH_2)_b$—Oalkyl, —$(CH_2)_b$-heterocycloalkyl, —O-heterocycloalkyl, or —$(CH_2)_b$—$NR^{iii}R^{iv}$,
    wherein $R^{iii}$ and $R^{iv}$ are each independently hydrogen, alkyl, —C(O)Oalkyl, —$(CH_2)_b$-cycloalkyl, —$(CH_2)_a$—Oalkyl, bicyclic cycloalkyl, bicyclic cycloalkenyl, —$(CH_2)_b$-heterocycloalkyl, —$(CH_2)_a$—O-heterocycloalkyl, or —$(CH_2)_a$—NR'R", wherein R' and R" are each independently hydrogen, alkyl or cycloalkyl,
  —C(S)$NR^vR^{vi}$, wherein $R^v$ and $R^{vi}$ are each independently H, alkyl or cycloalkyl,
  —S(O)$_2$$NR^{vii}R^{viii}$, wherein $R^{vii}$ and $R^{viii}$ are each independently H, alkyl, —C(O)Oalkyl, alkylene-O alkyl, cycloalkyl, or heterocycloalkyl,
  —S(O)$_2$-heterocycloalkyl, or
$R^1$ and $R^2$ together with the N atom to which they are bound form a 5- or 6-membered heterocycloalkyl,
$R^3$, $R^4$, $R^5$ and $R^6$ are each independently selected from the group consisting of H, halo, alkyl, haloalkyl, hydroxyalkyl, cyanoalkyl, alkoxy, haloalkoxy, —O-alkylene-O-alkyl, hydroxyl, oxo, cyano, nitro and $NR^{ix}R^x$, wherein $R^{ix}$ and $R^x$ are each independently H or alkyl;
a is 1 to 6;
b is 0 to 6; and
n is 1 or 2, and wherein
heterocycloalkyl is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy; and wherein
cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, AND alkyoxy;
or a pharmaceutically acceptable salt thereof.

The compounds of formula I can contain asymmetric carbon atoms. Accordingly, the present invention includes all stereoisomeric forms of the compounds of formula I, including each of the individual enantiomers and mixtures thereof, i.e. their individual optical isomers and mixtures thereof.

The present invention also includes pharmaceutical compositions containing a therapeutically effective amount of a compound of formula I or a pharmaceutically acceptable salt there of and a pharmaceutically acceptable carrier. The invention also provides methods for the manufacture of the compounds and compositions of the invention.

Compounds of formula I have good activity on the 5-HT$_{5A}$ receptor. Therefore, the invention provides methods for the treatment of depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, panic disorders, agoraphobia, social phobia, obsessive compulsive disorders, post-traumatic stress disorders), psychotic disorders (which includes schizophrenia, schizoaffective disorders, bipolar disease, mania, psychotic depression, and other psychoses involving paranoia and delusions), pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, nicotine, benzodiazepines, alcohol (ethanol), caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "allyl" denotes a group —CH$_2$CH═CH$_2$.

As used herein, the term "alkyl" denotes monovalent linear or branched saturated hydrocarbon moiety, consisting solely of carbon and hydrogen atoms, having from 1 to 7 carbon atoms, for example, methyl, ethyl, propyl, isopropyl, n-butyl, iso-butyl, sec-butyl, tert-butyl and the like. Preferred alkyl groups are groups with 1, 2, 3 or 4 carbon atoms.

As used herein, the term "alkylene" means a linear saturated divalent hydrocarbon radical of one to seven carbon atoms or a branched saturated divalent hydrocarbon radical of three to seven carbon atoms. Preferred are divalent hydrocarbon radicals of one to four carbon atoms.

The term "halo" denotes chloro, iodo, fluoro and bromo. Preferred halo are fluoro, chloro and bromo, more preferred are fluoro and chloro.

The term "haloalkyl" denotes an alkyl group as defined above wherein at least one of the hydrogen atoms of the alkyl group is replaced by a halogen atom, preferably fluoro or chloro, most preferably fluoro. Examples of haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred haloalkyl groups are monofluoro-, difluoro- or trifluoro-methyl, -ethyl or -propyl, for example 3,3,3-trifluoropropyl, 2-fluoroethyl, 2,2,2-trifluoroethyl, fluoromethyl, trifluoromethyl.

The term "hydroxyalkyl" denotes an alkyl group as defined above wherein at least one of the hydrogen atoms of the alkyl group is replaced by a hydroxy group. Examples of hydroxyalkyl include but are not limited to methyl, ethyl, propyl, isopropyl, isobutyl, sec-butyl, tert-butyl, pentyl or n-hexyl substituted by one or more OH, as well as those groups specifically illustrated by the examples herein below.

The term "cyanoyalkyl" denotes an alkyl group as defined above wherein at least one of the hydrogen atoms of the alkyl group is replaced by a cyano group. Examples of cyanoalkyl include but are not limited to methyl, ethyl, propyl, isopropyl, isobutyl, sec-butyl, tert-butyl, pentyl or n-hexyl substituted by one or more CN, as well as those groups specifically illustrated by the examples herein below.

The term "alkoxy" denotes a group —O—R' wherein R' is alkyl as defined above.

The term "aromatic" means the presence of an electron sextet in a ring, according to Hückel's rule.

The term "cycloalkyl" refers to a monovalent saturated monocyclic hydrocarbon radical of 3 to 7 ring carbon atoms, such as cyclopropyl, cyclobutanyl, cyclopentyl, cyclohexyl or cycloheptyl. Preferred are cyclopropyl, cyclopentyl and cyclohexyl. Cycloalkyl is optionally substituted as described herein.

The term "bicyclic cycloalkyl" denotes a monovalent saturated bicyclic hydrocarbon radical of 7 or 8 ring carbon atoms. Bicyclic means consisting of two saturated carbocycles having two carbon atoms in common, i.e. the bridge separating the two rings is either a single bond or a chain of preferably one or two carbon atoms. Examples for bicyclic cycloalkyl are bicyclo[2.2.1]heptanyl, and bicyclo[2.2.2]octanyl. Corresponding "bicyclic cycloalkenyl" preferably bear one double bond in their ring system, examples are bicyclo [2.2.1]heptenyl, and bicyclo[2.2.2]octenyl. Bicyclic cycloalkyl or cycloalkenyl is optionally substituted as described herein. Examples for substituents are independently selected from alkyl, hydroxy, hydroxyalkyl, phenyl, oxo, cyanoalkyl, -alkylene-C(O)N(alkyl)$_2$, hydroxyalkyl, haloalkyl, halo, or alkyoxy. Preferred substituents are halo, hydroxy, and phenyl.

The term "heterocycloalkyl" refers to a monovalent saturated 5- to 11-membered monocyclic, bicyclic or spirocyclic ring system containing one, two or three ring heteroatoms selected from N, O and S, the remaining ring atoms being carbon atoms. In case of monocyclic heterocycloalkyl, the ring is preferably 5- or 6-membered, in case of bicyclic heterocycloalkyl, the bicyclic ring is preferably 7-, 8- or 9-membered and in case of spirocyclic heterocycloalkyl, the ring system is preferably 10- or 11-membered. "Heterocycloalkyl" may be unsubstituted or substituted as described herein. Examples for substituents on heterocycloalkyl are independently selected from alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy.

The term "5- or 6-membered heterocycloalkyl" refers to a monovalent saturated monocycle as defined above. Preferably, 5- or 6-membered heterocloalkyl is a monovalent saturated monocyclic ring containing one or two ring heteroatoms selected from N, O, and S. Examples for 5- or 6-membered heterocycloclakyl moieties are tetrahydropyranyl, tetrahydrothiopyranyl, tetrahydrofuranyl, tetrahydrothiophenyl, pyrrolidinyl, imidazolidinyl, morpholinyl, thiomorpholinyl, piperidinyl, and piperazinyl. The 5- or 6-membered heterocycloalkyl moiety is optionally substituted as described herein.

The term "7-, 8- or 9-membered bicyclic heterocycloalkyl" refers to a saturated bicyclic ring system as defined above. Preferably, 7-, 8- or 9-membered bicyclic heterocycloalkyl is a monovalent saturated bicyclic ring system containing one or two ring heteroatoms selected from N, O and S. Thereby, "bicyclic" describes a system consisting of two saturated rings having two ring atoms in common, i.e. the bridge separating the two rings is either a bond or a chain of preferably one or two atoms. Examples for 7-, 8- or 9-membered bicyclic heterocycloalkyl are 2-oxa-5-aza-hicyclo[2.2.1]heptyl, 8-oxa-3-aza-bicyclo[3.2.1]octyl, 8-aza-bicyclo[3.2.1]octyl, 3-oxa-9-aza-bicyclo[3.3.1]nonyl, 9-aza-bicyclo[3.3.1]nonyl and 3-thia-9-aza-bicyclo[3.3.1]nonyl. 7-, 8- or 9-membered bicyclic heterocycloalkyl is optionally substituted as described herein.

The term "10- or 11-membered spirocyclic heterocycloalkyl" denotes a monovalent bicyclic saturated moiety with the rings connected through just one atom, containing one, two or three ring heteroatoms selected from N, O or S. Examples for 10- or 11-membered spirocyclic heterocycloalkyl are 2-oxa-8-aza-spiro[4.5]decanyl and 1,4-dioxa-8-aza-spiro[4.5]decanyl. The 10- or 11-membered spirocyclic heterocycloalkyl is optionally substituted as described herein.

When indicating the number of substituents, the term "one or more" means from one substituent to the highest possible number of substitution, i.e. replacement of one hydrogen up to replacement of all hydrogens by substituents. Thereby, one, two or three substituents are preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In detail, the present invention relates to compounds of the general formula (I)

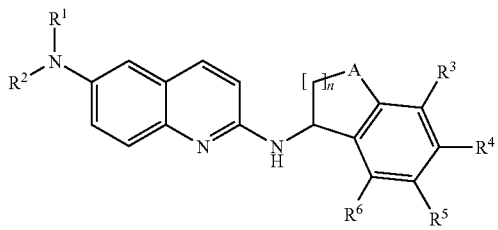

I wherein
A is —$CH_2$— or —O—;
$R^1$ is hydrogen or alkyl;
$R^2$ is hydrogen,
5- or 6-membered heterocycloalkyl,
—$(CH_2)_a$—$R^a$, wherein $R^a$ is hydrogen, alkoxy, hydroxy, cyano, or $NR^iR^{ii}$, wherein $R^i$ and $R^{ii}$ are each independently hydrogen, alkyl or C(O)O-alkyl,
allyl,
—C(=NH)—S—$R^b$, wherein $R^b$ is alkyl, cycloalkyl, haloalkyl, hydroxyalkyl, cyanoalkyl, or alkenyl,
—C(=$NR^c$)$NR^dR^e$, wherein $R^c$, $R^d$, and $R^e$ are each independently hydrogen, alkyl, cycloalkyl, heterocycloalkyl, or wherein $R^d$ and $R^e$ together with the nitrogen to which they are bound form a heterocycloalkyl,
—C(O)$R^f$, wherein $R^f$ is alkyl, —$(CH_2)_b$-cycloalkyl, —$(CH_2)_b$—Oalkyl, —$(CH_2)_b$-heterocycloalkyl, —O-heterocycloalkyl, or —$(CH_2)_b$—$NR^{iii}R^{iv}$,
wherein $R^{iii}$ and $R^{iv}$ are each independently hydrogen, alkyl, —C(O)Oalkyl, —$(CH_2)_b$-cycloalkyl, —$(CH_2)_a$—Oalkyl, bicyclic cycloalkyl, bicyclic cycloalkenyl, —$(CH_2)_b$-heterocycloalkyl, —$(CH_2)_a$—O-heterocycloalkyl,
or —$(CH_2)_a$—NR'R", wherein R' and R" are each independently hydrogen, alkyl or cycloalkyl,
—C(S)NR'$R^{vi}$, wherein $R^v$ and $R^{vi}$ are each independently H, alkyl or cycloalkyl,
—$S(O)_2NR^{vii}R^{viii}$, wherein $R^{vii}$ and $R^{viii}$ are each independently H, alkyl, —C(O)Oalkyl, alkylene-O alkyl, cycloalkyl, or heterocycloalkyl,
—$S(O)_2$-heterocycloalkyl, or
$R^1$ and $R^2$ together with the N atom to which they are bound form a 5- or 6-membered heterocycloalkyl,
$R^3$, $R^4$, $R^5$ and $R^6$ are each independently selected from the group consisting of H, halo, alkyl, haloalkyl, hydroxyalkyl, cyanoalkyl, alkoxy, haloalkoxy, —O-alkylene-O-alkyl, hydroxyl, oxo, cyano, nitro and $NR^{ix}R^x$, wherein $R^{ix}$ and $R^x$ are each independently H or alkyl,
a is 1 to 6,
b is 0 to 6, and
n is 1 or 2, and wherein
heterocycloalkyl is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-$S(O)_2$-alkyl, -alkylene-C(O)N(alkyl)$_2$, halo, haloalkyl and alkyoxy; and wherein
cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, and alkyoxy;
or a pharmaceutically acceptable salt thereof.

In certain embodiments of formula I, a is 1, 2, 3 or 4, preferably 2.

In certain embodiments of formula I, b is 0, 1, 2, 3 or 4; preferably 0 or 1.

In certain embodiments of formula I, $R^1$ is hydrogen or $C_{1-4}$-alkyl, preferably, $R^1$ is hydrogen.

In certain embodiments of formula I, $R^2$ is
hydrogen,
5- or 6-membered heterocycloalkyl,
—$(CH_2)_a$—$R^a$, wherein $R^a$ is hydrogen, alkoxy, hydroxy, cyano, or $NR^iR^{ii}$, wherein $R^i$ and $R^{ii}$ are each independently hydrogen, alkyl or C(O)O-alkyl,
allyl,
—C(=NH)—S—$R^b$, wherein $R^b$ is alkyl, cycloalkyl, haloalkyl, hydroxyalkyl, cyanoalkyl, or alkenyl,
—C(=$NR^c$)$NR^dR^e$, wherein $R^c$, $R^d$, and $R^e$ are each independently hydrogen, alkyl, cycloalkyl, 5- or 6-membered heterocycloalkyl, or wherein $R^d$ and $R^e$ together with the nitrogen to which they are bound form a 5- or 6-membered heterocycloalkyl,
—C(O)$R^f$, wherein $R^f$ is
alkyl,
—(CH$_2$)$_b$-cycloalkyl,
—(CH$_2$)$_b$—Oalkyl,
—(CH$_2$)$_b$-heterocycloalkyl, wherein the heterocycloalkyl is a 5- or 6-membered monocycle or a 7-, 8- or 9-membered bicycle,
—O-heterocycloalkyl, wherein the heterocycloalkyl is a 5- or 6-membered monocycle,
10- or 11-membered spirocyclic heterocycloalkyl,
—(CH$_2$)$_b$—NR$^{iii}$R$^{iv}$, wherein R$^{iii}$ and R$^{iv}$ are each independently
hydrogen,
alkyl,
—C(O)Oalkyl,
—(CH$_2$)$_b$-cycloalkyl,
—(CH$_2$)$_a$—Oalkyl,
7- or 8-membered bicyclic cycloalkyl or cycloalkenyl,
—(CH$_2$)$_b$-heterocycloalkyl, wherein the heterocycloalkyl is a 5- or 6-membered monocycle or a 7-, 8- or 9-membered bicycle,
—(CH$_2$)$_a$—O-heterocycloalkyl, wherein the heterocycloalkyl is a 5- or 6-membered monocycle, or
—(CH$_2$)$_a$—NR'R", wherein R' and R" are each independently hydrogen, alkyl or cycloalkyl,
—C(S)NR'R$^{vi}$, wherein R$^v$ and R$^{vi}$ are each independently H, alkyl or cycloalkyl,
—S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or 5- or 6-membered heterocycloalkyl,
—S(O)$_2$-heterocycloalkyl, wherein the heterocycloalkyl is a 5- or 6-membered monocycle or a 7-, 8- or 9-membered bicycle, or
—S(O)$_2$-spirocyclic heteroalkyl, wherein the spirocyclic heteroalkyl is 10- or 11-membered;
a is 1 to 6, preferably 1 to 4,
b is 0 to 6, preferably 0 to 4, and wherein
heterocycloalkyl is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy; and wherein
cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, and alkyoxy.
In certain embodiments, R$^2$ is
hydrogen,
6-membered heterocycloalkyl,
—(CH$_2$)$_a$—NR$^i$R$^{ii}$, wherein R$^i$ and R$^{ii}$ are each independently hydrogen, alkyl or C(O)O-alkyl,
allyl,
—C(=NH)—S-alkyl
—C(=NR$^c$)NR$^d$R$^e$, wherein R$^c$, R$^d$, and R$^e$ are each independently hydrogen, alkyl, cycloalkyl, 6-membered heterocycloalkyl, or wherein R$^d$ and R$^e$ together with the nitrogen to which they are bound form a 6-membered heterocycloalkyl,
—C(O)$R^f$, wherein $R^f$ is
alkyl,
—(CH$_2$)$_b$-cycloalkyl,
—(CH$_2$)$_b$—Oalkyl,
—(CH$_2$)$_b$-heterocycloalkyl, wherein the heterocycloalkyl is a 5- or 6-membered monocycle or a 7-membered bicycle, or
—O-heterocycloalkyl, wherein the heterocycloalkyl is a 6-membered monocycle,
10-membered spirocyclic heterocycloalkyl,
—(CH$_2$)$_b$—NR$^{iii}$R$^{iv}$, wherein R$^{iii}$ and R$^{iv}$ are each independently
hydrogen,
alkyl,
—C(O)Oalkyl,
—(CH$_2$)$_b$-cycloalkyl,
—(CH$_2$)$_a$—Oalkyl,
7-membered bicyclic cycloalkyl,
—(CH$_2$)$_b$-heterocycloalkyl, wherein the heterocycloalkyl is a 5- or 6-membered monocycle or a 8- or 9-membered bicycle,
—(CH$_2$)$_a$—O-heterocycloalkyl, wherein the heterocycloalkyl is a 6-membered monocycle, or
—(CH$_2$)$_a$—NR'R", wherein R' and R" are each independently alkyl or cycloalkyl,
—C(S)NH$_2$,
—S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or 6-membered heterocycloalkyl,
—S(O)$_2$-heterocycloalkyl, wherein the heterocycloalkyl is a 5- or 6-membered monocycle or a 7-membered bicycle, or
—S(O)$_2$-spirocyclic heteroalkyl, wherein the spirocyclic heteroalkyl is 10- or 11-membered,
a is 1 to 6, preferably 1 to 4,
b is 0 to 6, preferably 0 to 4, and wherein
heterocycloalkyl is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy; and wherein
cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, and alkyoxy,
In certain embodiments of the compound of formula I, R$^2$ is
hydrogen,
morpholin-4-yl, 4-methyl-piperazin-1-yl, or piperazin-1-yl,
—(CH$_2$)$_a$—NR$^i$R$^{ii}$, wherein R$^i$ and R$^{ii}$ are each independently hydrogen, alkyl or C(O)O-alkyl, allyl,
—C(=NH)—S-alkyl,
—C(=NR$^c$)NR$^d$R$^e$, wherein R$^c$ is H or alkyl, and R$^d$ and R$^e$ are each independently hydrogen, alkyl, cycloalkyl, 1-methyl-piperidin-4-yl, piperidin-4-yl, or wherein R$^d$ and R$^e$ together with the nitrogen to which they are bound form a morpholine ring, a piperazine ring, or a 4-methyl-piperazine ring,
—C(O)$R^f$, wherein $R^f$ is
alkyl,
—(CH$_2$)$_b$-cycloalkyl,
—(CH$_2$)$_b$—Oalkyl,
—(CH$_2$)$_b$-heterocycloalkyl, wherein the heterocycloalkyl is selected from the group consisting of morpholin-4-yl, tetrahydropyran-4-yl, 4-methyl-piperazin-1-yl, 4-isopropyl-piperazin-1-yl, piperazin-1-yl, thiomorpholin-4-yl, 4-hydroxy-4-methyl-piperidine-1-yl, (1S,4S)-2-oxa-5-aza-bicyclo[2.2.1]heptan-5-yl, (1R,5S)-8-oxa-3-azabicyclo[3.2.1]octan-3-yl, 4-hydroxymethyl-piperidine-1-yl, 4-tert-butyl-piperazine-1-yl, 4-methyl-piperidine-1-yl, and piperidine-1-yl,
—O-heterocycloalkyl, wherein the heterocycloalkyl is 4-methyl-piperidine-1-yl, or piperidine-1-yl,
2-oxa-8-aza-spiro[4.5]decan-8-yl,
—(CH$_2$)$_b$—NR$^{iii}$R$^{iv}$, wherein R$^{iii}$ and R$^{iv}$ are each independently
hydrogen,
alkyl,
—C(O)Oalkyl,
—(CH$_2$)$_b$-cycloalkyl, wherein cycloalkyl is selected from cyclohexyl, 4-hydroxycyclohexyl, cyclopropyl, 2-phenyl-cycloprop-1-yl, or cyclopentyl,
—(CH$_2$)$_a$—Oalkyl,
—(CH$_2$)$_a$—NR'R", wherein R' and R" are each independently alkyl or cycloalkyl, bicyclo[2.2.1]heptanyl, or
—(CH$_2$)$_b$-heterocycloalkyl, wherein the heterocycloalkyl is 4-methyl-piperazin-1-yl, tetrahydro-pyran-4-yl, 1-methyl-piperidin-4-yl, 1-benzyl-pyrrolidin-3-yl, 1,1-dioxo-tetrahydro-thiophen-3-yl, morpholin-4-yl, piperidin-4-yl, 1-tert-butoxycarbonyl-piperidin-4-yl, 1-cyclopropyl-piperidin-4-yl, 1-isopropyl-piperidin-4-yl, 1-(2-methoxyethyl)-piperidin-4-yl, 1-(2-fluoroethyl)-piperidin-4-yl, 1-(3,3,3-trifluoropropyl)-piperidin-4-yl, 1-(2-methylsulfanyl-ethyl)-piperidin-4-yl, 3-(endo)-9-methyl-9-azabicyclo[3.3.1]non-3-yl, 1-(3,3,3-trifluoropropionyl)-piperidin-4-yl, 1,1-dioxo-hexahydro-thiopyran-4-yl, 3-endo-(8-methyl-8-aza-bicyclo[3.2.1]oct-3-yl, 1-(2-fluoro-acetyl)-piperidin-4-yl, 1-methyl-pyrrolidin-3-yl, 1-methoxycarbonyl-piperidin-4-yl, (3-exo)-8-cyclopropyl-8-aza-bicyclo[3.2.1]oct-3-yl, (3-exo)-9-(2,2,2-trifluoro-ethyl)-9-aza-bicyclo[3.3.1]non-3-yl, (3-exo)-8-methyl-8-aza-bicyclo[3.2.1]oct-3-yl, (7-exo)-9-methyl-3-oxa-9-aza-bicyclo[3.3.1]non-7-yl, 1-methyl-pyrrolidin-3-yl, (3-exo)-9-cyclopropyl-9-aza-bicyclo[3.3.1]non-3-yl, (7-exo)-9-methyl-3-thia-9-aza-bicyclo[3.3.1]non-7-yl, 1-cyanomethyl-piperidin-4-yl, 1-(2-methanesulfonyl-ethyl)-piperidin-4-yl, (N,N-dimethylamino-carbonylmethylene)-piperidin-4-yl, 1-(2-hydroxy-ethyl)-piperidin-4-yl, (3-exo)-9-isopropyl-9-aza-bicyclo[3.3.1]non-3-yl, (3-exo)-8-cyclopropyl-8-aza-bicyclo[3.2.1]oct-3-yl, (3-exo)-8-isopropyl-8-aza-bicyclo[3.2.1]oct-3-yl, (1R,5S)-8-methyl-8-aza-bicyclo[3.2.1]oct-3-yl, (1R,5S)-9-isopropyl-3-oxa-9-aza-bicyclo[3.3.1]non-3-yl, or 1-(2-hydroxy-2-methyl-propyl)-piperidin-4-yl,
—C(S)NH$_2$,
—S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or tetrahydro-2H-pyran-4-yl,
—S(O)$_2$-heterocycloalkyl, wherein the heterocycloalkyl is selected from the group consisting of pyrrolidin-1-yl, 3,3-difluoro-pyrrolidin-1-yl, morpholin-4-yl, 4-methyl-piperazin-1-yl, piperazin-1-yl, thiomorpholin-4-yl, 1,1-dioxo-thiomorpholin-4-yl, 4-methoxymethyl-piperidin-1-yl, 4-methoxy-piperidine-1-yl, (1S,4S)-2-oxa-5-azabicyclo[2.2.1]hept-5-yl, (1R,5S)-8-oxa-3-azabicyclo[3.2.1]oct-3-yl, or
—S(O)$_2$-spirocyclic heteroalkyl, wherein the spirocyclic heteroalkyl is 2-oxa-8-aza-spiro[4.5]decan-8-yl, or 1,4-dioxa-8-aza-spiro[4.5]decanyl,
a is 1 to 6, preferably 1 to 4,
b is 0 to 6, preferably 0 to 4.

In certain embodiments of the compound of formula I, R$^2$ is —C(O)R$^f$, wherein R$^f$ is —(CH$_2$)$_b$-cycloalkyl, —(CH$_2$)$_b$-heterocycloalkyl, or
—(CH$_2$)$_b$—NR$^{iii}$R$^{iv}$, wherein R$^{iii}$ and R$^{iv}$ are each independently hydrogen, alkyl, —C(O)Oalkyl, —(CH$_2$)$_b$-cycloalkyl, —(CH$_2$)$_a$—Oalkyl, bicyclic cycloalkyl, bicyclic cycloalkenyl, —(CH$_2$)$_b$-heterocycloalkyl, or —(CH$_2$)$^a$—NR'R", wherein R' and R" are each independently hydrogen, alkyl or cycloalkyl,
—S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or heterocycloalkyl, or
—S(O)$_2$-heterocycloalkyl,
a is 1 to 6, preferably 1 to 4, more preferably 2,
b is 0 to 6, preferably 0 to 4, more preferably 0 or 1,
heterocycloalkyl is unsubstituted or substituted with one or more substituents
independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy; and
cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, and alkyoxy.

In certain embodiments of formula I, R$^1$ and R$^2$ together with the nitrogen to which they are bound form a 5- or 6-membered heterocycloalkyl which is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy.

In certain embodiments of formula I, R$^1$ and R$^2$ together with the nitrogen to which they are bound form 3-methyl-imidazolidin-2-one or 4-methyl-piperazin-1-yl.

In certain embodiments of formula I, A is —CH$_2$— and n is 1 or 2, or A is —O— and n is 1.

In certain embodiments of formula I, A is —CH$_2$— and n is 1.

In certain embodiments of formula I, A is —CH$_2$— and n is 2.

In certain embodiments of formula I, A is —O— and n is 1.

In certain embodiments of the compounds of formula I, R$^3$, R$^4$, R$^5$ and R$^6$ are as defined above.

In certain embodiments of the compounds of formula I, R$^3$, R$^4$, R$^5$ and R$^6$ are independently selected from the group consisting of H, halo, alkoxy, alkyl, haloalkoxy, and —O-alkylene-O-alkyl.

In certain embodiments of the compounds of formula I, R$^3$ is H, halo or alkyl; preferably H, chloro or methyl.

In certain embodiments of the compound of formula I, R$^4$ is H, halo or alkyl; preferably H, fluoro or methyl.

In certain embodiments of the compound of formula I, R$^5$ is H or halo; preferably H, fluoro or chloro.

In certain embodiments of the invention, R$^6$ is H, alkoxy, alkyl, halo, or —O-alkylene-O-alkyl; preferably H, C$_{1-4}$-alkoxy, C$_{1-4}$-alkyl, fluoro or —O—CH$_2$CH$_2$OMe.

In certain embodiments, R$^3$ to R$^6$ are all H.

In certain embodiments, R$^3$ to R$^5$ are all H and R$^6$ is alkoxy, alkyl, halo, or —O-alkylene-O-alkyl.

In certain embodiments, R$^3$, R$^5$ and R$^6$ are all H and R$^4$ is halo, preferably fluoro.

In certain embodiments, R$^3$, R$^4$ and R$^6$ are all H and R$^5$ is halo.

In certain embodiments I, $R^3$ and $R^5$ are chloro, $R^4$ is H, and $R^6$ is methoxy.

In certain embodiments, $R^3$ is alkyl, $R^4$ and $R^5$ are H, and $R^6$ is alkoxy.

In certain embodiments, $R^3$ and $R^5$ is H, $R^4$ is alkyl and $R^6$ is alkoxy.

In certain embodiments, not all $R^1$, $R^2$, $R^3$, $R^4$, $R^5$ and $R^6$ are simultaneously H.

It is to be understood that all combinations of n, A, $R^1$, $R^2$, $R^3$, $R^4$, $R^5$ and $R^6$ as disclosed herein are encompassed by present invention.

Preferred compounds of formula I are those as shown in the examples below.

More preferred are the following compounds of formula I:
1-[2-((R)-Indan-1-ylamino)-quinolin-6-yl]-3-isopropyl-urea,
1-Cyclohexyl-3-[2-((R)-indan-1-ylamino)-quinolin-6-yl]-urea,
1-[2-((R)-Indan-1-ylamino)-quinolin-6-yl]-3-methyl-urea,
1-tert-Butyl-3-[2-((R)-indan-1-ylamino)-quinolin-6-yl]-urea,
[2-((R)-Indan-1-ylamino)-quinolin-6-yl]-urea,
rac-1-Isopropyl-3-[2-(7-methoxy-indan-1-ylamino)-quinolin-6-yl]-urea,
(−)-1-Isopropyl-3-[2-(7-methoxy-indan-1-ylamino)-quinolin-6-yl]-urea,
rac-1-Isopropyl-3-[2-(8-methoxy-1,2,3,4-tetrahydro-naphthalen-1-ylamino)-quinolin-6-yl]-urea,
1-[2-((R)-Indan-1-ylamino)-quinolin-6-yl]-3-(2-methoxyethyl)-urea,
1-(2-Dimethylamino-ethyl)-3-[2-((R)-indan-1-ylamino)-quinolin-6-yl]-urea,
1-[2-((R)-Indan-1-ylamino)-quinolin-6-yl]-3-(tetrahydropyran-4-yl)-urea,
1-[2-((R)-Indan-1-ylamino)-quinolin-6-yl]-3-(1-methyl-piperidin-4-yl)-urea,
1-Cyclopropyl-3-[2-((R)-indan-1-ylamino)-quinolin-6-yl]-urea,
1-Cyclopropylmethyl-3-[2-((R)-indan-1-ylamino)-quinolin-6-yl]-urea,
1-Bicyclo[2.2.1]hept-2-yl-3-[2-((R)-indan-1-ylamino)-quinolin-6-yl]-urea,
1-[2-(Cyclopropyl-methyl-amino)-ethyl]-3-[2-((R)-indan-1-ylamino)-quinolin-6-yl]-urea,
rac-1-[2-(2,3-Dihydro-benzofuran-3-ylamino)-quinolin-6-yl]-3-(1-methyl-piperidin-4-yl)-urea,
1-[2-((R)-Indan-1-ylamino)-quinolin-6-yl]-3-piperidin-4-yl-urea,
rac-1-[2-(7-Methoxy-indan-1-ylamino)-quinolin-6-yl]-3-(1-methyl-piperidin-4-yl)-urea,
1-(1-Cyclopropyl-piperidin-4-yl)-3-[2-((R)-indan-1-ylamino)-quinolin-6-yl]-urea,
1-[2-((R)-Indan-1-ylamino)-quinolin-6-yl]-3-(1-isopropyl-piperidin-4-yl)-urea,
1-[2-((R)-Indan-1-ylamino)-quinolin-6-yl]-3-[1-(2-methoxy-ethyl)-piperidin-4-yl]-urea,
rac-1-(1-Isopropyl-piperidin-4-yl)-3-[2-(7-methoxy-indan-1-ylamino)-quinolin-6-yl]-urea,
rac-1-[1-(2-Methoxy-ethyl)-piperidin-4-yl]-3-[2-(7-methoxy-indan-1-ylamino)-quinolin-6-yl]-urea,
rac-1-[1-(2-Fluoro-ethyl)-piperidin-4-yl]-3-[2-(7-methoxy-indan-1-ylamino)-quinolin-6-yl]-urea,
rac-1-[2-(7-Methoxy-indan-1-ylamino)-quinolin-6-yl]-3-[1-(3,3,3-trifluoro-propyl)-piperidin-4-yl]-urea,
1-[2-((R)-Indan-1-ylamino)-quinolin-6-yl]-3-[1-(2-methylsulfanyl-ethyl)-piperidin-4-yl]-urea,
rac-1-[2-(7-Methoxy-indan-1-ylamino)-quinolin-6-yl]-3-(9-methyl-9-aza-bicyclo[3.3.1]non-3-yl)-urea,
rac-1-[2-(7-Methoxy-indan-1-ylamino)-quinolin-6-yl]-3-[1-(2-methylsulfanyl-ethyl)-piperidin-4-yl]-urea,
rac-1-[2-(7-Methoxy-indan-1-ylamino)-quinolin-6-yl]-3-[1-(3,3,3-trifluoro-propionyl)-piperidin-4-yl]-urea,
rac-1-(1-Cyclopropyl-piperidin-4-yl)-3-[2-(7-methoxy-indan-1-ylamino)-quinolin-6-yl]-urea,
rac-1-(1-Cyclopropyl-piperidin-4-yl)-3-[2-(8-methoxy-1,2,3,4-tetrahydro-naphthalen-1-ylamino)-quinolin-6-yl]-urea,
rac-1-[2-(8-Methoxy-1,2,3,4-tetrahydro-naphthalen-1-ylamino)-quinolin-6-yl]-3-(1-methyl-piperidin-4-yl)-urea,
rac-1-[1-(2-Methoxy-ethyl)-piperidin-4-yl]-3-[2-(8-methoxy-1,2,3,4-tetrahydro-naphthalen-1-ylamino)-quinolin-6-yl]-urea,
rac-1-[1-(2-Fluoro-ethyl)-piperidin-4-yl]-3-[2-(8-methoxy-1,2,3,4-tetrahydro-naphthalen-1-ylamino)-quinolin-6-yl]-urea,
1-[2-((R)-Indan-1-ylamino)-quinolin-6-yl]-3-[1-(3,3,3-trifluoro-propyl)-piperidin-4-yl]-urea,
N'-{2-[(1R)-2,3-dihydro-1H-inden-1-ylamino]quinolin-6-yl}-N,N-dimethylsulfamide,
rac-N'-{2-[(7-methoxy-2,3-dihydro-1H-inden-1-yl)amino]quinolin-6-yl}-N,N-dimethylsulfamide,
N-{2-[(1R)-2,3-dihydro-1H-inden-1-ylamino]quinolin-6-yl}sulfamide hydrochloride,
Pyrrolidine-1-sulfonic acid [2-((R)-indan-1-ylamino)-quinolin-6-yl]-amide,
3,3-Difluoro-pyrrolidine-1-sulfonic acid [2-((R)-indan-1-ylamino)-quinolin-6-yl]-amide,
(2-Methoxy-ethyl)-methyl-sulfonic acid [2-((R)-indan-1-ylamino)quinolin-6-yl]-amide,
Morpholine-4-sulfonic acid [2-((R)-indan-1-ylamino)-quinolin-6-yl]-amide,
Thiomorpholine-4-sulfonic acid [2-((R)-indan-1-ylamino)-quinolin-6-yl]-amide,
1,4-Dioxa-8-aza-spiro[4.5]decane-8-sulfonic acid [2-((R)-indan-1-ylamino)-quinolin-6-yl]-amide,
N-cyclopropyl-N'-{2-[(1R)-2,3-dihydro-1H-inden-1-ylamino]quinolin-6-yl}-N-methylsulfamide,
(1S,4S)-2-Oxa-5-aza-bicyclo[2.2.1]heptane-5-sulfonic acid [2-((R)-indan-1-ylamino)-quinolin-6-yl]-amide,
(1S,4S)-2-Oxa-5-aza-bicyclo[2.2.1]heptane-5-sulfonic acid [2-(8-methoxy-1,2,3,4-tetrahydro-naphthalen-1-ylamino)-quinolin-6-yl]-amide,
rac-1-Isopropyl-3-[2-(7-methoxy-4-methyl-indan-1-ylamino)-quinolin-6-yl]-urea,
1-[1-(2-Fluoro-ethyl)-piperidin-4-yl]-3-[2-((R)-indan-1-ylamino)-quinolin-6-yl]-urea,
1-((3-exo)-8-Cyclopropyl-8-aza-bicyclo[3.2.1]oct-3-yl)-3-[2-((R)-indan-1-ylamino)-quinolin-6-yl]-urea,
1-[2-((R)-Indan-1-ylamino)-quinolin-6-yl]-3-((3-exo)-8-methyl-8-aza-bicyclo[3.2.1]oct-3-yl)-urea,
rac-1-[2-(5-Fluoro-indan-1-ylamino)-quinolin-6-yl]-3-isopropyl-urea,
1-((3-exo)-9-Cyclopropyl-9-aza-bicyclo[3.3.1]non-3-yl)-3-[2-((R)-indan-1-ylamino)-quinolin-6-yl]-urea,
rac-1-[2-(5-Fluoro-indan-1-ylamino)-quinolin-6-yl]-3-(1-isopropyl-piperidin-4-yl)-urea,
rac-1-Isopropyl-3-[2-(7-methoxy-5-methyl-indan-1-ylamino)-quinolin-6-yl]-urea,
rac-1-[2-(7-Methoxy-5-methyl-indan-1-ylamino)-quinolin-6-yl]-3-(1-methyl-piperidin-4-yl)-urea,
1-(1-Cyanomethyl-piperidin-4-yl)-3-[2-((R)-indan-1-ylamino)-quinolin-6-yl]-urea, 1-[2-((R)-Indan-1-ylamino)-quinolin-6-yl]-3-[1-(2-methanesulfonyl-ethyl)-piperidin-4-yl]-urea,
2-(4-{3-[2-((R)-Indan-1-ylamino)-quinolin-6-yl]-ureido}-piperidin-1-yl)-N,N-dimethylacetamide,
1-[1-(2-Hydroxy-ethyl)-piperidin-4-yl]-3-[2-((R)-indan-1-ylamino)-quinolin-6-yl]-urea,
[2-((R)-Indan-1-ylamino)-quinolin-6-yl]-carbamic acid isopropyl ester,
rac-N-[2-(7-Methoxy-indan-1-ylamino)-quinolin-6-yl]-2-(4-methyl-piperazin-1-yl)-acetamide,
rac-Cyclopropanecarboxylic acid [2-(7-methoxy-indan-1-ylamino)-quinolin-6-yl]-amide,
rac-Cyclopropanecarboxylic acid [2-(5-fluoro-indan-1-ylamino)-quinolin-6-yl]-amide,
rac-1-[2-(7-Fluoro-indan-1-ylamino)-quinolin-6-yl]-3-isopropyl-urea,
(1S,4S)-2-Oxa-5-aza-bicyclo[2.2.1]heptane-5-sulfonic acid [2-(7-methoxy-indan-1-ylamino)-quinolin-6-yl]-amide,
[2-((R)-Indan-1-ylamino)-quinolin-6-yl]-thiourea,
rac-1-[2-(6-Fluoro-indan-1-ylamino)-quinolin-6-yl]-3-(1-isopropyl-piperidin-4-yl)-urea,
rac-1-[2-(7-Fluoro-indan-1-ylamino)-quinolin-6-yl]-3-(1-isopropyl-piperidin-4-yl)-urea,
rac-Cyclopropanecarboxylic acid [2-(7-fluoro-indan-1-ylamino)-quinolin-6-yl]-amide,
N-[2-((R)-Indan-1-ylamino)-quinolin-6-yl]-N',N''-diisopropyl-guanidine,
1-[2-((R)-Indan-1-ylamino)-quinolin-6-yl]-3-((3-exo)-9-isopropyl-9-aza-bicyclo[3.3.1]non-3-yl)-urea,
1-[2-((R)-Indan-1-ylamino)-quinolin-6-yl]-3-((3-exo)-8-isopropyl-8-aza-bicyclo[3.2.1]oct-3-yl)-urea,
rac-$N^2$-(7-Methoxy-indan-1-yl)-quinoline-2,6-diamine,
rac-1-(1-Isopropyl-piperidin-4-yl)-3-[2-(7-methoxy-indan-1-ylamino)-quinolin-6-yl]-1-methyl-urea,
rac-1-(1-Isopropyl-piperidin-4-yl)-3-[2-(4-methoxy-2,3-dihydro-benzofuran-3-ylamino)-quinolin-6-yl]-urea,
rac-1-[2-(4-Ethoxy-2,3-dihydro-benzofuran-3-ylamino)-quinolin-6-yl]-3-(1-isopropyl-piperidin-4-yl)-urea,
rac-1-((3-exo)-8-Isopropyl-8-aza-bicyclo[3.2.1]oct-3-yl)-3-[2-(7-methoxy-indan-1-ylamino)-quinolin-6-yl]-urea,
rac-1-((3-exo)-8-Isopropyl-8-aza-bicyclo[3.2.1]oct-3-yl)-3-[2-(7-methoxy-indan-1-ylamino)-quinolin-6-yl]-1-methyl-urea,
rac-1-[1-(2-Hydroxy-ethyl)-piperidin-4-yl]-3-[2-(7-methoxy-indan-1-ylamino)-quinolin-6-yl]-urea,
rac-1-[1-(2-Hydroxy-2-methyl-propyl)-piperidin-4-yl]-3-[2-(7-methoxy-indan-1-ylamino)-quinolin-6-yl]-1-methyl-urea,
rac-Cyclopropanecarboxylic acid [2-(4-methoxy-2,3-dihydro-benzofuran-3-ylamino)-quinolin-6-yl]-amide,
rac-1-[2-(5-Fluoro-indan-1-ylamino)-quinolin-6-yl]-3-[1-(2-hydroxy-ethyl)-piperidin-4-yl]-urea,
rac-1-[1-(2-Hydroxy-ethyl)-piperidin-4-yl]-3-[2-(7-methoxy-indan-1-ylamino)-quinolin-6-yl]-1-methyl-urea, and
N-[2-((R)-Indan-1-ylamino)-quinolin-6-yl]-2-(4-methyl-piperazin-1-yl)-acetamide.

The present compounds of formula I, their starting materials, their pharmaceutically acceptable salts, and their optical isomers can be prepared by methods known in the art. For example, a process to synthesize representative compounds of formula I can be used which comprises one of the following steps: 2,6-Dichloroquinoline (a) is reacted with a compound of formula (b) to give an intermediate of formula (c), which is subsequently reacted with amine $H_2N(CH_2)_a$—$R^a$ to give product compound (Ia), shown in subsequent scheme 1:

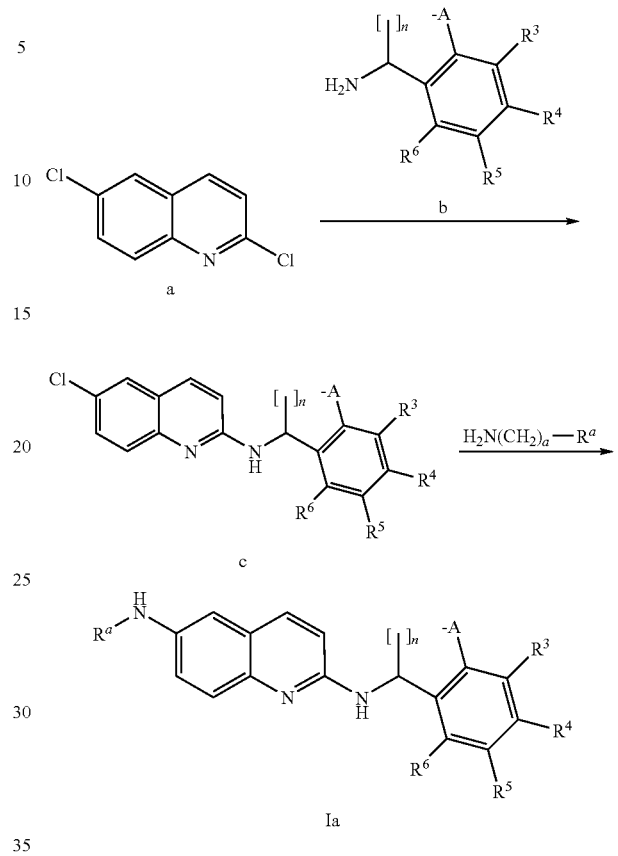

$R^a$, a, n, A and $R^3$ to $R^6$ are as described above.

Moreover, and as may be seen from Scheme 2, compounds of present invention can be synthesized by reacting 2-chloro-6-nitro-quinoline (d) with a compound of formula (b) to give intermediate (e), which is subsequently reduced with hydrogen and palladium on carbon under normal pressure to yield an amine of formula (f). The compound of formula (f) is then either reacted with a compound $R^2$-LG wherein LG denotes a leaving group such as halo or imidazolyl, to give the product of formula Ib. Alternatively, compound (f) is reacted with $R^2$—OH in the presence of a peptide coupling reagent such as 1-(3-dimethylaminopropyl)-3-ethylcarbodiimide hydrochloride, dicyclohexylcarbodiimide, or a carbodiimide in combination with 1-hydroxybenzotriazole.

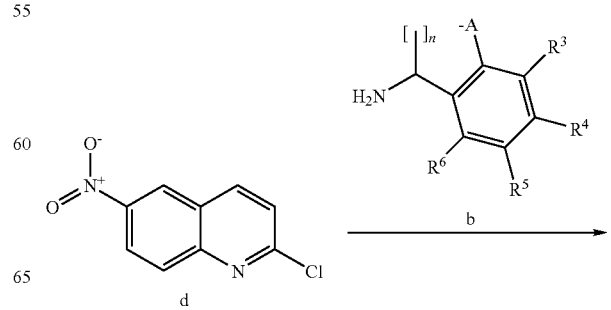

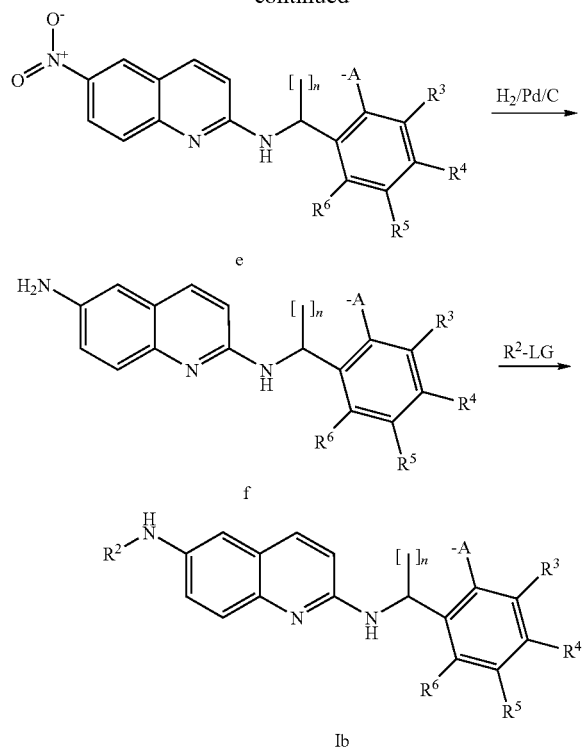

A, n, and $R^3$ to $R^6$ are as described above and $R^2$ is preferably
—C(O)$R^f$, wherein $R^f$ is
- —(CH$_2$)$_b$-cycloalkyl,
- —(CH$_2$)$_b$-heterocycloalkyl, or
- —(CH$_2$)$_b$—NR$^{iii}$R$^{iv}$, wherein R$^{iii}$ and R$^{iv}$ are each independently hydrogen, alkyl, —C(O)Oalkyl, —(CH$_2$)$_b$-cycloalkyl, —(CH$_2$)$_a$—Oalkyl, bicyclic cycloalkyl, bicyclic cycloalkenyl, —(CH$_2$)$_b$-heterocycloalkyl, or
- —(CH$_2$)$_a$—NR'R", wherein R' and R" are each independently hydrogen, alkyl or cycloalkyl,
—S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or heterocycloalkyl, or
—S(O)$_2$-heterocycloalkyl,
a is 1 to 6, preferably 1 to 4, more preferably 2,
b is 0 to 6, preferably 0 to 4, more preferably 0 or 1,
n is 1 or 2, and
heterocycloalkyl is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy; and
cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, and alkyoxy.

As mentioned earlier, the compounds of formula I and their pharmaceutically acceptable addition salts possess valuable pharmaceutical properties. Compounds of the present invention are active on the 5-HT$_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

Test Description

A [$^3$H]LSD radioligand binding assay was used to determine the affinity of the compounds for the recombinant human 5-HT$_{5A}$ receptor, in membranes from transiently (cDNA) expressed 5-HT$_{5A}$ receptors in Human Embryonic Kidney-EBNA (HEK-EBNA) cells. Assay buffer consisted of Tris (50 mM) buffer containing 1 mM EGTA, 10 mM MgCl$_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-1-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. IC$_{50}$ values were calculated using a non-linear curve fitting program and Ki values calculated using the Cheng-Prussoff equation.

The activity of the compounds according to the invention is exemplified in the table 1 below:

| Example | Ki/nM 5-HT$_{5A}$ |
|---|---|
| 3 | 2.5 |
| 5 | 2.9 |
| 7 | 3.4 |
| 8 | 10.9 |
| 9 | 2.9 |
| 12 | 1.5 |
| 13 | 0.9 |
| 15 | 7.7 |
| 17 | 7.0 |
| 18 | 7.3 |
| 19 | 4.0 |
| 20 | 1.8 |
| 21 | 3.9 |
| 23 | 4.7 |
| 26 | 4.8 |
| 32 | 8.2 |
| 35 | 9.6 |
| 39 | 3.9 |
| 40 | 2.2 |
| 41 | 4.1 |
| 42 | 2.4 |
| 43 | 2.5 |
| 44 | 3.0 |
| 45 | 3.0 |
| 46 | 2.7 |
| 47 | 3.0 |
| 48 | 7.7 |
| 50 | 5.2 |
| 51 | 3.9 |
| 52 | 7.5 |
| 53 | 3.1 |
| 55 | 9.7 |
| 57 | 5.8 |
| 58 | 5.3 |
| 59 | 5.9 |
| 63 | 10.4 |
| 66 | 5.6 |
| 68 | 2.5 |
| 72 | 8.4 |
| 73 | 3.2 |
| 74 | 8.9 |
| 75 | 8.3 |
| 76 | 9.9 |
| 78 | 7.0 |

-continued

| Example | Ki/nM 5-HT$_{5A}$ |
|---|---|
| 82 | 22.2 |
| 85 | 9.3 |
| 88 | 2.5 |
| 91 | 6.8 |
| 93 | 8.7 |
| 97 | 2.9 |
| 99 | 3.9 |
| 101 | 3.7 |
| 107 | 4.4 |
| 110 | 7.2 |
| 115 | 4.0 |
| 130 | 3.4 |
| 131 | 2.9 |
| 133 | 4.2 |
| 135 | 5.7 |
| 136 | 6.5 |
| 137 | 1.7 |
| 138 | 8.0 |
| 139 | 4.4 |
| 140 | 2.2 |
| 141 | 8.6 |
| 146 | 6.1 |
| 148 | 2.1 |
| 149 | 14.8 |
| 155 | 6.3 |
| 156 | 3.8 |
| 162 | 8.3 |
| 166 | 33.7 |
| 168 | 7.8 |
| 170 | 7.1 |
| 172 | 3.3 |
| 179 | 7.1 |
| 180 | 2.8 |
| 181 | 4.1 |
| 186 | 5.7 |
| 188 | 8.5 |
| 189 | 1.8 |
| 191 | 6.9 |
| 195 | 7.3 |
| 197 | 3.5 |
| 206 | 6.7 |
| 210 | 6.7 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment of anxiety, depression, sleep disorders and schizophrenia.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Preparation of the compounds of present invention:
Compounds of formula I may be prepared as shown in the following description:
Route 1 Described in Example 1

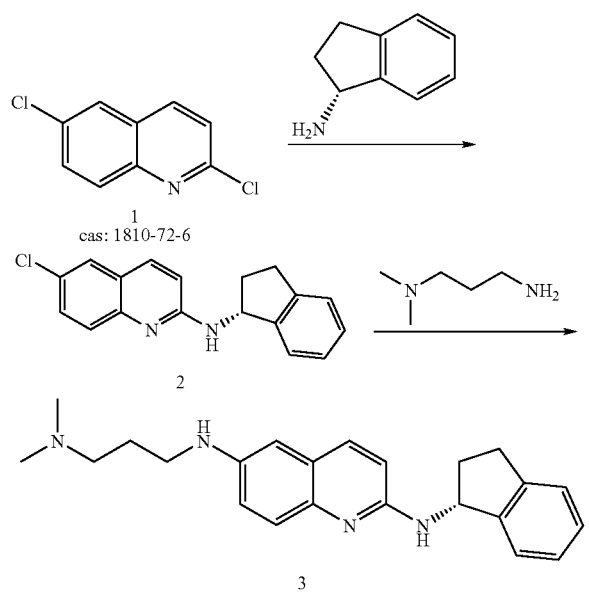

2,6-Dichloro-quinoline (CAS no.: 1810-72-6) is heated with R-(−)-1-aminoindane to yield intermediate 2 which is subsequently cross-coupled with N,N-dimethyl-1,3-propanediamine under palladium-catalyzed conditions to the final product 3.

Route 2 Described in Example 2

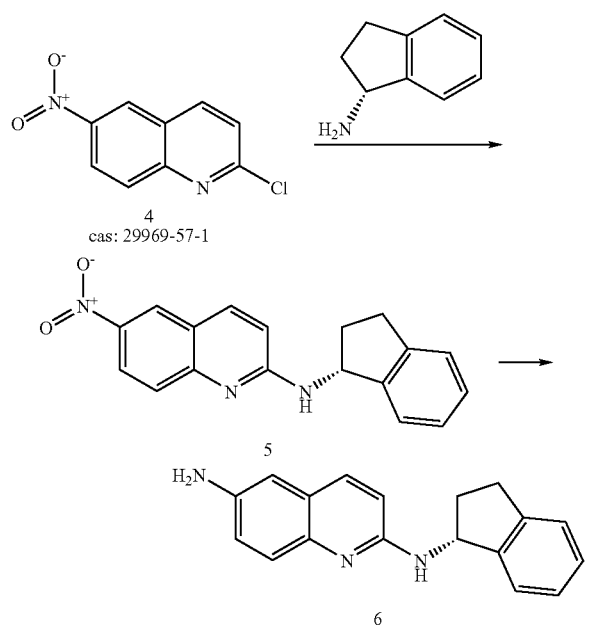

2-Chloro-6-nitro-quinoline (CAS no.: 29969-57-1) is treated with R-(−)-1-aminoindane to yield compound 5 which is then reduced with hydrogen and palladium on carbon under normal pressure to yield 6-amino-quinoline derivative 6.

Route 3 Described in Example 3

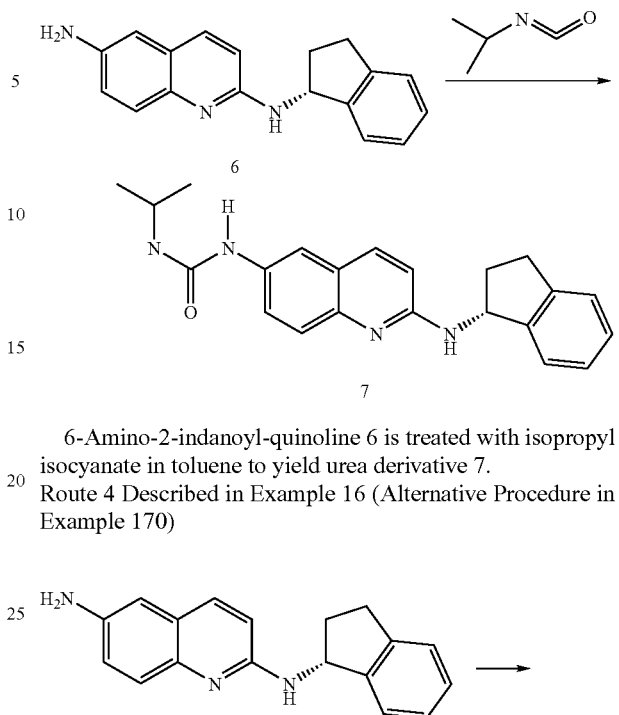

6-Amino-2-indanoyl-quinoline 6 is treated with isopropyl isocyanate in toluene to yield urea derivative 7.

Route 4 Described in Example 16 (Alternative Procedure in Example 170)

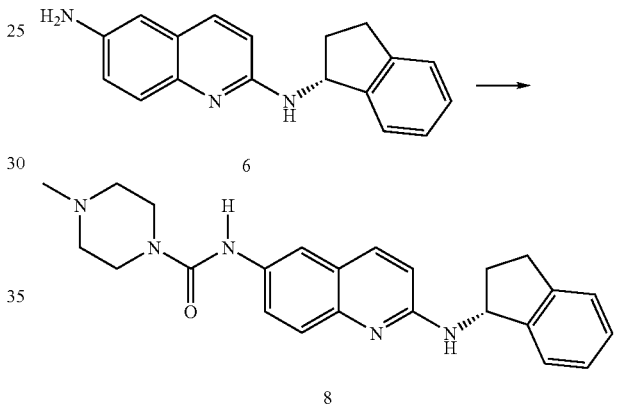

6-Amino-2-indanoyl-quinoline 6 is treated with N-methyl-piperazine, triphosgene and triethylamine in tetrahydrofuran to yield urea derivative 8. Alternatively 6-amino-2-indanoyl-quinoline 6 is treated with N-methyl-piperazine, 4-nitrophenylchloroformate and diisopropyethylamine in dichloromethane to yield urea derivative 8.

Route 5 Described in Example 66

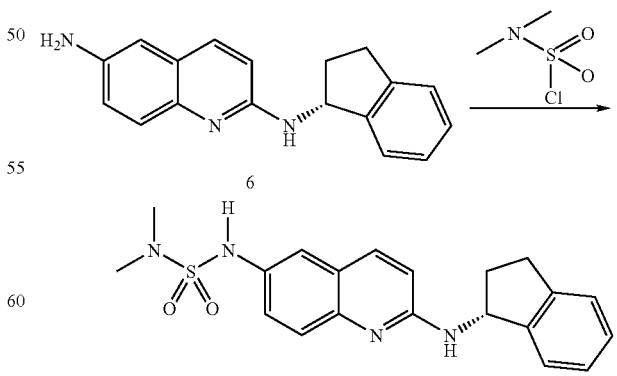

6-Amino-2-indanoyl-quinoline 6 is treated with dimethyl sulfamoyl chloride in pyridine to yield sulfamide derivative 9.

Route 6 Described in Example 71 and 72

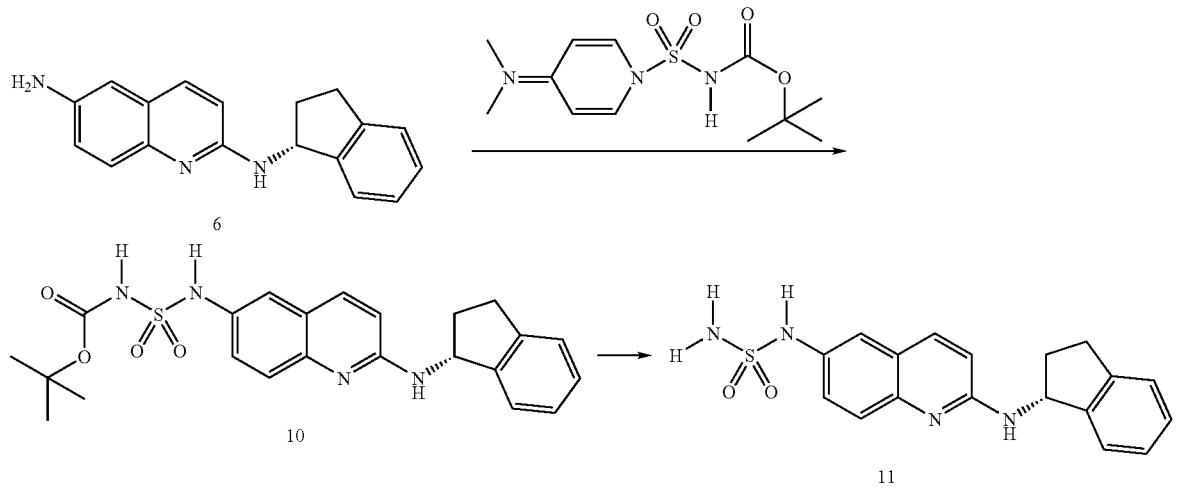

Amino-2-indanoyl-quinoline 6 is treated with dimethylamino pyridinium N-tert butoxycarbonyl sulfamide and subsequently deprotected with HCl/Methanol to yield quinoline sulfamide 11.

Route 7 Described in Example 76

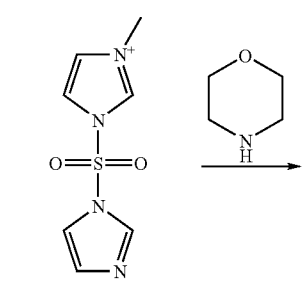

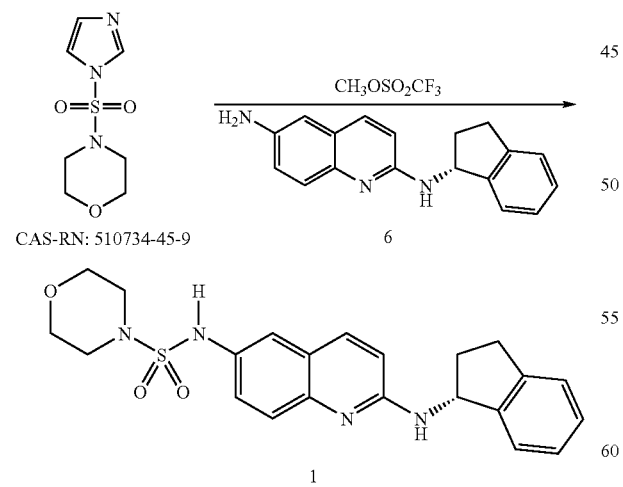

1H-Imidazolium, 3-(1H-imidazol-1-ylsulfonyl)-1-methyl-, trifluoromethanesulfonate (1:1) is treated with morpholine, then with methyl triflate and subsequently with amino-2-indanoyl-quinoline 6 to yield morpholino sulfamide 12.

Route 8 Described in Example 9

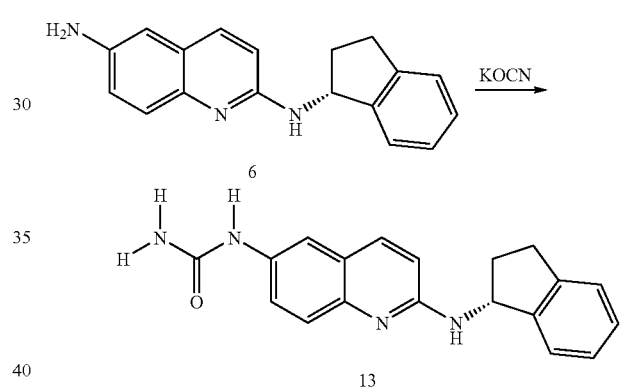

6-Amino-2-indanoyl-quinoline 6 is treated with potassium isocyanate in a mixture of acetic acid and water to yield urea derivative 13.

Route 9 Described in Example 116

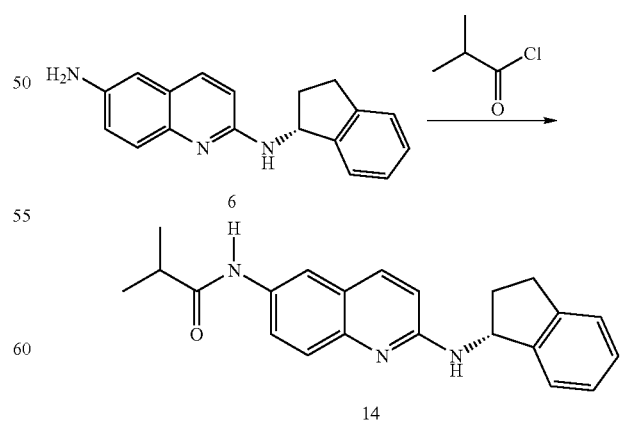

6-Amino-2-indanoyl-quinoline 6 is treated with isobutyryl chloride in triethyl amine and toluene to yield carboxamide derivative 14.

Route 10 Described in Examples 122 and 123

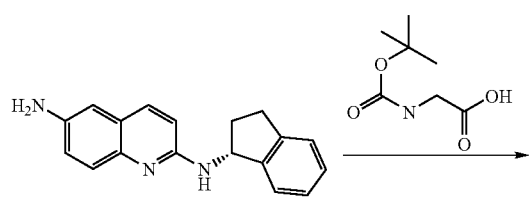

6

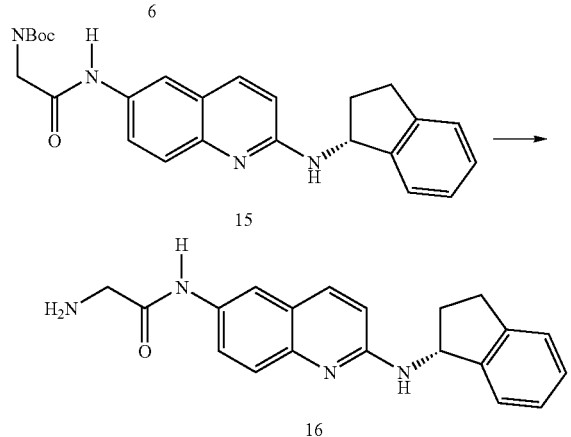

15

16

6-Amino-2-indanoyl-quinoline 6 is treated with N-Boc-glycine and 1-hydroxybenzotriazole/1-(3-dimethylamino-propyl)-3-ethylcarbodiimide hydrochloride in tetrahydrofuran and subsequently intermediate 15 deprotected with trifluoroacetic acid in dichloromethane to yield carboxamide 16.

Route 11 Described in Example 138

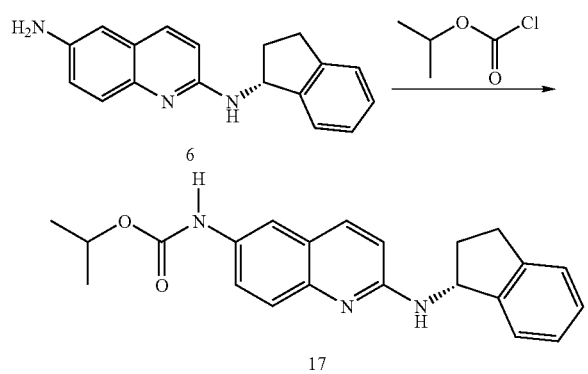

6

17

6-Amino-2-indanoyl-quinoline 6 is treated with isopropyl chloroformate in toluene and triethyl amine to yield carbamate derivative 17.

Route 12 Described in Example 166

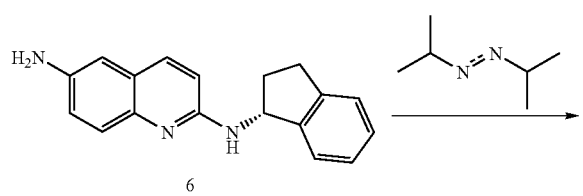

6

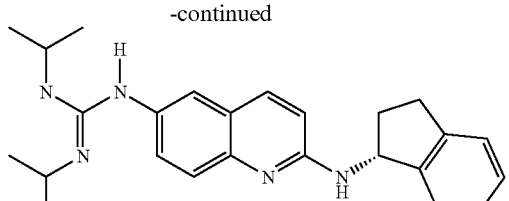

18

6-Amino-2-indanoyl-quinoline 6 is treated with N,N diisopropyl carbodiimide in toluene to yield guanidine derivative 18.

Route 13 Described in Example 149

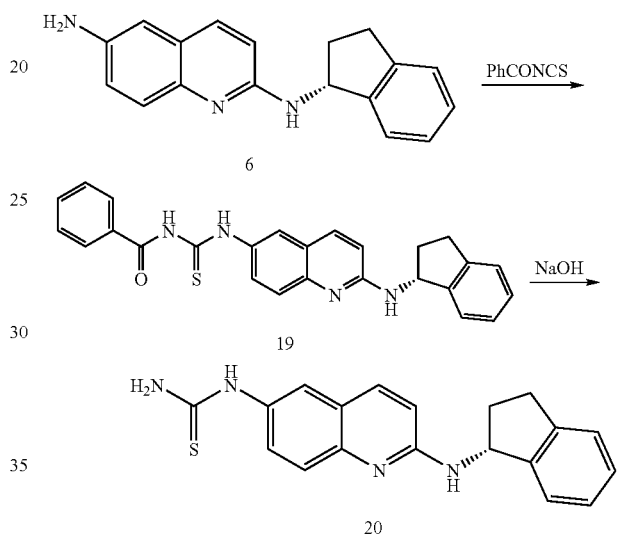

6-Amino-2-indanoyl-quinoline 6 is treated with benzoyl-isothiocyanate to yield the intermediate 19 which is hydrolyzed with sodium hydroxide to the thiourea 20.

Route 14 Described in Example 119

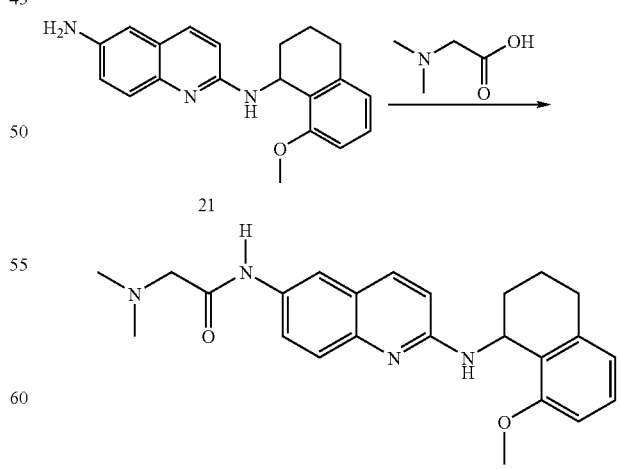

21

22 rac-$N^2$-(8-Methoxy-1,2,3,4-tetrahydro-naphthalen-1-yl)-quinoline-2,6-diamine 21 is treated with N,N-dimethylglycine, N,N-diisopropyl ethyl amine and 2-(1H-benzotriazole-1-yl)-1,1,3,3-tetramethyluronium tetrafluoroborate to yield carboxamide derivative 22.

Route 15 Described in Example 150

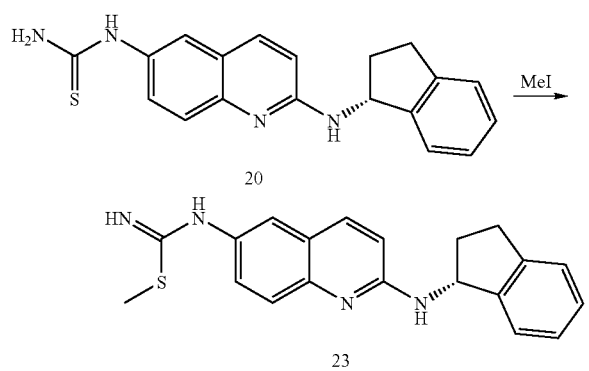

Thiourea 20 is treated with methyl iodide to yield 1-[2-((R)-indan-1-ylamino)-quinolin-6-yl]-2-methyl-isothiourea hydroiodide 23.

Route 16 Described in Example 151

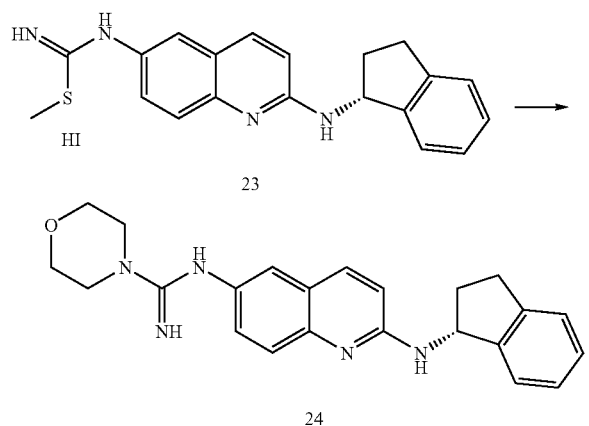

Thiourea 23 is treated with morpholine to yield the guanidine 24.

Route 17 Described in Example 163

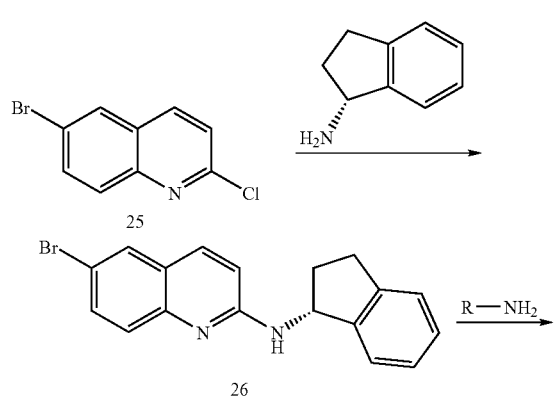

-continued

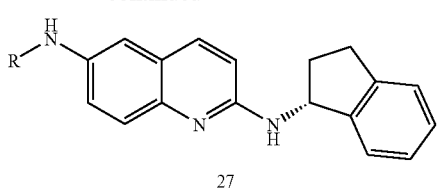

Commercially available 6-bromo-2-chloro-quinoline (25) is heated with commercially available (R)-1-aminoindane to yield intermediate 26 which is subsequently cross-coupled with amines under palladium-catalyzed conditions to the final products 27.

Route 18 Described in Examples 108, 109 and 114

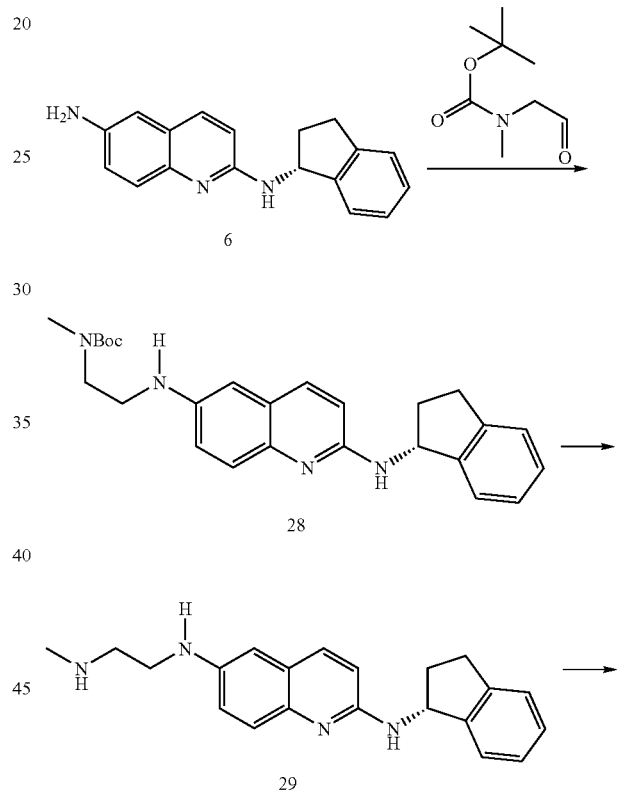

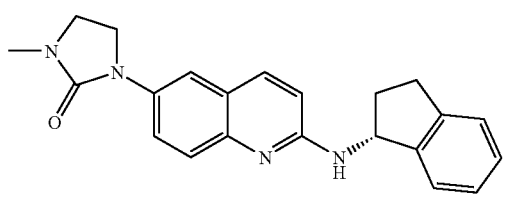

6-Amino-2-indanoyl-quinoline 6 is reductively aminated with methyl-(2-oxo-ethyl)carbamic acid tert-butyl ester by treatment with sodium cyanoborohydride, subsequently intermediate 28 is deprotected with trifluoroacetic acid in dichloromethane to yield amine 29, which is cyclized to the urea 30.

Route 19 Described in Examples 213

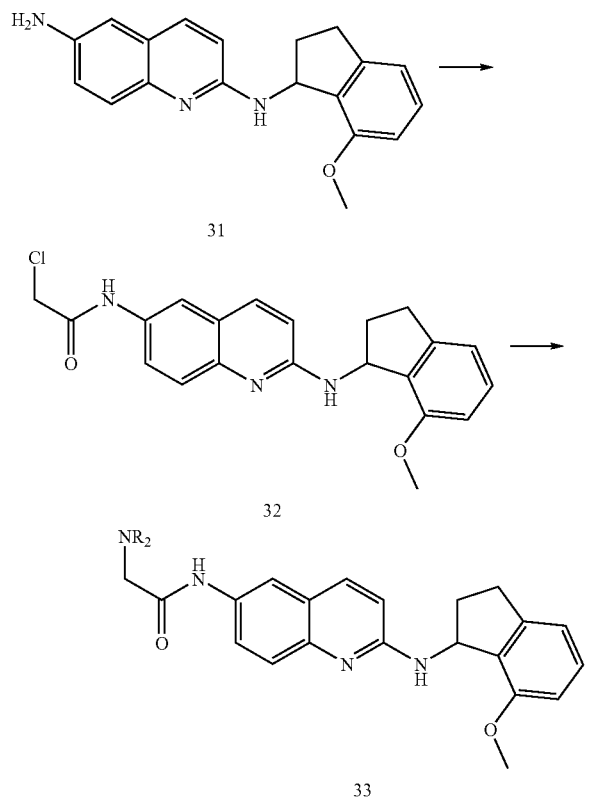

N-2-(7-methoxy-indan-1-yl)-quinoline-2,6-diamine 31 is reacted with chloroacetyl chloride to the chloride 32. Treatment with an amine $HNR_2$ leads to compound 33.

EXAMPLES

Example 1

$N^6$-(3-Dimethylamino-propyl)-$N^2$—(R)-indan-1-yl-quinoline-2,6-diamine

Step A: 2,6-Dichloroquinoline (5.0 g, 25 mmol) and R-(−)-1-aminoindane (6.725 g, 50 mmol) were heated at 125° C. for 20 h. The reaction mixture was purified by flash chromatography on silica gel (heptane/ethyl acetate 100:0→70:30 gradient). (6-Chloro-quinolin-2-yl)-(R)-indan-1-yl-amine was obtained as a light red solid (2.25 g, 30%), MS: m/e=296.8 (M+H$^+$).

Step B: (6-Chloro-quinolin-2-yl)-(R)-indan-1-yl-amine (200 mg, 0.75 mmol) was dissolved in 2.5 mL toluene. Argon was bubbled through the solution for 2 minutes to remove oxygen. N,N-dimethyl-1,3-propanediamine (0.26 mL, 1.53 mmol), sodium tert.-butylate (157 mg, 2.4 mmol), palladium acetate (15 mg) and 2-dicyclohexylphosphino-2',4',6'-triisopropylbiphenyl (X-PHOS) (49 mg, 0.05 mmol) were added. The reaction mixture was stirred in a sealed tube at 125° C. for 20 h. The solvent was evaporated and the residue purified by flash chromatography on silica gel (ethyl acetate/heptane 50:50→100:0 gradient). The title compound was obtained as a yellow solid (15 mg, 6%), MS: m/e=361.1 (M+H$^+$).

Example 2

(R)—$N^2$-Indan-1-yl-quinoline-2,6-diamine

Step A: 2-Chloro-6-nitro-quinoline (2.0 g, 10 mmol) and R-(−)-1-aminoindane (3.19 g, 24 mmol) were heated at 130° C. for 24 h. The reaction mixture was purified by flash chromatography on silica gel (dichloromethane). (R)-Indan-1-yl-(6-nitro-quinolin-2-yl)-amine was obtained as a yellow solid (2.0 g, 68%), MS: m/e=306.8 (M+H$^+$).

Step B: (R)-Indan-1-yl-(6-nitro-quinolin-2-yl)-amine (1.5 g, 5.0 mmol) were dissolved in ethyl acetate (60 mL). Upon addition of palladium on carbon (10%) the reaction mixture was stirred for 2 h at ambient temperature under an atmosphere of hydrogen. Then the catalyst was filtered off, the filter washed with ethyl acetate and the filtrate evaporated. (R)—$N^2$-Indan-1-yl-quinoline-2,6-diamine was obtained as a yellow foam (1.3 g, 96%); MS: m/e=276.4 (M+H$^+$).

Example 3

1-[2-((R)-Indan-1-ylamino)-quinolin-6-yl]-3-isopropyl-urea (R)—$N^2$-Indan-1-yl-quinoline-2,6-diamine (0.30 g, 1.09 mmol) was dissolved in toluene (5 mL). Isopropyl isocyanate (0.93 g, 1.09 mmol) was added and the reaction mixture was stirred at 60° C. for 2 h. Upon cooling to room temperature a precipitation formed which was filtered off and washed twice with dichloromethane. After drying the title compound was obtained as a white solid (330 mg, 85%); MS: m/e=276.4 (M+H$^+$).

Example 4

$N^6$-Allyl-$N^2$—(R)-indan-1-yl-quinoline-2,6-diamine

Step A: (R)-Indan-1-yl-(6-iodo-quinolin-2-yl)-amine, MS: m/e=387.0 (M+H$^+$), was prepared in accordance with the general method step A of example 1 from 2-chloro-6-iodoquinoline and R-(−)-1-aminoindane.

Step B: The title compound, MS: m/e=316.3 (M+H$^+$), was prepared according to step B of the general method of example 1 from (R)-indan-1-yl-(6-iodo-quinolin-2-yl)-amine.

Example 5

1-Cyclohexyl-3-[2-((R)-indan-1-ylamino)-quinolin-6-yl]-urea

Cyclohexyl-3-[2-((R)-indan-1-ylamino)-quinolin-6-yl]-urea, MS: m/e=401.5 (M+H$^+$), was prepared in accordance with the general method of example 3 from cyclohexyl isocyanate and (R)—$N^2$-indan-1-yl-quinoline-2,6-diamine.

Example 6

1-[2-((R)-Indan-1-ylamino)-quinolin-6-yl]-3-((1S,2R)-2-phenyl-cyclopropyl)-urea

1-[2-((R)-Indan-1-ylamino)-quinolin-6-yl]-3-((1S,2R)-2-phenyl-cyclopropyl)-urea, MS: m/e=435.5 (M+H$^+$), was prepared in accordance with the general method of example 3 from trans-2-phenylcyclopropyl isocyanate and (R)—$N^2$-indan-1-yl-quinoline-2,6-diamine.

Example 7

1-[2-((R)-Indan-1-ylamino)-quinolin-6-yl]-3-methyl-urea

1-[2-((R)-Indan-1-ylamino)-quinolin-6-yl]-3-methyl-urea, MS: m/e=332.4 (M+H$^+$), was prepared in accordance with the general method of example 3 from methyl isocyanate and (R)—N$^2$-indan-1-yl-quinoline-2,6-diamine.

Example 8

1-tert-Butyl-3-[2-((R)-indan-1-ylamino)-quinolin-6-yl]-urea tert-Butyl-3-[2-((R)-indan-1-ylamino)-quinolin-6-yl]-urea, MS: m/e=375.4 (M+H$^+$), was prepared in accordance with the general method of example 3 from tert. butyl isocyanate and (R)—N$^2$-indan-1-yl-quinoline-2,6-diamine.

Example 9

[2-((R)-Indan-1-ylamino)-quinolin-6-yl]-urea (R)—N$^2$-indan-1-yl-quinoline-2,6-diamine (100 mg, 0.36 mmol) and potassium isocyanate (32 mg, 0.40 mmol) were stirred in a 1:1 mixture of water and acetic acid (3 mL) at ambient temperature for 2 h. Then a satured solution of sodium bicarbonate was added, the aqueous phase was extracted with ethyl acetate, the organic phase washed with brine and dried over sodium sulfate. Over night the desired product precipitated and subsequently the crystals were collected and dried under vacuum. [2-((R)-Indan-1-ylamino)-quinolin-6-yl]-urea was obtained as a white solid (44 mg; 38%); MS: m/e=319.3 (M+H$^+$).

Example 10 rac-1-[2-(2,3-Dihydro-benzofuran-3-ylamino)-quinolin-6-yl]-3-isopropyl-urea

Step A: (2,3-Dihydro-benzofuran-3-yl)-(6-nitro-quinolin-2-yl)-amine was prepared according to step A in general example 2 from 2-chloro-6-nitro-quinoline and 2,3-dihydro-benzofuran-3-ylamine (CAS no.: 109926-23-4); MS: m/e=308.3 (M+H$^+$).

Step B: N$^2$-(2,3-Dihydro-benzofuran-3-yl)-quinoline-2,6-diamine was prepared according to step B in general example 2 from (2,3-Dihydro-benzofuran-3-yl)-(6-nitro-quinolin-2-yl)-amine; MS: m/e=277.3 (M+H$^+$).

Step C: The title compound was prepared in accordance with the general method described in example 3 from isopropyl isocyanate and N$^2$-(2,3-dihydro-benzofuran-3-yl)-quinoline-2,6-diamine; MS: m/e=363.3 (M+H$^+$).

Example 11

(+)-1-{2-[-(2,3-Dihydro-benzofuran-3-yl)amino]-quinolin-6-yl}-3-isopropyl-urea rac-1-[2-(2,3-Dihydro-benzofuran-3-ylamino)-quinolin-6-yl]-3-isopropyl-urea was separated on chiral preparative HPLC using 15% ethanol in heptane.

Example 12 rac-1-Isopropyl-3-[2-(7-methoxy-indan-1-ylamino)-quinolin-6-yl]-urea

The title compound was prepared in accordance with the general method described in example 3 from isopropyl isocyanate and rac-N$^2$-(7-methoxy-indan-1-yl)-quinoline-2,6-diamine (Example 172); MS: m/e=391.5 (M+H$^+$).

Example 13

(−)-1-Isopropyl-3-[2-(7-methoxy-indan-1-ylamino)-quinolin-6-yl]-urea rac-1-Isopropyl-3-[2-(7-methoxy-indan-1-ylamino)-quinolin-6-yl]-urea was separated on chiral preparative HPLC using 20% ethanol in heptane.

Example 14 rac-N$^2$-(8-Methoxy-1,2,3,4-tetrahydro-naphthalen-1-yl)-quinoline-2,6-diamine The title compound was prepared in accordance with the general method described in example 2 from 2-chloro-6-nitro-quinoline and rac-8-methoxy-1,2,3,4-tetrahydronaphthalen-1-amine (CAS no. 535935-61-6); MS: m/e=320.3 (M+H$^+$).

Example 15 rac-1-Isopropyl-3-[2-(8-methoxy-1,2,3,4-tetrahydro-naphthalen-1-ylamino)-quinolin-6-yl]-urea The title compound was prepared in accordance with the general method described in example 3 from rac-N$^2$-(8-methoxy-1,2,3,4-tetrahydro-naphthalen-1-yl)-quinoline-2,6-diamine and isopropyl isocyanate; MS: m/e=405.5 (M+H$^+$).

Example 16

4-Methyl-piperazine-1-carboxylic acid [2-((R)-indan-1-ylamino)-quinolin-6-yl]-amide (R)—N$^2$-Indan-1-yl-quinoline-2,6-diamine (0.25 g, 0.9 mmol) was dissolved in tetrahydrofuran (10 mL) and triethylamine (0.138 mL, 1.0 mmol) was added. At 0° C. triphosgene (121 mg, 0.4 mmol) was added and the reaction mixture subsequently heated to 80° C. for 3 h. Upon cooling to ambient temperature triethylamine (0.138 mL, 1.0 mmol) and 1-methyl-piperazine (0.1 mL, 0.9 mmol) were added and the whole reaction mixture was stirred over night at 50° C. After evaporation of the solvent, the residue was taken up in water and extracted with ethyl acetate. The combined organic phases were dried on sodium sulfate, filtered and the filtrate was evaporated. The residue was taken up in a small amount of ethyl acetate, sonicated and kept over night in a refrigerator whereby a crystalline precipitate formed. The precipitate was isolated and dried on vacuum to yield the title compound (190 mg; 52%) as an off-white solid; MS: m/e=402.6 (M+H$^+$).

Example 17

1-[2-((R)-Indan-1-ylamino)-quinolin-6-yl]-3-(2-methoxy-ethyl)-urea

The title compound was prepared in accordance with the general method 4 described in example 16 from bis(trichloromethyl) carbonate, 2-methoxyethylamine and (R)—N²-indan-1-yl-quinoline-2,6-diamine; MS: m/e=377.5 (M+H⁺).

Example 18

1-(2-Dimethylamino-ethyl)-3-[2-((R)-indan-1-ylamino)-quinolin-6-yl]-urea

The title compound was prepared in accordance with the general method 4 described in example 16 from bis(trichloromethyl) carbonate, 2-dimethylamino-ethylamine and (R)—N²-indan-1-yl-quinoline-2,6-diamine; MS: m/e=390.5 (M+H⁺).

Example 19

1-[2-((R)-Indan-1-ylamino)-quinolin-6-yl]-3-(tetrahydro-pyran-4-yl)-urea

The title compound was prepared in accordance with the general method 4 described in example 16 from bis(trichloromethyl) carbonate, 4-aminotetrahydropyran and (R)—N²-indan-1-yl-quinoline-2,6-diamine; MS: m/e=403.5 (M+H⁺).

Example 20

1-[2-((R)-Indan-1-ylamino)-quinolin-6-yl]-3-(1-methyl-piperidin-4-yl)-urea

The title compound was prepared in accordance with the general method 4 described in example 16 from bis(trichloromethyl) carbonate, 1-methyl-piperidin-4-ylamine and (R)—N²-indan-1-yl-quinoline-2,6-diamine; MS: m/e=415.5 (M+H⁺).

Example 21

1-Cyclopropyl-3-[2-((R)-indan-1-ylamino)-quinolin-6-yl]-urea

The title compound was prepared in accordance with the general method 4 described in example 16 from bis(trichloromethyl) carbonate, cyclopropylamine and (R)—N²-indan-1-yl-quinoline-2,6-diamine; MS: m/e=359.5 (M+H⁺).

Example 22

Morpholine-4-carboxylic acid [2-((R)-indan-1-ylamino)-quinolin-6-yl]-amide

The title compound was prepared in accordance with the general method 4 described in example 16 from bis(trichloromethyl) carbonate, morpholine and (R)—N²-indan-1-yl-quinoline-2,6-diamine; MS: m/e=389.5 (M+H⁺).

Example 23

1-Cyclopropylmethyl-3-[2-((R)-indan-1-ylamino)-quinolin-6-yl]-urea

The title compound was prepared in accordance with the general method 4 described in example 16 from bis(trichloromethyl) carbonate, aminomethyl cyclopropane and (R)—N²-indan-1-yl-quinoline-2,6-diamine; MS: m/e=373.5 (M+H⁺).

Example 24

Thiomorpholine-4-carboxylic acid [2-((R)-indan-1-ylamino)-quinolin-6-yl]-amide

The title compound was prepared in accordance with the general method 4 described in example 16 from bis(trichloromethyl) carbonate, thiomorpholine and (R)—N²-indan-1-yl-quinoline-2,6-diamine; MS: m/e=405.5 (M+H⁺).

Example 25

1-(1-Benzyl-pyrrolidin-3-yl)-3-[2-((R)-indan-1-ylamino)-quinolin-6-yl]-urea

The title compound was prepared in accordance with the general method 4 described in example 16 from bis(trichloromethyl) carbonate, rac-1-benzyl-3-aminopyrrolidine and (R)—N²-indan-1-yl-quinoline-2,6-diamine; MS: m/e=478.6 (M+H⁺).

Example 26

1-Bicyclo[2.2.1]hept-2-yl-3-[2-((R)-indan-1-ylamino)-quinolin-6-yl]-urea

The title compound was prepared in accordance with the general method 4 described in example 16 from bis(trichloromethyl) carbonate, rac-exo-2-aminonorbornane and (R)—N²-indan-1-yl-quinoline-2,6-diamine; MS: m/e=413.6 (M+H⁺).

Example 27

1-(1,1-Dioxo-tetrahydro-thiophen-3-yl)-3-[2-((R)-indan-1-ylamino)-quinolin-6-yl]-urea The title compound was prepared in accordance with the general method 4 described in example 16 from bis(trichloromethyl) carbonate, rac-1,1-dioxo-tetrahydro-1-6-thiophen-3-ylamine and (R)—N²-indan-1-yl-quinoline-2,6-diamine; MS: m/e=437.6 (M+H⁺).

Example 28

1-Ethyl-1-(4-hydroxy-cyclohexyl)-3-[2-((R)-indan-1-ylamino)-quinolin-6-yl]-urea

The title compound was prepared in accordance with the general method 4 described in example 16 from bis(trichloromethyl) carbonate, 4-ethylamino-cyclohexanol and (R)—N²-indan-1-yl-quinoline-2,6-diamine; MS: m/e=445.7 (M+H⁺).

Example 29

1-[2-((R)-Indan-1-ylamino)-quinolin-6-yl]-3-(2-morpholin-4-yl-ethyl)-urea

The title compound was prepared in accordance with the general method 4 described in example 16 from bis(trichloromethyl) carbonate, 2-morpholin-4-yl-ethylamine and (R)—N²-indan-1-yl-quinoline-2,6-diamine; MS: m/e=432.6 (M+H⁺).

Example 30

4-Hydroxy-4-methyl-piperidine-1-carboxylic acid [2-((R)-indan-1-ylamino)-quinolin-6-yl]-amide The title compound was prepared in accordance with the general method 4 described in example 16 from bis(trichloromethyl) carbonate, 4-methyl-piperidin-4-ol and (R)—N²-indan-1-yl-quinoline-2,6-diamine; MS: m/e=417.6 (M+H⁺).

Example 31

2-Oxa-8-aza-spiro[4.5]decane-8-carboxylic acid [2-((R)-indan-1-ylamino)-quinolin-6-yl]-amide The title compound was prepared in accordance with the general method 4 described in example 16 from bis(trichloromethyl) carbonate, 2-(3-ethyl-tetrahydro-furan-3-yl)-ethylamine and (R)—N²-indan-1-yl-quinoline-2,6-diamine; MS: m/e=443.7 (M+H⁺).

Example 32

1-[2-(Cyclopropyl-methyl-amino)-ethyl]-3-[2-((R)-indan-1-ylamino)-quinolin-6-yl]-urea The title compound was prepared in accordance with the general method 4 described in example 16 from bis(trichloromethyl) carbonate, N(1)-cyclopropyl-N(1)-methyl-ethane-1,2-diamine and (R)—N²-indan-1-yl-quinoline-2,6-diamine; MS: m/e=416.6 (M+H⁺).

Example 33

(1S,4S)-2-Oxa-5-aza-bicyclo[2.2.1]heptane-5-carboxylic acid [2-((R)-indan-1-ylamino)-quinolin-6-yl]-amide The title compound was prepared in accordance with the general method 4 described in example 16 from bis(trichloromethyl) carbonate, (1S,4S)-2-oxa-5-aza-bicyclo[2.2.1]heptane and (R)—N²-indan-1-yl-quinoline-2,6-diamine; MS: m/e=401.6 (M+H⁺).

Example 34

(1R,5S)-8-Oxa-3-aza-bicyclo[3.2.1]octane-3-carboxylic acid [2-((R)-indan-1-ylamino)-quinolin-6-yl]-amide The title compound was prepared in accordance with the general method 4 described in example 16 from bis(trichloromethyl) carbonate, 8-oxa-3-aza-bicyclo[3.2.1]octane and (R)—N²-indan-1-yl-quinoline-2,6-diamine; MS: m/e=415.6 (M+H⁺).

Example 35 rac-1-[2-(2,3-Dihydro-benzofuran-3-ylamino)-quinolin-6-yl]-3-(1-methyl-piperidin-4-yl)-urea The title compound was prepared in accordance with the general method 4 described in example 16 from bis(trichloromethyl) carbonate, 1-methyl-piperidin-4-ylamine and rac-N²-(2,3-dihydro-benzofuran-3-yl)-quinoline-2,6-diamine; MS: m/e=418.6 (M+H⁺).

Example 36

1-[2-((R)-Indan-1-ylamino)-quinolin-6-yl]-3-[2-(tetrahydro-pyran-2-yloxy)-ethyl]-urea The title compound was prepared in accordance with the general method 4 described in example 16 from bis(trichloromethyl) carbonate, 2-(tetrahydro-pyran-2-yloxy)-ethylamine and (R)—N²-indan-1-yl-quinoline-2,6-diamine; MS: m/e=446.6 (M+H⁺).

Example 37

4-Hydroxymethyl-piperidine-1-carboxylic acid [2-((R)-indan-1-ylamino)-quinolin-6-yl]-amide Step A: 4-(Tetrahydro-pyran-2-yloxymethyl)-piperidine-1-carboxylic acid [2-((R)-indan-1-ylamino)-quinolin-6-yl]-amide, MS: m/e=501.7 (M+H⁺), was prepared according to general method 4 described in example 16 from bis(trichloromethyl) carbonate, 4-(tetrahydro-pyran-2-ylmethoxy)-piperidine and (R)—N²-indan-1-yl-quinoline-2,6-diamine.

Step B: 4-(Tetrahydro-pyran-2-yloxymethyl)-piperidine-1-carboxylic acid [2-((R)-indan-1-ylamino)-quinolin-6-yl]-amide (0.070 g) was dissolved in methanol (1 mL). Pyridinium toluene-4-sulfonate (11.0 mg) was added and the reaction mixture stirred at 55° C. for 1 h. The reaction mixtures was diluted with water and extracted with ethyl acetate. The combined organic phases were dried on sodium sulfate, evaporated and the residue was subjected to column chromatography (silica gel, dichloro methane:methanol gradient=100:0→90:10) to yield the title compound (35 mg; 60%) as an off-white solid; MS: m/e=416.7 (M+H⁺).

Example 38

4-{3-[2-((R)-Indan-1-ylamino)-quinolin-6-yl]-ureido}-piperidine-1-carboxylic acid tert-butyl ester The title compound was prepared in accordance with the general method 4 described in example 16 from bis(trichloromethyl) carbonate, 4-amino-1-tert-butyloxycarbonyl-piperidine and (R)—N²-indan-1-yl-quinoline-2,6-diamine; MS: m/e=502.6 (M+H⁺).

Example 39

1-[2-((R)-Indan-1-ylamino)-quinolin-6-yl]-3-piperidin-4-yl-urea

4-{3-[2-((R)-Indan-1-ylamino)-quinolin-6-yl]-ureido}-piperidine-1-carboxylic acid tert-butyl ester (20 mg, 0.040 mmol) was dissolved in methylene chloride (1.0 mL). At 0° C. trifluoroacetic acid (0.030 mL, 0.40 mmol) was added and the reaction mixture was stirred at ambient temperature over night. 20% sodium carbonate solution in water was added and the mixture was extracted with ethyl acetate (3×10 mL). The combined organic phases were dried on magnesium sulfate, filtered and evaporated. The residue was subjected to column chromatography (silica gel, methylene chloride:methanol gradient=95:5→2:1) to yield the title compound (5.0 mg; 31%) as an off-white solid; MS: m/e=402.5 (M+H⁺).

Example 40 rac-1-[2-(7-Methoxy-indan-1-ylamino)-quinolin-6-yl]-3-(1-methyl-piperidin-4-yl)-urea The title compound was prepared in accordance with the general method 4 described in example 16 from bis(trichloromethyl) carbonate, 1-methyl-piperidin-4-ylamine and rac-$N^2$-(7-methoxy-indan-1-yl)-quinoline-2,6-diamine (Example 172); MS: m/e=446.7 (M+H$^+$).

Example 41

1-(1-Cyclopropyl-piperidin-4-yl)-3-[2-((R)-indan-1-ylamino)-quinolin-6-yl]-urea

The title compound was prepared in accordance with the general method 4 described in example 16 from bis(trichloromethyl) carbonate, 1-cyclopropyl-piperidin-4-ylamine and (R)—$N^2$-indan-1-yl-quinoline-2,6-diamine; MS: m/e=442.7 (M+H$^+$).

Example 42

1-[2-((R)-Indan-1-ylamino)-quinolin-6-yl]-3-(1-isopropyl-piperidin-4-yl)-urea

The title compound was prepared in accordance with the general method 4 described in example 16 from bis(trichloromethyl) carbonate, 1-isopropyl-piperidin-4-ylamine (CAS no. 127285-08-9) and (R)—$N^2$-indan-1-yl-quinoline-2,6-diamine; MS: m/e=444.7 (M+H$^+$).

Example 43

1-[2-((R)-Indan-1-ylamino)-quinolin-6-yl]-3-[1-(2-methoxy-ethyl)-piperidin-4-yl]-urea The title compound was prepared in accordance with the general method 4 described in example 16 from bis(trichloromethyl) carbonate, 1-(2-methoxy-ethyl)-piperidin-4-ylamine and (R)—$N^2$-indan-1-yl-quinoline-2,6-diamine; MS: m/e=460.7 (M+H$^+$).

Example 44 rac-1-(1-Isopropyl-piperidin-4-yl)-3-[2-(7-methoxy-indan-1-ylamino)-quinolin-6-yl]-urea The title compound was prepared in accordance with the general method 4 described in example 16 from bis(trichloromethyl) carbonate, 1-isopropyl-piperidin-4-ylamine (CAS no. 127285-08-9) and rac-$N^2$-(7-methoxy-indan-1-yl)-quinoline-2,6-diamine (Example 172); MS: m/e=474.7 (M+H$^+$).

Example 45 rac-1-[1-(2-Methoxy-ethyl)-piperidin-4-yl]-3-[2-(7-methoxy-indan-1-ylamino)-quinolin-6-yl]-urea The title compound was prepared in accordance with the general method 4 described in example 16 from bis(trichloromethyl) carbonate, 1-(2-methoxy-ethyl)-piperidin-4-ylamine and rac-$N^2$-(7-methoxy-indan-1-yl)-quinoline-2,6-diamine (Example 172); MS: m/e=490.7 (M+H$^+$).

Example 46 rac-1-[1-(2-Fluoro-ethyl)-piperidin-4-yl]-3-[2-(7-methoxy-indan-1-ylamino)-quinolin-6-yl]-urea The title compound was prepared in accordance with the general method 4 described in example 16 from bis(trichloromethyl) carbonate, 1-(2-fluoroethyl)-piperidin-4-ylamine and rac-$N^2$-(7-methoxy-indan-1-yl)-quinoline-2,6-diamine (Example 172); MS: m/e=478.7 (M+H$^+$).

Example 47 rac-1-[2-(7-Methoxy-indan-1-ylamino)-quinolin-6-yl]-3-[1-(3,3,3-trifluoro-propyl)-piperidin-4-yl]-urea The title compound was prepared in accordance with the general method 4 described in example 16 from bis(trichloromethyl) carbonate, 1-(3,3,3-trifluoro-propyl)-piperidin-4-ylamine and rac-$N^2$-(7-methoxy-indan-1-yl)-quinoline-2,6-diamine (Example 172); MS: m/e=528.8 (M+H$^+$).

Example 48

1-[2-((R)-Indan-1-ylamino)-quinolin-6-yl]-3-[1-(2-methylsulfanyl-ethyl)-piperidin-4-yl]-urea Step A: Piperidin-4-yl-carbamic acid tert-butyl ester (0.70 g, 3.0 mmol), triethylamine (1.46 mL, 10 mmol) and 2-chlorethyl-methylsulfide (0.39 g, 3.0 mmol) were dissolved in methanol (10 mL) and stirred for 16 h at 50° C. Then the solvent was removed and the residue subjected to column chromatography (silica gel, heptane:ethyl acetate gradient=1:1→0:1). [1-(2-Methylsulfanyl-ethyl)-piperidin-4-yl]-carbamic acid tert-butyl ester was obtained as a light yellow solid (0.46 g, 48%); MS: m/e=275.5 (M+H$^+$).

Step B: [1-(2-Methylsulfanyl-ethyl)-piperidin-4-yl]-carbamic acid tert-butyl ester (0.35 g, 1.0 mmol) was dissolved in HCl/Methanol (2.5M, 4 mL) and stirred for 1.5 h at 40° C. After evaporation of the solvent and drying under high vacuum, 1-(2-methylsulfanyl-ethyl)-piperidin-4-ylamine dihydrochloride was obtained as an off-white solid (0.22 g, 100%); MS: m/e=175.5 (M+H$^+$).

Step C: The title compound was prepared in accordance with the general method 4 described in example 16 from bis(trichloromethyl) carbonate, 1-(2-methylsulfanyl-ethyl)-piperidin-4-ylamine dihydrochloride and (R)—$N^2$-indan-1-yl-quinoline-2,6-diamine; MS: m/e=476.7 (M+H$^+$).

Example 49

1-[2-((R)-Indan-1-ylamino)-quinolin-6-yl]-3-((endo)-9-methyl-9-aza-bicyclo[3.3.1]non-3-yl)-urea The title compound was prepared in accordance with the general method 4 described in example 16 from bis(trichloromethyl) carbonate, endo-9-methyl-9-azabicyclo[3.3.1]nonan-3-amine and (R)—$N^2$-indan-1-yl-quinoline-2,6-diamine; MS: m/e=456.7 (M+H$^+$).

Example 50 rac-1-[2-(7-Methoxy-indan-1-ylamino)-quinolin-6-yl]-(9-methyl-9-aza-bicyclo[3.3.1]non-3-yl)-urea The title compound was prepared in accordance with the general method 4 described in example 16 from bis(trichloromethyl) carbonate, endo-9-methyl-9-azabicyclo[3.3.1]nonan-3-amine and rac-N$^2$-(7-methoxy-indan-1-yl)-quinoline-2,6-diamine (Example 172); MS: m/e=486.7 (M+H$^+$).

Example 51 rac-1-[2-(7-Methoxy-indan-1-ylamino)-quinolin-6-yl]-3-[1-(2-methylsulfanyl-ethyl)-piperidin-4-yl]-urea The title compound was prepared in accordance with the general method 4 described in example 16 from bis(trichloromethyl) carbonate, 1-(2-methylsulfanyl-ethyl)-piperidin-4-ylamine dihydrochloride and rac-N$^2$-(7-methoxy-indan-1-yl)-quinoline-2,6-diamine (Example 172); MS: m/e=506.8 (M+H$^+$).

Example 52 rac-1-[2-(7-Methoxy-indan-1-ylamino)-quinolin-6-yl]-3-[1-(3,3,3-trifluoro-propionyl)-piperidin-4-yl]-urea The title compound was prepared in accordance with the general method 4 described in example 16 from bis(trichloromethyl) carbonate, 1-(4-amino-piperidin-1-yl)-3,3,3-trifluoro-propan-1-one hydrochloride and rac-N$^2$-(7-methoxy-indan-1-yl)-quinoline-2,6-diamine (Example 172); MS: m/e=542.8 (M+H$^+$).

Example 53 rac-1-(1-Cyclopropyl-piperidin-4-yl)-3-[2-(7-methoxy-indan-1-ylamino)-quinolin-6-yl]-urea The title compound was prepared in accordance with the general method 4 described in example 16 from bis(trichloromethyl) carbonate, 1-cyclopropyl-piperidin-4-ylamine and rac-N$^2$-(7-methoxy-indan-1-yl)-quinoline-2,6-diamine (Example 172); MS: m/e=472.8 (M+H$^+$).

Example 54 rac-1-(1,1-Dioxo-hexahydro-thiopyran-4-yl)-3-[2-(8-methoxy-1,2,3,4-tetrahydro-naphthalen-1-ylamino)-quinolin-6-yl]-urea The title compound was prepared in accordance with the general method 4 described in example 16 from bis(trichloromethyl) carbonate, 1,1-dioxo-hexahydro-thiopyran-4-ylamine (CAS no. 210240-20-3) and rac-N$^2$-(8-methoxy-1,2,3,4-tetrahydro-naphthalen-1-yl)-quinoline-2,6-diamine; MS: m/e=495.4 (M+H$^+$).

Example 55 rac-1-(1-Cyclopropyl-piperidin-4-yl)-3-[2-(8-methoxy-1,2,3,4-tetrahydro-naphthalen-1-ylamino)-quinolin-6-yl]-urea The title compound was prepared in accordance with the general method 4 described in example 16 from bis(trichloromethyl) carbonate, 4-amino-1-cyclopropylpiperidine (CAS no. 62813-02-9) and rac-N$^2$-(8-methoxy-1,2,3,4-tetrahydro-naphthalen-1-yl)-quinoline-2,6-diamine MS: m/e=486.1 (M+H$^+$).

Example 56 rac-1-[2-(8-Methoxy-1,2,3,4-tetrahydro-naphthalen-1-ylamino)-quinolin-6-yl]-3-endo-(9-methyl-9-azabicyclo[3.3.1]non-3-yl)-urea The title compound was prepared in accordance with the general method 4 described in example 16 from bis(trichloromethyl) carbonate, endo-9-methyl-azabicyclo[3.3.1]nonan-3-amine and rac-N$^2$-(8-methoxy-1,2,3,4-tetrahydro-naphthalen-1-yl)-quinoline-2,6-diamine; MS: m/e=500.3 (M+H$^+$).

Example 57 rac-1-[2-(8-Methoxy-1,2,3,4-tetrahydro-naphthalen-1-ylamino)-quinolin-6-yl]-3-(1-methyl-piperidin-4-yl)-urea The title compound was prepared in accordance with the general method 4 described in example 16 from bis(trichloromethyl) carbonate, 4-amino-1-methylylpiperidine and rac-N$^2$-(8-methoxy-1,2,3,4-tetrahydro-naphthalen-1-yl)-quinoline-2,6-diamine; MS: m/e=460.5 (M+H$^+$).

Example 58 rac-1-[1-(2-Methoxy-ethyl)-piperidin-4-yl]-3-[2-(8-methoxy-1,2,3,4-tetrahydro-naphthalen-1-ylamino)-quinolin-6-yl]-urea The title compound was prepared in accordance with the general method 4 described in example 16 from bis(trichloromethyl) carbonate, 1-(2-methoxy-ethyl)-piperidin-4-ylamine and rac-N$^2$-(8-methoxy-1,2,3,4-tetrahydro-naphthalen-1-yl)-quinoline-2,6-diamine; MS: m/e=504.5 (M+H$^+$).

Example 59 rac-1-[1-(2-Fluoro-ethyl)-piperidin-4-yl]-3-[2-(8-methoxy-1,2,3,4-tetrahydro-naphthalen-1-ylamino)-quinolin-6-yl]-urea The title compound was prepared in accordance with the general method 4 described in example 16 from bis(trichloromethyl) carbonate, 1-(2-fluoroethyl)-piperidin-4-ylamine and rac-N$^2$-(8-methoxy-1,2,3,4-tetrahydro-naphthalen-1-yl)-quinoline-2,6-diamine; MS: m/e=492.5 (M+H$^+$).

Example 60 rac-endo-1-[2-(8-Methoxy-1,2,3,4-tetrahydro-naphthalen-1-ylamino)-quinolin-6-yl]-3-(8-methyl-8-azabicyclo[3.2.1]oct-3-yl)-urea The title compound was prepared in accordance with the general method 4 described in example 16 from bis(trichloromethyl) carbonate, endo-8-methyl-8-azabicyclo[3.2.1]octan-3-amine and rac-N$^2$-(8-methoxy-1,2,3,4-tetrahydro-naphthalen-1-yl)-quinoline-2,6-diamine; MS: m/e=486.5 (M+H$^+$).

Example 61

1-[1-(2-Fluoro-acetyl)-piperidin-4-yl]-3-[2-((R)-indan-1-ylamino)-quinolin-6-yl]-urea The title compound was prepared in accordance with the general method 4 described in example 16 from bis(trichloromethyl) carbonate, 1-(4-amino-piperidin-1-yl)-2-fluoro-ethanone hydrochloride and (R)—N$^2$-indan-1-yl-quinoline-2,6-diamine; MS: m/e=462.6 (M+H$^+$).

Example 62

1-[2-((R)-Indan-1-ylamino)-quinolin-6-yl]-3-[1-(3,3,3-trifluoro-propionyl)-piperidin-4-yl]-urea The title compound was prepared in accordance with the general method 4 described in example 16 from bis(trichloromethyl) carbonate, 1-(4-amino-piperidin-1-yl)-3,3,3-trifluoro-propan-1-one hydrochloride and (R)—N$^2$-indan-1-yl-quinoline-2,6-diamine; MS: m/e=512.6 (M+H$^+$).

Example 63

1-[2-((R)-Indan-1-ylamino)-quinolin-6-yl]-3-[1-(3,3,3-trifluoro-propyl)-piperidin-4-yl]-urea The title compound was prepared in accordance with the general method 4 described in example 16 from bis(trichloromethyl) carbonate, 1-(4-amino-piperidin-1-yl)-3,3,3-trifluoro-propan hydrochloride and (R)—N$^2$-indan-1-yl-quinoline-2,6-diamine; MS: m/e=498.6 (M+H$^+$).

Example 64

1-[2-(8-Methoxy-1,2,3,4-tetrahydro-naphthalen-1-ylamino)-quinolin-6-yl]-3-((S)-1-methyl-pyrrolidin-3-yl)-urea The title compound was prepared in accordance with the general method 4 described in example 16 from bis(trichloromethyl) carbonate, (3S)-1-methyl-3-pyrrolidinamine (CAS no. 214357-95-6) and rac-N$^2$-(8-methoxy-1,2,3,4-tetrahydro-naphthalen-1-yl)-quinoline-2,6-diamine; MS: m/e=446.2 (M+H$^+$).

Example 65 rac-1-[2-(4,6-Dichloro-7-methoxy-indan-1-ylamino)-quinolin-6-yl]-3-isopropyl-urea Step A: Rac-7-methoxy-indan-1-ylamine hydrochloride (2.20 g, 0.011 mmol) was dissolved in acetic acid (100 mL). After cooling to 0° C. sulfuryl chloride (1.88 mL, 0.23 mmol) was slowly added and the reaction mixture was stirred for 16 h at ambient temperature. Then the solvent was evaporated and the residue was taken up in isopropanol. Thereby a precipitate formed which was isolated and dried on high vacuum to yield rac-4,6-dichloro-7-methoxy-indan-1-ylamine (2.0 g, 68%) as a white solid; MS: m/e=269.6 (M+H$^+$).
Step B: Rac-(4,6-dichloro-7-methoxy-indan-1-yl)-(6-nitro-quinolin-2-yl)-amine was obtained according to the method described in step A of general example 2; MS: m/e=405.5 (M+H$^+$).
Step C: Rac-(4,6-dichloro-7-methoxy-indan-1-yl)-(6-nitro-quinolin-2-yl)-amine (250 mg, 0.62 mmol) were taken up in a mixture of ethanol (5 mL) and water (2.5 mL). After the addition of ammonium chloride (17 mg, 0.31 mmol) and iron powder (173 mg, 3.1 mmol) the reaction mixture was heated tom reflux for 6 h. After cooling to ambient temperature the reaction mixture was filtered through Dicalit®, the filtrate was concentrated and the residue was subjected to column chromatography (silica gel, heptane ethyl acetate gradient 9:1→1:1). Rac-N$^2$-(4,6-dichloro-7-methoxy-indan-1-yl)-quinoline-2,6-diamine was obtained as a yellow oil (0.11 g, 45%); MS: m/e=375.4 (M+H$^+$).
Step D: The title compound was prepared in accordance with the general method described in example 3 from isopropyl isocyanate and rac-N$^2$-(4,6-dichloro-7-methoxy-indan-1-yl)-quinoline-2,6-diamine; MS: m/e=460.6 (M+H$^+$).

Example 66

N'-{2-[(1R)-2,3-dihydro-1H-inden-1-ylamino]quinolin-6-yl}-N,N-dimethylsulfamide (R)—N$^2$-Indan-1-yl-quinoline-2,6-diamine (0.05 g, 0.18 mmol) was dissolved in pyridine (1 mL). Dimethylsulfamoyl chloride (0.02 mL) was added and stirred for 72 h at ambient temperature. Then water was added and the mixture extracted with ethyl acetate. The combined organic phases were dried over sodium sulfate, filtered and evaporated. The residue was subjected to column chromatography (silica gel, heptane, ethyl acetate 4:1/1:1) to yield the title compound as a brown oil (30 mg, 43%); MS: m/e=383.6 (M+H$^+$).

Example 67 rac-N'-[2-(2,3-dihydro-1-benzofuran-3-ylamino)quinolin-6-yl]-N,N-dimethylsulfamide The title compound was prepared in accordance with the general method described in example 66 from dimethylsulfamoylchloride and rac-N$^2$-(2,3-dihydro-benzofuran-3-yl)-quinoline-2,6-diamine; MS: m/e=385.6 (M+H$^+$).

Example 68 rac-N'-{2-[(7-methoxy-2,3-dihydro-1H-inden-1-yl)amino]quinolin-6-yl}-N,N-dimethylsulfamide The title compound was prepared in accordance with the general method described in example 66 from dimethylsulfamoyl chloride and rac-N$^2$-(7-methoxy-indan-1-yl)-quinoline-2,6-diamine (Example 172); MS: m/e=412.6 (M+H$^+$).

Example 69 rac-N'-{2-[(8-Methoxy-1,2,3,4-tetrahydronaphthalen-1-yl)amino]quinolin-6-yl}-N,N-dimethylsulfamide The title compound was prepared in accordance with the general method described in example 66 from dimethylsulfamoyl chloride and rac-N$^2$-(8-methoxy-1,2,3,4-tetrahydronaphthalen-1-yl)-quinoline-2,6-diamine; MS: m/e=427.3 (M+H$^+$).

Example 70 rac-N'-{2-[(4,6-Dichloro-7-methoxy-2,3-dihydro-1H-inden-1-yl)amino]quinolin-6-yl}-N,N-dimethylsulfamide The title compound was prepared in accordance with the general method described in example 66 from dimethylsulfamoylchloride and rac-N²-(4,6-dichloro-7-methoxy-indan-1-yl)-quinoline-2,6-diamine; MS: m/e=482.6 (M+H⁺).

Example 71 tert-butyl[({2-[(1R)-2,3-dihydro-1H-inden-1-ylamino]quinolin-6-yl}amino)sulfonyl]carbamate (R)—N²-Indan-1-yl-quinoline-2,6-diamine (0.09 g, 0.33 mmol) and dimethylamino pyridinium N-tert butoxycarbonyl sulfamide (0.12 g, 0.36 mmol) were dissolved in acetonitrile (2.0 mL). After addition of triethylamine (0.05 mL, 0.36 mmol) the reaction mixture was heated to reflux for 16 h. The solvent was removed and the residue subjected to column chromatography (silica gel, heptane/ethyl acetate=9:1/4:1/1:1). The title compound was obtained as a yellow solid (15 mg; 10%); MS: m/e=455.7 (M+H⁺).

Example 72

N-{2-[(1R)-2,3-dihydro-1H-inden-1-ylamino]quinolin-6-yl}sulfamide hydrochloride tert-butyl[({2-[(1R)-2,3-dihydro-1H-inden-1-ylamino]quinolin-6-yl}amino)sulfonyl]carbamate (0.012 mg, 0.026 mmol) was dissolved in HCl/methanol (2.5 M, 1.0 mL) and stirred for 2 h at 60° C. Upon evaporation of the solvent and drying on high vacuum the title compound was obtained as a yellow solid (8 mg; 80%); MS: m/e=392.0 (M+H⁺).

Example 73

Pyrrolidine-1-sulfonic acid [2-((R)-indan-1-ylamino)-quinolin-6-yl]-amide

The title compound was prepared in accordance with the general method described in example 66 from pyrrolidine-1-sulfonyl chloride and (R)—N²-indan-1-yl-quinoline-2,6-diamine; MS: m/e=409.6 (M+H⁺).

Example 74

3,3-Difluoro-pyrrolidine-1-sulfonic acid [2-((R)-indan-1-ylamino)-quinolin-6-yl]-amide The title compound was prepared in accordance with the general method described in example 66 from 3,3-difluoro-pyrrolidine-1-sulfamoylchloride and (R)—N²-indan-1-yl-quinoline-2,6-diamine; MS: m/e=445.8 (M+H⁺).

Example 75

(2-Methoxy-ethyl)-methyl-sulfonic acid [2-((R)-indan-1-ylamino)quinolin-6-yl]-amide The title compound was prepared in accordance with the general method described in example 66 from (2-methoxy-ethyl)-methyl-sulfamoyl chloride and (R)—N²-indan-1-yl-quinoline-2,6-diamine; MS: m/e=427.6 (M+H⁺).

Example 76

Morpholine-4-sulfonic acid [2-((R)-indan-1-ylamino)-quinolin-6-yl]-amide

Step A: 3-(1H-Imidazol-1-ylsulfonyl)-1-methyl-1H-imidazolium trifluoromethanesulfonate (1.5 g, 3.0 mmol) was dissolved in acetonitrile (15 mL) and treated with morpholine (0.30 mL, 4.0 mmol) and stirred for 16 h at ambient temperature. The solvent was removed and the residue subjected to column chromatography (silica gel, heptane, ethyl acetate 1:1, 0:1) to yield 4-(imidazole-1-sulfonyl)-morpholine (0.62 g, 83%) as a white solid; MS: m/e=218.5 (M+H⁺).

Step B: 4-(Imidazole-1-sulfonyl)-morpholine (0.30 g, 1.38 mmol) were dissolved in methylene chloride (6 mL) and methyl triflate (0.172 mL, 1.5 mmol) was added dropwise at 0° C.

After stirring for 2 h at 0° C. a white precipitate formed which was isolated and dried under high vacuum to yield 1-methyl-3-(morpholine-4-sulfonyl)-3H-imidazol-1-ium trifluoromethanesulfonate (0.52 g, 99%); MS: m/e=232.5 (M⁺).

Step C: 1-Methyl-3-(morpholine-4-sulfonyl)-3H-imidazol-1-ium trifluoromethanesulfonate (0.139 g, 0.36 mmol) and (R)—N²-indan-1-yl-quinoline-2,6-diamine (0.10 g, 0.36 mmol) were dissolved in acetonitrile (2 mL) and stirred for 16 h at 80° C. The solvent was removed and the residue subjected to column chromatography (silica gel, heptane, ethyl acetate 4:1/1:1) to yield morpholine-4-sulfonic acid [2-((R)-indan-1-ylamino)-quinolin-6-yl]-amide (0.07 g, 45%) as a yellow solid; MS: m/e=425.7 (M+H⁺).

Example 77

4-Methyl-piperazine-1-sulfonic acid [2-((R)-indan-1-ylamino)-quinolin-6-yl]-amide The title compound was prepared in accordance with the general method described in example 66 from 4-methyl-piperazine-1-sulfonyl chloride and (R)—N²-indan-1-yl-quinoline-2,6-diamine; MS: m/e=438.8 (M+H⁺).

Example 78

Thiomorpholine-4-sulfonic acid [2-((R)-indan-1-ylamino)-quinolin-6-yl]-amide

Step A: 4-(Imidazole-1-sulfonyl)-thiomorpholine was prepared in accordance with step A of the general method described in example 76 from thiomorpholine and 3-(1H-Imidazol-1-ylsulfonyl)-1-methyl-1H-imidazolium trifluoromethanesulfonate; MS: m/e=234.8 (M+H⁺). Step B: 1-Methyl-3-(thiomorpholine-4-sulfonyl)-3H-imidazol-1-ium trifluoromethanesulfonate was prepared in accordance with step B of the general method described in example 76 from 4-(imidazole-1-sulfonyl)-thiomorpholine and methyl triflate; MS: m/e=248.9 (M⁺). Step C: The title compound was prepared in accordance with step C of the general method described in example 76 from 1-methyl-3-(thiomorpholine-4-sulfonyl)-3H-imidazol-1-ium trifluoromethanesulfonate and (R)—N²-indan-1-yl-quinoline-2,6-diamine; MS: m/e=441.8 (M+H⁺).

Example 79

1,1-Dioxo-thiomorpholine-4-sulfonic acid [2-((R)-indan-1-ylamino)-quinolin-6-yl]-amide The title compound was prepared in accordance with the general method described in example 66 from 1,1-dioxothiomorpholine-4-sulfonyl chloride and (R)—N²-indan-1-yl-quinoline-2,6-diamine; MS: m/e=473.7 (M+H⁺).

Example 80

N-{2-[(1R)-2,3-dihydro-1H-inden-1-ylamino]quinolin-6-yl}-N'-(tetrahydro-2H-pyran-4-yl)sulfamide 3-(1H-midazol-1-ylsulfonyl)-1-methyl-1H-imidazolium trifluoromethanesulfonate (0.394 g, 1.10 mmol) and 4-amino-tetrahydropyran (0.10 g, 1.0 mmol) were dissolved in acetonitrile (5 mL) and stirred for 30 min at ambient temperature. Then (R)—N²-indan-1-yl-quinoline-2,6-diamine (0.054 g, 0.20 mmol) were added and the reaction mixture was stirred at 80° C. for 16 h. The solvent was removed and the residue subjected twice to column chromatography (silica gel, first chromatography heptane/ethyl acetate 4:1/1:1/2:1; second chromatography heptane/ethyl acetate 1:1) to yield the title compound (5 mg, 1%) as a yellow solid; MS: m/e=439.7 (M+H⁺).

Example 81

N'-{2-[(1R)-2,3-dihydro-1H-inden-1-ylamino]quinolin-6-yl}-N-methyl-N-(tetrahydro-2H-pyran-4-yl)sulfamide Step A: Imidazole-1-sulfonic acid methyl-(tetrahydro-pyran-4-yl)-amide was prepared in accordance with step A of the general method described in example 76 from methyl-(tetrahydro-pyran-4-yl)amine hydrochloride and 3-(1H-imidazol-1-ylsulfonyl)-1-methyl-1H-imidazolium trifluoromethanesulfonate; MS: m/e=246.8 (M+H⁺).

Step B: 1-Methyl-3-[methyl-(tetrahydro-pyran-4-yl)-sulfamoyl]-3(H)-imidazol-1-ium trifluoromethanesulfonate was prepared in accordance with step B of the general method described in example 76 from imidazole-1-sulfonic acid methyl-(tetrahydro-pyran-4-yl)-amide and methyl triflate; MS: m/e=260.4 (M⁻).

Step C: The title compound was prepared in accordance with step C of the general method described in example 76 from 1-methyl-3-[methyl-(tetrahydro-pyran-4-yl)-sulfamoyl]-3H-imidazol-1-ium trifluoromethanesulfonate and (R)—N²-indan-1-yl-quinoline-2,6-diamine; MS: m/e=453.8 (M+H⁺).

Example 82

1,4-Dioxa-8-aza-spiro[4.5]decane-8-sulfonic acid [2-((R)-indan-1-ylamino)-quinolin-6-yl]-amide Step A: 8-(Imidazole-1-sulfonyl)-1,4-dioxa-8-aza-spiro[4.5]decane was prepared in accordance with step A of the general method described in example 76 from 1,4-dioxa-8-azaspiro(4,5)decan and 3-(1H-imidazol-1-ylsulfonyl)-1-methyl-1H-imidazolium trifluoromethanesulfonate; MS: m/e=274.5 (M+H⁺).

Step B: 3-(1,4-Dioxa-8-aza-spiro[4.5]decane-8-sulfonyl)-1-methyl-3(H)-imidazol-1-ium trifluoromethanesulfonate was prepared in accordance with step B of the general method described in example 76 from 8-(imidazole-1-sulfonyl)-1,4-dioxa-8-aza-spiro[4.5]decane and methyl triflate; MS: m/e=288.4 (M⁻).

Step C: The title compound was prepared in accordance with step C of the general method described in example 76 from 3-(1,4-dioxa-8-aza-spiro[4.5]decane-8-sulfonyl)-1-methyl-3(H)-imidazol-1-ium trifluoromethanesulfonate and (R)—N²-indan-1-yl-quinoline-2,6-diamine; MS: m/e=481.8 (M+H⁺).

Example 83

4-Methoxymethyl-piperidine-1-sulfonic acid [2-((R)-indan-1-ylamino)-quinolin-6-yl]-amide Step A: [1-(Imidazole-1-sulfonyl)-piperidin-4-yl]-methanol was prepared in accordance with step A of the general method described in example 76 from 4-(hydroxymethyl)-piperidine and 3-(1H-imidazol-1-ylsulfonyl)-1-methyl-1H-imidazolium trifluoromethanesulfonate; MS: m/e=246.5 (M+H⁺).

Step B: 3-(4-Methoxymethyl-piperidine-1-sulfonyl)-1-methyl-3(H)-imidazol-1-ium trifluoromethanesulfonate was prepared in accordance with step B of the general method described in example 76 from [1-(imidazole-1-sulfonyl)-piperidin-4-yl]-methanol and methyl triflate; MS: m/e=274.4 (M⁺).

Step C: The title compound was prepared in accordance with step C of the general method described in example 76 from 3-(4-methoxymethyl-piperidine-1-sulfonyl)-1-methyl-3(H)-imidazol-1-ium trifluoromethanesulfonate and (R)—N²-indan-1-yl-quinoline-2,6-diamine; MS: m/e=481.8 (M+H⁺).

Example 84

4-Methoxy-piperidine-1-sulfonic acid [2-((R)-indan-1-ylamino)-quinolin-6-yl]-amide Step A: 1-(Imidazole-1-sulfonyl)-piperidin-4-ol was prepared in accordance with step A of the general method described in example 76 from 4-hydroxypiperidin and 3-(1H-imidazol-1-ylsulfonyl)-1-methyl-1H-imidazolium trifluoromethanesulfonate; MS: m/e=232.5 (M+H⁺).

Step B: 3-(4-Methoxypiperidine-1-sulfonyl)-1-methyl-3(H)-imidazol-1-ium trifluoromethanesulfonate was prepared in accordance with step B of the general method described in example 76 from 1-(imidazole-1-sulfonyl)-piperidin-4-ol and methyl triflate; MS: m/e=260.4 (M⁺).

Step C: The title compound was prepared in accordance with step C of the general method described in example 76 from 3-(4-methoxypiperidine-1-sulfonyl)-1-methyl-3(H)-imidazol-1-ium trifluoromethanesulfonate and (R)—N²-indan-1-yl-quinoline-2,6-diamine; MS: m/e=453.8 (M+H⁺).

Example 85

N-cyclopropyl-N'-{2-[(1R)-2,3-dihydro-1H-inden-1-ylamino]quinolin-6-yl}-N-methylsulfamide Step A: Imidazole-1-sulfonic acid cyclopropyl-methyl-amide was prepared in accordance with step A of the general method described in example 76 from cyclopropyl-methylamine and 3-(1H-imidazol-1-ylsulfonyl)-1-methyl-1H-imidazolium trifluoromethanesulfonate; MS: m/e=202.5 (M+H⁺).

Step B: 3-(Cyclopropyl-methyl-sulfamoyl)-1-methyl-3-H-imidazol-1-ium trifluoromethane-sulfonate was prepared in accordance with step B of the general method described in example 76 from imidazole-1-sulfonic acid cyclopropyl-methyl-amide and methyl triflate; MS: m/e=216.4 (M⁺).

Step C: The title compound was prepared in accordance with step C of the general method described in example 76 from 3-(cyclopropyl-methyl-sulfamoyl)-1-methyl-3-H-imidazol-1-ium trifluoromethanesulfonate and (R)—N$^2$-indan-1-yl-quinoline-2,6-diamine; MS: m/e=409.7 (M+H$^+$).

Example 86

N-(cyclopropylmethyl)-N'-{2-[(1R)-2,3-dihydro-1H-inden-1-ylamino]quinolin-6-yl}-N-methylsulfamide Step A: Imidazole-1-sulfonic acid cyclopropylmethyl-methyl-amide was prepared in accordance with step A of the general method described in example 76 from cyclopropyl-methyl-methylamine and 3-(1H-imidazol-1-ylsulfonyl)-1-methyl-1H-imidazolium trifluoromethanesulfonate; MS: m/e=216.5 (M+H$^+$).
Step B: 3-(Cyclopropylmethyl-methyl-sulfamoyl)-1-methyl-3-H-imidazol-1-ium trifluoromethanesulfonate was prepared in accordance with step B of the general method described in example 76 from imidazole-1-sulfonic acid cyclopropylmethyl-methyl-amide and methyl triflate; MS: m/e=230.4 (M$^-$).
Step C: The title compound was prepared in accordance with step C of the general method described in example 76 from 3-(cyclopropylmethyl-methyl-sulfamoyl)-1-methyl-3-H-imidazol-1-ium trifluoromethanesulfonate and (R)—N$^2$-indan-1-yl-quinoline-2,6-diamine; MS: m/e=423.7 (M+H$^+$).

Example 87

2-Oxa-8-aza-spiro[4.5]decane-8-sulfonic acid [2-((R)-indan-1-ylamino)-quinolin-6-yl]amide Step A: 8-(Imidazole-1-sulfonyl)-2-oxa-8-aza-spiro[4.5]decane was prepared in accordance with step A of the general method described in example 76 from 2-oxa-8-aza-spiro[4.5]decane hydrochloride and 3-(1H-imidazol-1-ylsulfonyl)-1-methyl-1H-imidazolium trifluoromethanesulfonate; MS: m/e=216.5 (M+H$^+$).
Step B: 1-Methyl-3-(2-oxa-8-aza-spiro[4.5]decane-8-sulfonyl)-3(H)-imidazol-1-ium trifluoromethane-sulfonate was prepared in accordance with step B of the general method described in example 76 from 8-(imidazole-1-sulfonyl)-2-oxa-8-aza-spiro[4.5]decane and methyl triflate; MS: m/e=286.4 (M$^+$).
Step C: The title compound was prepared in accordance with step C of the general method described in example 76 from 1-methyl-3-(2-oxa-8-aza-spiro[4.5]decane-8-sulfonyl)-3(H)-imidazol-1-ium trifluoromethanesulfonate and (R)—N$^2$-indan-1-yl-quinoline-2,6-diamine; MS: m/e=479.7 (M+H$^+$).

Example 88

(1S,4S)-2-Oxa-5-aza-bicyclo[2.2.1]heptane-5-sulfonic acid [2-((R)-indan-1-ylamino)-quinolin-6-yl]-amide Step A: (1S,4S)-5-(Imidazole-1-sulfonyl)-2-oxa-5-aza-bicyclo[2.2.1]heptane was prepared in accordance with step A of the general method described in example 76 from all-(S)-(+)-2-oxa-5-aza-bicyclo[2.2.1]heptane hydrochloride and 3-(1H-imidazol-1-ylsulfonyl)-1-methyl-1H-imidazolium trifluoromethanesulfonate; MS: m/e=230.5 (M+H$^-$).
Step B: 1-Methyl-3-[(1S,4S)-(2-oxa-5-aza-bicyclo[2.2.1]hept-5-yl)sulfonyl]-3(H)-imidazol-1-ium trifluoromethane-sulfonate was prepared in accordance with step B of the general method described in example 76 from (1S,4S)-5-(imidazole-1-sulfonyl)-2-oxa-5-aza-bicyclo[2.2.1]heptane and methyl triflate; MS: m/e=244.4 (M$^+$).
Step C: The title compound was prepared in accordance with step C of the general method described in example 76 from 1-methyl-3-[(1S,4S)-(2-oxa-5-aza-bicyclo[2.2.1]hept-5-yl)sulfonyl]-3(H)-imidazol-1-ium trifluoromethanesulfonate and (R)—N$^2$-indan-1-yl-quinoline-2,6-diamine; MS: m/e=437.7 (M+H$^+$).

Example 89

(1S,5R)-8-Oxa-3-aza-bicyclo[3.2.1]octane-3-sulfonic acid [2-((R)-indan-1-ylamino)-quinolin-6-yl]-amide Step A: 3-(Imidazole-1-sulfonyl)-8-oxa-3-aza-bicyclo[3.2.1]octane was prepared in accordance with step A of the general method described in example 76 8-oxa-3-aza-bicyclo[3.2.1]octane hydrochloride and 3-(1H-imidazol-1-ylsulfonyl)-1-methyl-1H-imidazolium trifluoromethanesulfonate; MS: m/e=244.4 (M+H$^+$).
Step B: 1-Methyl-3-(8-oxa-3-aza-bicyclo[3.2.1]octane-3-sulfonyl)-3(H)-imidazol-1-ium trifluoromethanesulfonate was prepared in accordance with step B of the general method described in example 76 from 3-(imidazole-1-sulfonyl)-8-oxa-3-aza-bicyclo[3.2.1]octane and methyl triflate; MS: m/e=258.4 (M$^-$).
Step C: The title compound was prepared in accordance with step C of the general method described in example 76 from 1-methyl-3-(8-oxa-3-aza-bicyclo[3.2.1]octane-3-sulfonyl)-3(H)-imidazol-1-ium trifluoromethanesulfonate and (R)—N$^2$-indan-1-yl-quinoline-2,6-diamine; MS: m/e=451.7 (M+H$^+$).

Example 90

(1S,4S)-2-Oxa-5-aza-bicyclo[2.2.1]heptane-5-sulfonic acid [2-(2,3-dihydro-benzofuran-3-ylamino)-quinolin-6-yl]-amide The title compound was prepared in accordance with step C of the general method described in example 76 from N$^2$-(2,3-dihydro-benzofuran-3-yl)-quinoline-2,6-diamine and 1-methyl-3-[(1S,4S)-(2-oxa-5-aza-bicyclo[2.2.1]hept-5-yl)sulfonyl]-3(H)-imidazol-1-ium trifluoromethanesulfonate; MS: m/e=439.7 (M+H$^+$).

Example 91

(1S,4S)-2-Oxa-5-aza-bicyclo[2.2.1]heptane-5-sulfonic acid [2-(8-methoxy-1,2,3,4-tetrahydro-naphthalen-1-ylamino)-quinolin-6-yl]-amide The title compound was prepared in accordance with step C of the general method described in example 76 from rac-N$^2$-(8-methoxy-1,2,3,4-tetrahydro-naphthalen-1-yl)-quinoline-2,6-diamine and 1-methyl-3-[(1S,4S)-(2-oxa-5-aza-bicyclo[2.2.1]hept-5-yl)sulfonyl]-3(H)-imidazol-1-ium trifluoromethanesulfonate; MS: m/e=481.0 (M+H$^+$).

Example 92

N-Cyclopropyl-N'-{2-[(1R)-2,3-dihydro-1H-inden-1-ylamino]quinolin-6-yl}sulfamide The title compound was prepared in accordance with the general method described in example 66 from cyclopropylsulfamoylchloride and (R)—$N^2$-indan-1-yl-quinoline-2,6-diamine; MS: m/e=395.6 (M+H$^+$).

Example 93 rac-1-Isopropyl-3-[2-(7-methoxy-4-methyl-indan-1-ylamino)-quinolin-6-yl]-urea

Step A: 7-Methoxy-4-Methyl-1-indanon (1.0 g, 0.006 mol) was dissolved in ethanol (10 mL) and hydroxylamine hydrochloride (0.8 g, 0.012 mol) and sodium acetate (0.96 g, 0.012 mmol) were added. The reaction mixture was heated to reflux for 3 h. Then water (10 mL) was added and a precipitation formed which was filtered. The precipitate was washed with water, isolated and dried under high vacuum to yield 7-methoxy-4-methyl-indan-1-one oxime (1.0 g, 92%) as a white solid; MS: m/e=192.4 (M+H$^+$).

Step B: Crude 7-methoxy-4-methyl-indan-1-one oxime (1.0 g, 0.005 mmol) from the procedure described above was dissolved in methanol/HCl (10 mL, 2 M). palladium on carbon 10% (100 mg) was added and the compound was hydrogenated under an atmosphere of hydrogen (3 bar) at 70° C. for 2 h. After filtration, evaporation of the solvent and drying under high vacuum crude rac-7-methoxy-4-methyl-indan-1-ylamine hydrochloride (1 g, 89%) was obtained as a white solid and used in the next reaction without further purification; MS: m/e=214.9 (M+H$^+$).

Step C: Rac-(7-Methoxy-4-methyl-indan-1-yl)-(6-nitro-quinolin-2-yl)-amine was obtained from crude rac-7-methoxy-4-methyl-indan-1-ylamine hydrochloride and 2-chloro-6-nitro-quinoline according to the general procedure described in step A of example 2; MS: m/e=350.6 (M+H$^+$).

Step D: Rac-$N^2$-(7-methoxy-4-methyl-indan-1-yl)-quinoline-2,6-diamine was obtained from (7-methoxy-4-methyl-indan-1-yl)-(6-nitro-quinolin-2-yl)-amine according to the general procedure described in step B of example 2; MS: m/e=320.6 (M+H$^+$). Step E: The title compound was prepared in accordance with the general method described in example 3 from rac-$N^2$-(7-methoxy-4-methyl-indan-1-yl)-quinoline-2,6-diamine and isopropyl isocyanate; MS: m/e=405.6 (M+H$^+$).

Example 94 rac-N'-{2-[(7-Methoxy-4-methyl-2,3-dihydro-1H-inden-1-yl)amino]quinolin-6-yl}-N,N-dimethylsulfamide The title compound was prepared in accordance with the general method described in example 66 from dimethylsulfamoylchloride and rac-$N^2$-(7-methoxy-4-methyl-indan-1-yl)-quinoline-2,6-diamine; MS: m/e=427.6 (M+H$^+$).

Example 95 rac-1-[2-(7-Methoxy-4-methyl-indan-1-ylamino)-quinolin-6-yl]-3-(1-methyl-piperidin-4-yl)-urea The title compound was prepared in accordance with the general method 4 described in example 16 from bis(trichloromethyl) carbonate, 1-methyl-piperidin-4-ylamine and rac-$N^2$-(7-methoxy-4-methyl-indan-1-yl)-quinoline-2,6-diamine; MS: m/e=460.8 (M+H$^+$).

Example 96

4-{3-[2-((R)-Indan-1-ylamino)-quinolin-6-yl]-ureido}-piperidine-1-carboxylic acid methyl ester The title compound was prepared in accordance with the general method 4 described in example 16 from bis(trichloromethyl) carbonate, 4-amino-piperidine-1-carboxylic acid methyl ester hydrochloride and (R)—$N^2$-indan-1-yl-quinoline-2,6-diamine; MS: m/e=460.8 (M+H$^-$).

Example 97

1-[1-(2-Fluoro-ethyl)-piperidin-4-yl]-3-[2-((R)-indan-1-ylamino)-quinolin-6-yl]-urea The title compound was prepared in accordance with the general method 4 described in example 16 from bis(trichloromethyl) carbonate, 1-(2-fluoro-ethyl)-piperidin-4-ylamine and (R)—$N^2$-indan-1-yl-quinoline-2,6-diamine; MS: m/e=448.8 (M+H$^+$).

Example 98 rac-1-[2-(4,6-dichloro-7-methoxy-indan-1-ylamino)-quinolin-6-yl]-3-(1-methyl-piperidin-4-yl)-urea Step A: Rac-7-Methoxy-indan-1-ylamine (2.2 g, 0.011 mol) were dissolved in acetic acid. Over 10 min sulfuryl chloride (1.9 mL, 0.023 mol) was added dropwise at 0° C. The reaction mixture was stirred over night at ambient temperature. Then the solvent was removed and the residue was taken up in iso-propanol. After stirring for some time a precipitation formed which was isolated and dried under high vacuum. Rac-4,6-dichloro-7-methoxy-indan-1-ylamine (2.0 g, 68%) was obtained as a white solid; MS: m/e=232.4 (M+H$^+$).

Step B: Rac-(4,6-dichloro-7-methoxy-indan-1-yl)-(6-nitro-quinolin-2-yl)-amine was obtained from rac-4,6-dichloro-7-methoxy-indan-1-ylamine and 2-chloro-6-nitro-quinoline according to the general procedure described in step A of example 2; MS: m/e=405.6 (M+H$^+$).

Step C: Rac-$N^2$-(4,6-dichloro-7-methoxy-indan-1-yl)-quinoline-2,6-diamine was obtained from rac-(4,6-dichloro-7-methoxy-indan-1-yl)-(6-nitro-quinolin-2-yl)-amine according to the general procedure described in step B of example 2; MS: m/e=375.5 (M+H$^+$).

Step D: The title compound was prepared in accordance with the general method 4 described in example 16 from rac-$N^2$-(4,6-dichloro-7-methoxy-indan-1-yl)-quinoline-2,6-diamine, bis(trichloromethyl) carbonate and 1-methyl-piperidin-4-ylamine; MS: m/e=515.7 (M+H$^+$).

Example 99

1-((3-exo)-8-Cyclopropyl-8-aza-bicyclo[3.2.1]oct-3-yl)-3-[2-((R)-indan-1-ylamino)-quinolin-6-yl]-urea Step A: 8-Cyclopropyl-8-aza-bicyclo[3.2.1]octan-3-one oxime: A mixture of 8-cyclopropyl-8-aza-bicyclo[3.2.1]octan-3-one (CAS no: 60206-33-9) (17.86 g, 108.08 mmol) in ethanol (500 mL) with pyridine (13.05 mL, 162.1 mmol) and hydroxylamine hydrochloride (9.764 g, 140.51 mmol) was refluxed overnight. Cooled to 23° C., filtered off, washed with ethanol and ether and dried in vacuum to give a white solid, which was suspended in 200 mL sat. $Na_2CO_3$ solution and extracted 3 times with dichloromethane, the combined organic layers were dried over $Na_2SO_4$, filtered off and evaporated totally, dried in high vacuum to give the title compound as white crystals (16.3 g, 84%); MS: m/e=181.2 (M+H$^+$).

Step B: (3-exo)-8-Cyclopropyl-8-aza-bicyclo[3.2.1]oct-3-ylamine dihydrochloride: A solution of the above described 8-cyclopropyl-8-aza-bicyclo[3.2.1]octan-3-one oxime (2 g, 11.09 mmol) in pentanol (50 mL) was heated under reflux (150° C.). Sodium (3.089 g, 134.356 mmol) was added portionwise over 2 h. The reaction was then heated under reflux for further 2 h, then cooled to 0° C. Water was added until no more hydrogen gas was evolved. The mixture was acidified using 6 N hydrochloride solution. The phases were separated, extracted the organic layer twice with 6 N hydrochloride solution. The combined aqueos extracts were made alkaline in an ice bath with NaOH pellets to achieve pH 12. Extracted 3 times with dichloromethane, dried the combined organic layers over Na$_2$SO$_4$, filtered off and evaporated totally to give a light yellow oil (5 g contains pentanol). Dissolved in 20 mL ethanol and added trimethylchlorosilane (8.42 mL, 66.57 mmol), then added 150 mL diethyl ether and stirred overnight. Filtered the solid off and dried in high vacuum to give the title compound as white crystals (2.1 g, 79.1%); MS: m/e=167.2 (M+H$^+$).

Step C: The title compound was prepared in accordance with the general method 4 described in example 16 from bis(trichloromethyl) carbonate (44 mg, 0.163 mmol), the above described (3-exo)-8-cyclopropyl-8-aza-bicyclo[3.2.1]oct-3-ylamine dihydrochloride (87 mg, 0.363 mmol) and (R)—N$^2$-indan-1-yl-quinoline-2,6-diamine (100 mg, 0.363 mmol); obtained as a white solid (40 mg, 21%); MS: m/e=468.3 (M+H$^-$).

Example 100

1-[2-((R)-Indan-1-ylamino)-quinolin-6-yl]-3-[(3-exo)-9-(2,2,2-trifluoro-ethyl)-9-aza-bicyclo[3.3.1]non-3-yl]-urea Step A: 9-(2,2,2-Trifluoro-ethyl)-9-aza-bicyclo[3.3.1]nonan-3-one oxime: A mixture of 9-(2,2,2-trifluoro-ethyl)-9-aza-bicyclo[3.3.1]nonan-3-one (CAS no: 209054-63-7) (6.70 g, 30 mmol) in ethanol (100 mL) and hydroxylamine hydrochloride (2.23 g, 32 mmol) was refluxed for 6 h. The reaction mixture was evaporated totally, the residue extracted with dichloromethane and sodium carbonate solution, the organic layers dried over Na$_2$SO$_4$, filtered and the solvents evaporated to give the title compound as a light brown solid. (6.4 g, 89%); MS: m/e=237.1 (M+H$^+$).

Step B: (3-exo)-9-(2,2,2-Trifluoro-ethyl)-9-aza-bicyclo[3.3.1]non-3-ylamine dihydrochloride: A solution of the above described 9-(2,2,2-trifluoro-ethyl)-9-aza-bicyclo[3.3.1]nonan-3-one oxime (1.89 g, 8 mmol) was treated with sodium in pentanol, followed by aqueous workup and HCl salt generation as described in Example 99 Step B. Obtained the title compound as white crystals (1.64 g, 69%); MS: m/e=223.1 (M+H$^+$).

Step C: The title compound was prepared in accordance with the general method 4 described in example 16 from bis(trichloromethyl) carbonate (49 mg, 0.17 mmol), the above described (3-exo)-9-(2,2,2-trifluoro-ethyl)-9-aza-bicyclo[3.3.1]non-3-ylamine dihydrochloride (107 mg, 0.363 mmol) and (R)—N$^2$-indan-1-yl-quinoline-2,6-diamine (100 mg, 0.363 mmol); obtained as an off-white foam (120 mg, 63%); MS: m/e=524.2 (M+H$^+$).

Example 101

1-[2-((R)-Indan-1-ylamino)-quinolin-6-yl]-3-((3-exo)-8-methyl-8-aza-bicyclo[3.2.1]oct-3-yl)-urea The title compound was prepared in accordance with the general method 4 described in example 16 from bis(trichloromethyl) carbonate (49 mg, 0.17 mmol), the (3-exo)-8-methyl-8-aza-bicyclo[3.2.1]oct-3-ylamine dihydrochloride (CAS no: 340682-25-9) (78 mg, 0.363 mmol) and (R)—N$^2$-indan-1-yl-quinoline-2,6-diamine (100 mg, 0.363 mmol); obtained as an off-white solid (82 mg, 51%); MS: m/e=442.4 (M+H$^+$).

Example 102 rac-N$^2$-(7-Methyl-indan-1-yl)-quinoline-2,6-diamine

The title compound was prepared in accordance with the general method described in example 2 from 2-chloro-6-nitro-quinoline and rac-7-methyl-indan-1-ylamine (CAS no: 168902-78-1); MS: m/e=290.4 (M+H$^+$).

Example 103 rac-1-Isopropyl-3-[2-(7-methyl-indan-1-ylamino)-quinolin-6-yl]-urea

The title compound was prepared in accordance with the general method described in example 3 from rac-N$^2$-(7-methyl-indan-1-yl)-quinoline-2,6-diamine and isopropyl isocyanate; MS: m/e=375.4 (M+H$^+$).

Example 104

1-[2-((R)-Indan-1-ylamino)-quinolin-6-yl]-3-((7-exo)-9-methyl-3-oxa-9-aza-bicyclo[3.3.1]non-7-yl)-urea Step A: (7-exo)-9-Methyl-3-oxa-9-aza-bicyclo[3.3.1]non-7-ylamine dihydrochloride: A solution of 9-methyl-3-oxa-9-aza-bicyclo[3.3.1]nonan-7-one oxime (CAS no: 99767-87-0) (0.835 g, 4.0 mmol) was treated with sodium in pentanol, followed by aqueous workup and HCl salt generation as described in Example 99 Step B. Obtained the title compound as brown solid (0.38 g, 34%); MS: m/e=157.1 (M+H$^+$).

Step B: The title compound was prepared in accordance with the general method 4 described in example 16 from bis(trichloromethyl) carbonate (49 mg, 0.17 mmol), the above described (7-exo)-9-methyl-3-oxa-9-aza-bicyclo[3.3.1]non-7-ylamine dihydrochloride (107 mg, 0.363 mmol) and (R)—N$^2$-indan-1-yl-quinoline-2,6-diamine (83 mg, 0.363 mmol); obtained as a light brown solid (56 mg, 34%); MS: m/e=458.5 (M+H$^+$).

Example 105

1-[2-(8-Methoxy-1,2,3,4-tetrahydro-naphthalen-1-ylamino)-quinolin-6-yl]-3-((R)-1-methyl-pyrrolidin-3-yl)-urea The title compound was prepared in accordance with the general method 4 described in example 16 from bis(trichloromethyl) carbonate, (3R)-1-methyl-3-pyrrolidinamine (CAS no: 457097-75-5) and rac-N$^2$-(8-methoxy-1,2,3,4-tetrahydro-naphthalen-1-yl)-quinoline-2,6-diamine; MS: m/e=446.4 (M+H$^+$).

Example 106 rac-N²-(5-Fluoro-indan-1-yl)-quinoline-2,6-diamine

The title compound was prepared in accordance with the general method described in example 2 from 2-chloro-6-nitro-quinoline and rac-5-fluoro-indan-1-ylamine (CAS no: 148960-33-2); MS: m/e=294.3 (M+H⁺).

Example 107 rac-1-[2-(5-Fluoro-indan-1-ylamino)-quinolin-6-yl]-3-isopropyl-urea

The title compound was prepared in accordance with the general method described in example 3 from rac-N²-(5-fluoro-indan-1-yl)-quinoline-2,6-diamine and isopropyl isocyanate; MS: m/e=379.4 (M+H⁺).

Example 108

{2-[2-((R)-Indan-1-ylamino)-quinolin-6-ylamino]-ethyl}-methyl-carbamic acid tert-butyl ester A mixture of (R)—N²-indan-1-yl-quinoline-2,6-diamine (453 mg, 1.645 mmol) in Methanol (10 mL) with acetic acid (0.3 mL, 4.935 mmol) and commercially available methyl-(2-oxo-ethyl)carbamic acid tert-butyl ester (300 mg, 1.731 mmol) was stirred at 23° C. for 1 h. Portionwise addition of sodium cyanoborohydride (286 mg, 4.11 mmol) was followed by additional stirring at 23° C. for 3 h. Poured onto saturated NaHCO₃-solution and extracted twice with ethyl acetate, dried over Na₂SO₄ and evaporated totally gave a crude product which was purified by flash chromatography with heptane and ethyl acetate to give the title compound as a yellow foam (550 mg, 73%); MS: m/e=433.4 (M+H⁺).

Example 109

N²—(R)-Indan-1-yl-N-6-(2-methylamino-ethyl)-quinoline-2,6-diamine

A solution of {2-[2-((R)-Indan-1-ylamino)-quinolin-6-ylamino]-ethyl}-methyl-carbamic acid tert-butyl ester (Example 108) (0.5 g, 1.156 mmol) in dichloromethane (5 mL) was cooled to 0° C. trifluoroacetic acid (2 mL) was dropwise added, the cooling bath was and removed the and the mixture was stirred at 23° C. for 2 h. Poured into saturated NaHCO₃-solution and extracted twice with dichloromethane, dried over Na₂SO₄, filtered off and evaporated totally to yield a crude product which was purified by flash chromatography with heptane/ethyl acetate to give the title compound as a light brown oil (220 mg, 57%); MS: m/e=333.4 (M+H⁻).

Example 110

1-((3-exo)-9-Cyclopropyl-9-aza-bicyclo[3.3.1]non-3-yl)-3-[2-((R)-indan-1-ylamino)-quinolin-6-yl]-urea Step A: 9-Cyclopropyl-9-aza-bicyclo[3.3.1]nonan-3-one: Glutaraldehyde (36.5 mL, 95 mmol) and 1,3-acetonedicarboxylic acid (10 g, 65 mmol) were suspended in water (100 mL) and stirred by a mechanical stirrer under argon for 30 min. To the yellow solution cyclopropylamine (3.5 mL, 50 mmol) were added in one portion whereby a slightly exothermic reaction occurred and a gas evolved. The reaction mixture was stirred at 23° C. overnight. The reaction mixture was acidified with 3 N Hydrochloride solution until pH<2, then extracted with dichloromethane. The water layer was now adjusted with 3 N NaOH to pH 8 and extracted three times with dichloromethane, the organic layers were combined, dried over MgSO₄, filtered and the solvents were evaporated. Purification of the crude product by flash chromatography with n-heptane and ethyl acetate gave the title compound as a white solid (940 mg, 11%); MS: m/e=180.2 (M+H⁺).

Step B: 9-Cyclopropyl-9-aza-bicyclo[3.3.1]nonan-3-one oxime: A mixture of the above described 9-cyclopropyl-9-aza-bicyclo[3.3.1]nonan-3-one (890 mg, 5.0 mmol) in ethanol (20 mL) and hydroxylamine hydrochloride (366 mg, 5.3 mmol) was refluxed for 6 h. The reaction mixture was evaporated totally, the residue extracted with ethyl acetate and sodium bicarbonate solution, the organic layers dried over Na₂SO₄, filtered and the solvents evaporated to give the title compound as a white solid. (890 mg, 100%); MS: m/e=195.2 (M+H⁺).

Step C: (3-exo)-9-Cyclopropyl-9-aza-bicyclo[3.3.1]non-3-ylamine dihydrochloride: A solution of the above described 9-cyclopropyl-9-aza-bicyclo[3.3.1]nonan-3-one oxime (850 mg, 4.4 mmol) was treated with sodium in pentanol, followed by aqueous workup and HCl salt generation as described in Example 99 Step B. Obtained the title compound as white crystals (820 mg, 74%); MS: m/e=181.1 (M+H⁺).

Step D: The title compound was prepared in accordance with the general method 4 described in example 16 from bis(trichloromethyl) carbonate (49 mg, 0.17 mmol), the above described (3-exo)-9-cyclopropyl-9-aza-bicyclo[3.3.1]non-3-ylamine dihydrochloride (92 mg, 0.363 mmol) and (R)—N²-indan-1-yl-quinoline-2,6-diamine (100 mg, 0.363 mmol); obtained as an off-white solid (60 mg, 31%); MS: m/e=482.3 (M+H⁻).

Example 111

1-[2-((R)-Indan-1-ylamino)-quinolin-6-yl]-3-((7-exo)-9-methyl-3-thia-9-aza-bicyclo[3.3.1]non-7-yl)-urea Step A: 9-Methyl-3-thia-9-aza-bicyclo[3.3.1]nonan-7-one oxime: A mixture of 9-Methyl-3-thia-9-aza-bicyclo[3.3.1]nonan-7-one (CAS no: 99709-31-6) (3.0 g, 17.5 mmol) in ethanol (100 mL) and hydroxylamine hydrochloride (1.58 g, 22.8 mmol) was refluxed for 16 h. Cooled to 23° C., the precipitate was filtered off, washed with ethanol and diethyl ether and dried in vacuum to give a light brown solid (2.5 g), which was partitioned between dichloromethane and sodium carbonate solution, the organic layers dried over Na₂SO₄, filtered and the solvents evaporated to give the title compound as a white solid. (1.3 g, 40%); MS: m/e=187.1 (M+H⁺).

Step B: (7-exo)-9-Methyl-3-thia-9-aza-bicyclo[3.3.1]non-7-ylamine dihydrochloride: A solution of the above described 9-methyl-3-thia-9-aza-bicyclo[3.3.1]nonan-7-one oxime (1.55 g, 8.32 mmol) was treated with sodium in pentanol, followed by aqueous workup and HCl salt generation as described in Example 99 Step B. Obtained the title compound as white crystals (1.6 g, 78%); MS: m/e=173.1 (M+H⁺).

Step C: The title compound was prepared in accordance with the general method 4 described in example 16 from bis(trichloromethyl) carbonate (44 mg, 0.16 mmol), the above described (7-exo)-9-methyl-3-thia-9-aza-bicyclo[3.3.1]non-7-ylamine dihydrochloride (89 mg, 0.363 mmol) and (R)—N²-indan-1-yl-quinoline-2,6-diamine (100 mg, 0.363 mmol); obtained as an off-white solid (20 mg, 12%); MS: m/e=474.3 (M+H⁻).

Example 112

4-Isopropyl-piperazine-1-carboxylic acid [2-((R)-indan-1-ylamino)-quinolin-6-yl]-amide The title compound was prepared in accordance with the general method 4 described in example 16 from bis(trichloromethyl) carbonate (44 mg, 0.16 mmol), commercially available 1-(2-propyl)-piperazine (47 mg, 0.363 mmol) and (R)—$N^2$-indan-1-yl-quinoline-2,6-diamine (100 mg, 0.363 mmol); obtained as a white solid (32 mg, 21%); MS: m/e=430.4 (M+H$^+$).

Example 113

4-tert-Butyl-piperazine-1-carboxylic acid [2-((R)-indan-1-ylamino)-quinolin-6-yl]-amide The title compound was prepared in accordance with the general method 4 described in example 16 from bis(trichloromethyl) carbonate (44 mg, 0.16 mmol), commercially available N-tert-butylpiperazine (52 mg, 0.363 mmol) and (R)—$N^2$-indan-1-yl-quinoline-2,6-diamine (100 mg, 0.363 mmol); obtained as a white solid (150 mg, 93%); MS: m/e=444.5 (M+H$^+$).

Example 114

1-[2-((R)-Indan-1-ylamino)-quinolin-6-yl]-3-methyl-imidazolidin-2-one

To a solution of $N^2$—(R)-indan-1-yl-$N^6$-(2-methylaminoethyl)-quinoline-2,6-diamine (Example 109) (200 mg, 0.6 mmol) in dichloromethane (100 mL) at 0° C. was added 1,1'-carbonyldiimidazole (98 mg, 0.6 mmol) the icebath was removed and the mixture was stirred at 23° C. overnight, then 2 h at 50° C. All volatiles were removed in vacuum and the residue was purified by basic silica gel column chromatography with heptane to ethyl acetate to give the title compounds as a light brown solid (35 mg, 16%); MS: m/e=359.2 (M+H$^+$).

Example 115 rac-1-[2-(5-Fluoro-indan-1-ylamino)-quinolin-6-yl]-3-(1-isopropyl-piperidin-4-yl)-urea The title compound was prepared in accordance with the general method 4 described in example 16 from bis(trichloromethyl) carbonate, 1-isopropyl-piperidin-4-ylamine (CAS no: 127285-08-9) and rac-$N^2$-(5-fluoro-indan-1-yl)-quinoline-2,6-diamine; MS: m/e=460.6 (M−H$^+$).

Example 116

N-[2-((R)-Indan-1-ylamino)-quinolin-6-yl]-isobutyramide (R)—$N^2$-indan-1-yl-quinoline-2,6-diamine (0.05 g, 0.18 mmol), triethylamine (0.028 mL, 0.2 mmol) and isobutyryl chloride (0.021 mL, 0.2 mmol) were dissolved in toluene (2.0 mL).

The reaction mixture was heated to 80° C. A precipitation formed. The reaction mixture was diluted with water and extracted with dichloromethane (3×). The combined organic phases were dried over sodium sulfate and evaporated. The crude product was purified by column chromatography (silica gel, heptane:ethyl acetate 9:1/4:1/2:1/1:1). The title compound (0.049 g, 78%) was obtained as a yellow solid; MS: m/e=346.6 (M+H$^+$).

Example 117

2-Cyclopentyl-N-[2-((R)-indan-1-ylamino)-quinolin-6-yl]-acetamide

The title compound was prepared in accordance with the general method 9 described in example 116 from cyclopentylacetyl chloride, triethylamine and (R)—$N^2$-indan-1-yl-quinoline-2,6-diamine; MS: m/e=386.7 (M+H$^+$).

Example 118 rac-N-[2-(8-Methoxy-1,2,3,4-tetrahydro-naphthalen-1-ylamino)-quinolin-6-yl]-isobutyramide The title compound was prepared in accordance with the general method 9 described in example 116 from isobutyryl chloride, triethylamine and rac-$N^2$-(8-methoxy-1,2,3,4-tetrahydro-naphthalen-1-yl)-quinoline-2,6-diamine; MS: m/e=390.3 (M+H$^+$).

Example 119 rac-2-Dimethylamino-N-[2-(8-methoxy-1,2,3,4-tetrahydro-naphthalen-1-ylamino)-quinolin-6-yl]-acetamide N,N-Dimethylglycine (49 mg, 0.48 mmol), N,N-diisopropyl ethyl amine (217 mg, 1.68 mmol) and 2-(1H-benzotriazole-1-yl)-1,1,3,3-tetramethyluronium tetrafluoroborate (220 mg, 0.69 mmol) were dissolved in dichloromethane (6 mL) and dimethylformamide (1.5 mL). The reaction mixture was stirred at room temperature for 30 minutes. rac-$N^2$-(8-Methoxy-1,2,3,4-tetrahydro-naphthalen-1-yl)-quinoline-2,6-diamine (150 mg, 0.47 mmol) was added and stirred was continued overnight. The reaction mixture was diluted with water and extracted with dichloromethane (3×). The combined organic phases were dried over sodium sulfate and evaporated. The crude product was purified by column chromatography (silica gel, dichloromethane/methanol 100:0→90:10). The title compound (147 mg, 77%) was obtained as a light brown solid; MS: m/e=405.5 (M+H$^+$).

Example 120 rac-2-Methoxy-N-[2-(8-methoxy-1,2,3,4-tetrahydro-naphthalen-1-ylamino)-quinolin-6-yl]-acetamide The title compound was prepared in accordance with the general method 14 described in example 119 from rac-$N^2$-(8-methoxy-1,2,3,4-tetrahydro-naphthalen-1-yl)-quinoline-2,6-diamine and methoxyacetic acid; MS: m/e=392.3 (M+H$^+$).

Example 121 rac-N-[2-(8-Methoxy-1,2,3,4-tetrahydro-naphthalen-1-ylamino)-quinolin-6-yl]-2-morpholin-4-yl-acetamide The title compound was prepared in accordance with the general method 14 described in example 119 from rac-$N^2$-(8- methoxy-1,2,3,4-tetrahydro-naphthalen-1-yl)-quinoline-2,6-diamine and morpholin-4-yl-acetic acid; MS: m/e=447.3 (M+H$^+$).

Example 122

{[2-((R)-Indan-1-ylamino)-quinolin-6-ylcarbamoyl]-methyl}-arbamic acid tert-butyl ester (R)—N$^2$-Indan-1-yl-quinoline-2,6-diamine (0.05 g, 0.18 mmol) were dissolved in tetrahydrofuran (3 mL) and cooled down to 0° C. Then N-(tert-butoxycarbonyl)glycine (0.035 g, 0.2 mmol), 1-hydroxybenzotriazole (0.027 g, 0.2 mmol), diisopropylethylamine (0.068 mL, 0.4 mmol) and 1-(3-dimethylaminopropyl)-3-ethylcarbodiimide hydrochloride (0.038 g, 0.2 mmol) were added. After 30 min at 0° C. the mixture was allowed to warm up to ambient temperature and was stirred there for another 16 h. The reaction mixture was diluted with water and extracted with ethyl acetate (3×20 mL). The combined organic phases were dried on sodium sulfate, filtered, concentrated and the residue was subjected to column chromatography (silica gel, heptane/ethyl acetate 9:1, 4:1, 1:1). The title compound was obtained as a yellow foam (0.066 g, 86%); MS: m/e=433.7 (M+H$^+$).

Example 123

2-Amino-N-[2-((R)-indan-1-ylamino)-quinolin-6-yl]-acetamide

{[2-((R)-Indan-1-ylamino)-quinolin-6-ylcarbamoyl]-methyl}-arbamic acid tert-butyl ester (0.05 g, 0.12 mmol) were dissolved in methylene chlorid (1.0 mL). At 0° C. trifluoro acetic acid (0.085 mL, 1.2 mmol) were added. The reaction mixture was stirred at ambient temperature for 72 h. Upon addition of sat. sodium carbonate the mixture was extracted with ethyl acetate (3×10 mL). The combined organic phases were dried on sodium sulfate, filtered and concentrated. After drying under high vacuum the title compound was obtained as a yellow solid (0.032 g, 83%); MS: m/e=333.7 (M+H$^+$).

Example 124

1-Methyl-piperidine-4-carboxylic acid [2-((R)-indan-1-ylamino)-quinolin-6-yl]-amide According to the general method described in example 122 the title compound was obtained from (R)—N$^2$-indan-1-yl-quinoline-2,6-diamine as an off-white solid; MS: m/e=333.7 (M+H$^+$).

Example 125 rac-N-[2-(8-Methoxy-1,2,3,4-tetrahydro-naphthalen-1-ylamino)-quinolin-6-yl]-2-(tetrahydro-pyran-4-yl)-acetamide The title compound was prepared in accordance with the general method 14 described in example 119 from rac-N$^2$-(8-methoxy-1,2,3,4-tetrahydro-naphthalen-1-yl)-quinoline-2,6-diamine and tetrahydropyran-4-yl-acetic acid; MS: m/e=446.1 (M+H$^+$).

Example 126 rac-2-Dimethylamino-N-[2-(7-methoxy-indan-1-ylamino)-quinolin-6-yl]-acetamide

The title compound was prepared in accordance with the general method 14 described in example 119 from rac-N$^2$-(7-methoxy-indan-1-yl)-quinoline-2,6-diamine (Example 172) and N,N-dimethylglycine; MS: m/e=391.4 (M+H$^+$).

Example 127 rac-N-[2-(6-Fluoro-indan-1-ylamino)-quinolin-6-yl]-2-(4-methyl-piperazin-1-yl)-acetamide The title compound was prepared in accordance with the general method 14 described in example 119 from rac-N$^2$-(6-fluoro-indan-1-yl)-quinoline-2,6-diamine and (4-methyl-piperazin-1-yl)-acetic acid; MS: m/e=434.5 (M+H$^+$).

Example 128 rac-(N)-[2-(7-Methoxy-indan-1-ylamino)-quinolin-6-yl]-isobutyramide

The title compound was prepared in accordance with the general method 9 described in example 116 from isobutyryl chloride, triethylamine and rac-N$^2$-(7-methoxy-indan-1-yl)-quinoline-2,6-diamine (Example 172); MS: m/e=376.4 (M+H$^+$).

Example 129 rac-1-Methyl-piperidine-4-carboxylic acid [2-(7-methoxy-indan-1-ylamino)-quinolin-6-yl]-amide The title compound was prepared in accordance with the general method 14 described in example 119 from rac-N$^2$-(7-methoxy-indan-1-yl)-quinoline-2,6-diamine (Example 172) and 1-methyl-piperidine-4-carboxylic acid; MS: m/e=414.3 (M+H$^+$).

Example 130 rac-1-Isopropyl-3-[2-(7-methoxy-5-methyl-indan-1-ylamino)-quinolin-6-yl]-urea

Step A: 7-Methoxy-5-methyl-1-indanon (CAS no: 62358-78-5) (7.70 g, 0.044 mol) was dissolved in ethanol (40 mL) and hydroxylamine hydrochloride (6.23 g, 0.09 mol) and sodium acetate (7.38 g, 0.09 mol) were added. The reaction mixture was heated to reflux for 3 h. Then water (100 mL) was added and a precipitation formed which was filtered. The precipitate was washed with water, isolated and dried under high vacuum to yield 7-methoxy-5-methyl-indan-1-one oxime (8.20 g, 98%) as a white solid; MS: m/e=192.4 (M+H$^+$).

Step B: Crude 7-methoxy-5-methyl-indan-1-one oxime (8.0 g, 0.042 mol) from the procedure described above was dissolved in methanol/HCl (10 mL, 2 M). palladium on carbon 10% (800 mg) was added and the compound was hydrogenated under an atmosphere of hydrogen (3 bar) at 70° C. for 27 h. After filtration, evaporation of the solvent and drying under high vacuum crude rac-7-methoxy-5-methyl-indan-1-ylamine hydrochloride (2.3 g, 26%) was obtained as a white solid and used in the next reaction without further purification; MS: m/e=214.9 (M+H$^+$).

Step C: Rac-(7-Methoxy-5-methyl-indan-1-yl)-(6-nitro-quinolin-2-yl)-amine was obtained from crude rac-7-methoxy-5-methyl-indan-1-ylamine hydrochloride and 2-chloro-6-nitro-quinoline according to the general procedure described in step A of example 2; MS: m/e=350.6 (M+H$^+$).

Step D: Rac-N$^2$-(7-Methoxy-5-methyl-indan-1-yl)-quinoline-2,6-diamine was obtained from rac-(7-methoxy-5-methyl-indan-1-yl)-(6-nitro-quinolin-2-yl)-amine according to the general procedure described in step B of example 2; MS: m/e=320.6 (M+H$^+$).

Step E: The title compound was prepared in accordance with the general method described in example 3 from rac-N$^2$-(7-methoxy-5-methyl-indan-1-yl)-quinoline-2,6-diamine and isopropyl isocyanate; MS: m/e=405.6 (M+H$^+$).

Example 131 rac-1-[2-(7-Methoxy-5-methyl-indan-1-ylamino)-quinolin-6-yl]-3-(1-methyl-piperidin-4-yl)-urea The title compound was prepared in accordance with the general method 4 described in example 16 from bis(trichloromethyl) carbonate, 1-methyl-piperidin-4-ylamine and rac-N$^2$-(7-methoxy-5-methyl-indan-1-yl)-quinoline-2,6-diamine; MS: m/e=460.8 (M+H$^+$).

Example 132 rac-N'-{2-[(7-Methoxy-5-methyl-2,3-dihydro-1H-inden-1-yl)amino]quinolin-6-yl}-N,N-dimethylsulfamide The title compound was prepared in accordance with the general method described in example 66 from dimethylsulfamoylchloride and rac-N$^2$-(7-methoxy-5-methyl-indan-1-yl)-quinoline-2,6-diamine; MS: m/e=427.6 (M+H$^+$).

Example 133

1-(1-Cyanomethyl-piperidin-4-yl)-3-[2-((R)-indan-1-ylamino)-quinolin-6-yl]-urea

Step A: Piperidin-4-yl-carbamic acid tert-butyl ester (CAS no: 259180-66-0) (0.70 g, 0.0029 Mol) were dissolved in HCl/Methanol 2.5 M (5 mL) and stirred at 40° C. for 4 h. Then the solvent was removed and the obtained crystals dried under high vacuum. (4-Amino-piperidin-1-yl)-acetonitrile dihydrochloride (0.6 g, 100%) was obtained as a white powder; MS: m/e=140.6 (M+H$^+$).

Step B: The title compound was prepared in accordance with the general method 4 described in example 16 from bis(trichloromethyl) carbonate, (4-amino-piperidin-1-yl)-acetonitrile dihydrochlorid and (R)—N$^2$-indan-1-yl-quinoline-2,6-diamine; MS: m/e=441.8 (M+H$^+$).

Example 134

1-[2-((R)-Indan-1-ylamino)-quinolin-6-yl]-3-[1-(2,2,2-trifluoro-ethyl)-piperidin-4-yl]-urea The title compound was prepared in accordance with the general method 4 described in example 16 from bis(trichloromethyl) carbonate, 1-(2,2,2-trifluoro-ethyl)-piperidin-4-ylamine hydrochloride (CAS no: 180869-49-2) and (R)—N$^2$-indan-1-yl-quinoline-2,6-diamine; MS: m/e=484.8 (M+H$^+$).

Example 135

1-[2-((R)-Indan-1-ylamino)-quinolin-6-yl]-3-[1-(2-methanesulfonyl-ethyl)-piperidin-4-yl]-urea 1-[2-((R)-Indan-1-ylamino)-quinolin-6-yl]-3-piperidin-4-yl-urea (0.05 g, 0.12 mmol), triethylamine (0.02 mL, 0.15 mmol) and methylvinylsulfone (0.016 g, 0.15 mmol) were dissolved in tetrahydrofuran (3 mL) and stirred at ambient temperature for 16 h. Ethyl acetate (10 mL) was added to the reaction mixture and everything subsequently washed with water. The organic phase was dried over sodium sulfate, filtered and the filtrate evaporated. The residue was subjected to column chromatography (basic silica gel, ethyl acetate) to yield the title compound (0.026 g, 41%) as an off-white solid; MS: m/e=508.8 (M+H$^+$).

Example 136

2-(4-{3-[2-((R)-Indan-1-ylamino)-quinolin-6-yl]-ureido}-piperidin-1-yl)-N,N-dimethylacetamide 1-[2-((R)-Indan-1-ylamino)-quinolin-6-yl]-3-piperidin-4-yl-urea (0.05 g, 0.12 mmol), 2-chloro-N,N-dimethylacetamide (0.023 mg, 0.18 mmol) and sodium carbonate (0.02 g, 0.18 mmol) were stirred at ambient temperature for 16 h in N,N-dimethylformamide (3 mL). The reaction mixture was evaporated. The residue was taken up in dimethylsulfoxide (1 mL) and subjected to preparative HPLC to yield the title compound (0.053 g, 87%) as a yellow oil; MS: m/e=487.8 (M+H$^+$).

Example 137

1-[1-(2-Hydroxy-ethyl)-piperidin-4-yl]-3-[2-((R)-indan-1-ylamino)-quinolin-6-yl]-urea 1-[2-((R)-Indan-1-ylamino)-quinolin-6-yl]-3-piperidin-4-yl-urea (0.05 g, 0.12 mmol), triethylamine (0.02 mL, 0.15 mmol) and 2-bromoethanol (0.019 mL, 0.15 mmol) were dissolved in tetrahydrofuran (3 mL) and stirred at 60° C. for 7 h. The reaction mixture was evaporated. The residue was subjected to column chromatography (basic silica gel, methylene chloride/methanol 19:1, 9:1) to yield the title compound (0.023 g, 41%) as a white solid; MS: m/e=446.8 (M+H$^+$).

Example 138

[2-((R)-Indan-1-ylamino)-quinolin-6-yl]-carbamic acid isopropyl ester (R)—N$^2$-indan-1-yl-quinoline-2,6-diamine (0.07 g, 0.25 mmol), triethylamine (0.052 mL, 0.38 mmol) and isopropyl chloroformate (1M solution in toluene) (0.281 mL, 0.28 mmol) were dissolved in toluene (3 mL) and stirred at 60° C. for 10 h. The reaction mixture was diluted with water and extracted with ethyl acetate (10 mL). The combined organic phases was dried over sodium sulfate, filtered and the filtrate evaporated. The residue was subjected to column chromatography (silica gel, heptane/ethyl acetate, 9:1, 4:1, 3:1) to yield the title compound (0.026 g, 41%) as a white foam; MS: m/e=361.7 (M+H$^+$).

Example 139 rac-N-[2-(7-Methoxy-indan-1-ylamino)-quinolin-6-yl]-2-(4-methyl-piperazin-1-yl)-acetamide The title compound was prepared in accordance with the general method 14 described in example 119 from rac-N$^2$-(7-methoxy-indan-1-yl)-quinoline-2,6-diamine (Example 172) and (4-methylpiperazinl-yl)-acetic acid; MS: m/e=446.1 (M+H$^+$).

Example 140 rac-Cyclopropanecarboxylic acid [2-(7-methoxy-indan-1-ylamino)-quinolin-6-yl]-amide The title compound was prepared in accordance with the general method 14 described in example 119 from rac-$N^2$-(7-methoxy-indan-1-yl)-quinoline-2,6-diamine (Example 172) and cyclopropyl carboxylic acid; MS: m/e=374.4 (M+H$^+$).

Example 141 rac-Cyclopropanecarboxylic acid [2-(5-fluoro-indan-1-ylamino)-quinolin-6-yl]-amide The title compound was prepared in accordance with the general method 14 described in example 119 from rac-$N^2$-(5-fluoro-indan-1-yl)-quinoline-2,6-diamine and cyclopropyl carboxylic acid; MS: m/e=362.2 (M+H$^+$).

Example 142 rac-N-[2-(5-Fluoro-indan-1-ylamino)-quinolin-6-yl]-2-(4-methyl-piperazin-1-yl)-acetamide The title compound was prepared in accordance with the general method 14 described in example 119 from rac-$N^2$-(5-fluoro-indan-1-yl)-quinoline-2,6-diamine and (4-methyl-piperazin-1-yl)-acetic acid; MS: m/e=434.3 (M+H$^+$).

Example 143 rac-$N^2$-(6-Fluoro-indan-1-yl)-quinoline-2,6-diamine

The title compound was prepared in accordance with the general method described in example 2 from 2-chloro-6-nitro-quinoline and rac-6-fluoro-indan-1-ylamine (CAS no: 168902-77-0); MS: m/e=294.3 (M+H$^+$).

Example 144 rac-1-[2-(6-Fluoro-indan-1-ylamino)-quinolin-6-yl]-3-isopropyl-urea

The title compound was prepared in accordance with the general method described in example 3 from rac-$N^2$-(6-fluoro-indan-1-yl)-quinoline-2,6-diamine and isopropyl isocyanate; MS: m/e=379.4 (M+H$^+$).

Example 145 rac-$N^2$-(7-Fluoro-indan-1-yl)-quinoline-2,6-diamine

Step A+B: rac-7-Fluoro-indan-1-ylamine was prepared in accordance with the general method described in example 130, step A and B from 7-fluoro-indan-1-one (CAS no: 651735-59-0); MS: m/e=152.3 (M+H$^+$).

Step C+D: The title compound was prepared in accordance with the general method described in example 2 from 2-chloro-6-nitro-quinoline and rac-7-fluoro-indan-1-ylamine; MS: m/e=294.3 (M+H$^+$).

Example 146 rac-1-[2-(7-Fluoro-indan-1-ylamino)-quinolin-6-yl]-3-isopropyl-urea

The title compound was prepared in accordance with the general method described in example 3 from rac-$N^2$-(7-fluoro-indan-1-yl)-quinoline-2,6-diamine and isopropyl isocyanate; MS: m/e=379.4 (M+H$^+$).

Example 147 rac-N-[2-(5-Fluoro-indan-1-ylamino)-quinolin-6-yl]-2-(4-isopropyl-piperazin-1-yl)-acetamide The title compound was prepared in accordance with the general method 14 described in example 119 from rac-$N^2$-(5-fluoro-indan-1-yl)-quinoline-2,6-diamine and (4-isopropyl-piperazin-1-yl)-acetic acid (CAS no: 95470-68-1); MS: m/e=462.5 (M+H$^+$).

Example 148

(1S,4S)-2-Oxa-5-aza-bicyclo[2.2.1]heptane-5-sulfonic acid [2-(7-methoxy-indan-1-ylamino)-quinolin-6-yl]-amide The title compound was prepared in accordance with step C of the general method described in example 76 from rac-$N^2$-(7-methoxy-indan-1-yl)-quinoline-2,6-diamine (Example 172) and 1-methyl-3-[(1S,4S)-(2-oxa-5-aza-bicyclo[2.2.1]hept-5-yl)sulfonyl]-3(H)-imidazol-1-ium trifluoromethanesulfonate; MS: m/e=467.0 (M+H$^+$).

Example 149

[2-((R)-Indan-1-ylamino)-quinolin-6-yl]-thiourea

Step A: (R)-6-Amino-2-indanoyl-quinoline (1.2 g, 4.4 mmol) was dissolved in 50 mL acetone. Benzoyl-isothiocyanate (749 mg, 4.6 mmol) was added and the reaction mixture was stirred at room temperature overnight. The solvent was evaporated and the residue was purified by column chromatography (silica gel, dichloromethane/ethyl acetate 19:1). 1-Benzoyl-3-[2-((R)-indan-1-ylamino)-quinolin-6-yl]-thiourea (1.55 g, 81%) was obtained as a light yellow foam; MS: m/e=439.1 (M+H$^+$).

Step B: 1-Benzoyl-3-[2-((R)-indan-1-ylamino)-quinolin-6-yl]-thiourea (1.5 g, 3.4 mmol) was suspended in 50 mL methanol. 4.1 mL 1N sodium hydroxide solution was added and the reaction mixture was refluxed for 2 h. The reaction mixture was diluted with 80 mL water and extracted with dichloromethane (2×100 mL). The organic phases were pooled, dried with sodium sulfate and evaporated. The residue was recrystallized from dichloromethane and diethylether. The title compound (660 mg, 58%) was obtained as an off-white solid; MS: m/e=335.3 (M+H$^+$).

Example 150

1-[2-((R)-Indan-1-ylamino)-quinolin-6-yl]-2-methyl-isothiourea hydroiodide

[2-((R)-Indan-1-ylamino)-quinolin-6-yl]-thiourea (600 mg, 1.8 mmol) was dissolved in 20 mL acetone and 10 mL tetrahydrofuran. Methyliodide (306 mg, 2.2 mmol) was added and the reaction mixture was stirred at room temperature for 3 h. The solvent was evaporated and the residue was recrystallized from dichloromethane and diethylether. The title compound (720 mg, 84%) was obtained as a yellow solid; MS: m/e=349.4 (M+H$^+$).

Example 151

N-[2-((R)-Indan-1-ylamino)-quinolin-6-yl]-morpholine-4-carboxamidine

1-[2-((R)-Indan-1-ylamino)-quinolin-6-yl]-2-methyl-isothiourea hydroiodide (345 mg, 0.72 mmol) was dissolved in 10 mL ethanol. Morpholine (350 mg, 4 mmol) was added and the reaction mixture was refluxed overnight. The solvent was evaporated and the residue was purified by column chromatography (silica gel, dichloromethane/methanol 40:1). The title compound (144 mg, 51%) was obtained as a light yellow foam; MS: m/e=388.3 (M+H$^+$).

Example 152

N-[2-((R)-Indan-1-ylamino)-quinolin-6-yl]-N'-(1-methyl-piperidin-4-yl)-guanidine The title compound was prepared in accordance with the general method 16 described in example 151 from 1-[2-((R)-indan-1-ylamino)-quinolin-6-yl]-2-methyl-isothiourea hydroiodide and 1-methylpiperidine-4-amine; MS: m/e=415.3 (M+H$^+$).

Example 153

N-[2-((R)-Indan-1-ylamino)-quinolin-6-yl]-N-isopropyl-guanidine

The title compound was prepared in accordance with the general method 16 described in example 151 from 1-[2-((R)-indan-1-ylamino)-quinolin-6-yl]-2-methyl-isothiourea hydroiodide and isopropylamine; MS: m/e=360.3 (M+H$^+$).

Example 154

N-Cyclopropyl-N'-[2-((R)-indan-1-ylamino)-quinolin-6-yl]-guanidine

The title compound was prepared in accordance with the general method 16 described in example 151 from 1-[2-((R)-indan-1-ylamino)-quinolin-6-yl]-2-methyl-isothiourea hydroiodide and cyclopropylamine; MS: m/e=358.4 (M+H$^+$).

Example 155 rac-1-[2-(6-Fluoro-indan-1-ylamino)-quinolin-6-yl]-3-(1-isopropyl-piperidin-4-yl)-urea The title compound was prepared in accordance with the general method 4 described in example 16 from bis(trichloromethyl) carbonate, 1-isopropyl-piperidin-4-ylamine (CAS no: 127285-08-9) and rac-N$^2$-(6-fluoro-indan-1-yl)-quinoline-2,6-diamine; MS: m/e=462.5 (M+H$^+$).

Example 156 rac-1-[2-(7-Fluoro-indan-1-ylamino)-quinolin-6-yl]-3-(1-isopropyl-piperidin-4-yl)-urea The title compound was prepared in accordance with the general method 4 described in example 16 from bis(trichloromethyl) carbonate, 1-isopropyl-piperidin-4-ylamine (CAS no: 127285-08-9) and rac-N$^2$-(7-fluoro-indan-1-yl)-quinoline-2,6-diamine; MS: m/e=462.3 (M+H$^+$).

Example 157 rac-[2-(7-Fluoro-indan-1-ylamino)-quinolin-6-yl]-carbamic acid methyl ester

The title compound was obtained as a by-product in the above described synthesis of example 156; MS: m/e=352.3 (M+H$^+$).

Example 158 rac-N-[2-(5-Fluoro-indan-1-ylamino)-quinolin-6-yl]-2-morpholin-4-yl-acetamide

The title compound was prepared in accordance with the general method 14 described in example 119 from rac-N$^2$-(5-fluoro-indan-1-yl)-quinoline-2,6-diamine and morpholin-4-yl-acetic acid; MS: m/e=421.2 (M+H$^+$).

Example 159 rac-N-[2-(5-Fluoro-indan-1-ylamino)-quinolin-6-yl]-acetamide

The title compound was prepared in accordance with the general method 14 described in example 119 from rac-N$^2$-(5-fluoro-indan-1-yl)-quinoline-2,6-diamine and acetic acid; MS: m/e=334.4 (M−H$^+$).

Example 160 rac-2-Cyclopropyl-N-[2-(5-fluoro-indan-1-ylamino)-quinolin-6-yl]-acetamide

The title compound was prepared in accordance with the general method 14 described in example 119 from rac-N$^2$-(5-fluoro-indan-1-yl)-quinoline-2,6-diamine and cyclopropyl acetic acid; MS: m/e=376.2 (M+H$^+$).

Example 161 rac-N-[2-(7-Fluoro-indan-1-ylamino)-quinolin-6-yl]-2-(4-methyl-piperazin-1-yl)-acetamide The title compound was prepared in accordance with the general method 14 described in example 119 from rac-N$^2$-(7-fluoro-indan-1-yl)-quinoline-2,6-diamine and (4-methyl-piperazin-1-yl)-acetic acid; MS: m/e=434.4 (M+H$^+$).

Example 162 rac-Cyclopropanecarboxylic acid [2-(7-fluoro-indan-1-ylamino)-quinolin-6-yl]-amide The title compound was prepared in accordance with the general method 14 described in example 119 from rac-N$^2$-(7-fluoro-indan-1-yl)-quinoline-2,6-diamine and cyclopropyl acetic acid; MS: m/e=362.4 (M+H$^+$).

Example 163

N$^2$—(R)-Indan-1-yl-N6-morpholin-4-yl-quinoline-2,6-diamine

Step A: A stirred mixture of commercially available 6-bromo-2-chloro-quinoline (3.0 g, 12.4 mmol), commercially available (R)-1-aminoindane (2.0 g, 15.0 mmol), N-ethyl-diisopropylamine (2.4 g, 18.6 mmol) and N-methyl-pyrrolidone (3 mL) was heated in a sealed tube for 24 h at 135° C. The reaction mixture was poured into water (70 mL) and extracted with diethyl ether (2×125 mL). The combined organic layers were washed with water (2×150 mL), dried (MgSO$_4$) and evaporated. Further purification of the crude product by column chromatography on silica gel (toluene/ethyl acetate 9:1) and crystallization (diethyl ether/heptane) yielded the title compound (3.39 mg, 81%) as off-white solid. MS (ISP) 339.0 (M+H$^+$).

Step B: A mixture of (6-bromo-quinolin-2-yl)-(R)-indan-1-yl-amine (339 mg, 1.0 mmol), commercially available 4-amino-morpholine (204 mg, 2.0 mmol), 2-di-tert-butylphosphino-2',4',6'-triisopropylbiphenyl (tert-butyl X-PHOS) (68 mg, 0.16 mmol), tris(dibenzylideneacetone) dipalladium (0) (37 mg, 0.04 mmol), sodium tert.-butylate (106 mg, 1.1 mmol) and dioxane (6 mL) was heated in a sealed tube at 120° C. for 18 h. The reaction mixture was purified by flash chromatography on silica gel (ethyl acetate/heptane) and crystallization (diethyl ether/heptane) to yield the title compound (72 mg, 20%) as off-white solid. MS (ISP): m/e=361.3 (M+H$^+$); m.p. 152° C.

Example 164

N$^2$—(R)-Indan-1-yl-N6-(4-methyl-piperazin-1-yl)-quinoline-2,6-diamine

The title compound, yellow oil, MS (ISP): m/e=374.4 (M+H$^+$), was prepared in accordance with the general method of example 163, step B from (6-bromo-quinolin-2-yl)-(R)-indan-1-yl-amine (see example 163, step A) and commercially available 1-amino-4-methyl-piperazine.

Example 165

(R)-Indan-1-yl-[6-(4-methyl-piperazin-1-yl)-quinolin-2-yl]-amine

The title compound, brown oil, MS (ISP): m/e=359.3 (M+H$^+$), was prepared in accordance with the general method of example 163, step B from (6-bromo-quinolin-2-yl)-(R)-indan-1-yl-amine (see example 163, step A) and commercially available 1-methyl-piperazine.

Example 166

N-[2-((R)-Indan-1-ylamino)-quinolin-6-yl]-N',N''-diisopropyl-guanidine (R)—N-2-indan-1-yl-quinoline-2,6-diamine (0.10 g, 0.36 mmol) and N,N'-diisopropylcarbodiimide (0.046 mg, 0.36 mmol) were dissolved in toluene (3 mL) and stirred at 100° C. for 16 h. The reaction mixture was evaporated and the residue was subjected to column chromatography (silica gel, heptane/ethyl acetate, 4:1, 2:1, 1:1) to yield the title compound (0.027 g, 19%) as a light brown foam; MS: m/e=402.7 (M+H$^+$).

Example 167

[2-((R)-Indan-1-ylamino)-quinolin-6-yl]-carbamic acid 1-methyl-piperidin-4-yl ester The title compound was prepared in accordance with the general method 11 described in example 138 from triethylamine, 4-chlorocarbonyloxy-1-methylpiperidine hydrochloride (CAS no: 127595-09-9) and (R)—N$^2$-indan-1-yl-quinoline-2,6-diamine; MS: m/e=215.3 (M+H$^+$).

Example 168

1-[2-((R)-Indan-1-ylamino)-quinolin-6-yl]-3-((3-exo)-9-isopropyl-9-aza-bicyclo[3.3.1]non-3-yl)-urea Step A: 9-Isopropyl-9-aza-bicyclo[3.3.1]nonan-3-one oxime: A mixture of 9-isopropyl-9-aza-bicyclo[3.3.1]nonan-3-one (CAS no: 56258-85-6) (5.0 g, 28 mmol) in ethanol (125 mL) and pyridine (3.3 mL, 41 mmol) with hydroxylamine hydrochloride (2.03 g, 29 mmol) was refluxed for 6 h. Cooled to 23° C., the precipitate was filtered off, washed with diethyl ether leaving a solid, which was partitioned between dichloromethane and sodium carbonate solution, the organic layers dried over Na$_2$SO$_4$, filtered and the solvents evaporated to give the title compound as a white solid. (4.43 g, 82%); MS: m/e=197.1 (M+H$^-$).

Step B: (3-exo)-9-Isopropyl-9-aza-bicyclo[3.3.1]non-3-ylamine dihydrochloride: A solution of the above described 9-isopropyl-9-aza-bicyclo[3.3.1]nonan-3-one oxime (1.96 g, 10 mmol) was treated with sodium in pentanol, followed by aqueous workup and HCl salt generation as described in Example 99 Step B. Obtained the title compound as white crystals (2.41 g, 94%); MS: m/e=183.2 (M+H$^+$).

Step C: The title compound was prepared in accordance with the general method 4 described in example 16 from bis(trichloromethyl) carbonate (49 mg, 0.17 mmol), the above described (3-exo)-9-isopropyl-9-aza-bicyclo[3.3.1]non-3-ylamine dihydrochloride (93 mg, 0.363 mmol) and (R)—N$^2$-indan-1-yl-quinoline-2,6-diamine (100 mg, 0.363 mmol); obtained as a white solid (74 mg, 42%); MS: m/e=484.3 (M+H$^+$).

Example 169

1-((3-exo)-8-Cyclopropyl-8-aza-bicyclo[3.2.1]oct-3-yl)-3-[2-((R)-indan-1-ylamino)-quinolin-6-yl]-1-methyl-urea Step A: (3-exo)-(8-Cyclopropyl-8-aza-bicyclo[3.2.1]oct-3-yl)-carbamic acid ethyl ester: To a mixture of (3-exo)-8-cyclopropyl-8-aza-bicyclo[3.2.1]oct-3-ylamine dihydrochloride (Example 99, Step B) (1.0 g, 4.18 mmol) and K$_2$CO$_3$ (2.022 g, 14.63 mmol) in Methanol (10 mL) was added ethyl chloroformate (0.44 mL, 4.59 mmol) and the mixture was stirred at 23° C. for 16 h. Added 15% NaOH solution, stirred 15 min and filtered the solids off, to the filtrate was added solid Na$_2$SO$_4$, filtered and the solvents were evaporated to give the title compound as a white solid. (0.91 g, 91%); MS: m/e=239.2 (M+H$^+$).

Step B: (3-exo)-(8-Cyclopropyl-8-aza-bicyclo[3.2.1]oct-3-yl)-methyl-amine: A mixture of the above described (3-exo)-(8-cyclopropyl-8-aza-bicyclo[3.2.1]oct-3-yl)-carbamic acid ethyl ester (910 mg, 3.81 mmol) in tetrahydrofuran (10 mL) with lithium aluminum hydride (362 mg, 9.54 mmol) was refluxed for 16 h. Cooled to 0° C., added water (0.362 mL), then at 23° C. 15% NaOH solution (1.086 mL), then again water (0.362 mL), stirred at 23° C. for 30 min, filtered the solid off, washed with tetrahydrofuran, the filtrate was evaporated to give the title compound as a colorless oil (0.55 g, 80%); MS: m/e=150.3 (M–Me–NH$_2$+H$^+$).

Step C: The title compound was prepared in accordance with the general method 4 described in example 16 from bis(trichloromethyl) carbonate (352 mg, 5.81 mmol), the above described (3-exo)-(8-cyclopropyl-8-aza-bicyclo

[3.2.1]oct-3-yl)-methyl-amine (524 mg, 2.9 mmol) and (R)—N²-indan-1-yl-quinoline-2,6-diamine (800 mg, 2.9 mmol); obtained as a white solid (90 mg, 6%); MS: m/e=482.3 (M+H$^+$).

Example 170

1-[2-((R)-Indan-1-ylamino)-quinolin-6-yl]-3-((3-exo)-8-isopropyl-8-aza-bicyclo[3.2.1]oct-3-yl)-urea Step A: 8-Isopropyl-8-aza-bicyclo[3.2.1]octan-3-one oxime: A mixture of 8-isopropyl-8-aza-bicyclo[3.2.1]octan-3-one (CAS no: 3423-28-7) (20.0 g, 120 mmol) in ethanol (500 mL) and pyridine (14.5 mL, 179 mmol) with hydroxylamine hydrochloride (8.81 g, 127 mmol) was refluxed for 16 h. Cooled to 23° C., the precipitate was filtered off, washed with diethyl ether leaving a solid, which was partitioned between dichloromethane and sodium carbonate solution, the organic layers dried over Na$_2$SO$_4$, filtered and the solvents evaporated to give the title compound as a white solid. (17.7 g, 82%); MS: m/e=183.2 (M+H$^+$).

Step B: (3-exo)-8-Isopropyl-8-aza-bicyclo[3.2.1]oct-3-ylamine dihydrochloride: A solution of the above described 8-isopropyl-8-aza-bicyclo[3.2.1]octan-3-one oxime (4.31 g, 24 mmol) was treated with sodium in pentanol, followed by aqueous workup and HCl salt generation as described in Example 99 Step B. Obtained the title compound as white crystals (5.7 g, 100%); MS: m/e=169.2 (M+H$^+$).

Step C: 1-[2-((R)-Indan-1-ylamino)-quinolin-6-yl]-3-((3-exo)-8-isopropyl-8-aza-bicyclo[3.2.1]oct-3-yl)-urea: To a solution of (R)—N²-indan-1-yl-quinoline-2,6-diamine (275 mg, 1.0 mmol) and pyridine (80.5 uL, 1.0 mmol) in dichloromethane (5 mL) at 0° C. was added 4-nitrophenyl chloroformate (202 mg, 1.0 mmol) and the mixture was stirred at 23° C. for 1.5 h resulting in a yellow suspension. Added the above described (3-exo)-8-isopropyl-8-aza-bicyclo[3.2.1]oct-3-ylamine dihydrochloride (241 mg, 1.0 mmol) and diisopropylethylamine (600 uL, 3.5 mmol) and dichloromethane (2 mL) and the clear solution was stirred at 23° C. for 2 days. Diluted with ethyl acetate, (150 mL), washed with 1 M Na$_2$CO$_3$-sol. (2×50 mL), 1 M NaOH-sol. (50 mL) and brine (50 mL), dried over Na$_2$SO$_4$. Removal of the solvent in vacuum left a brown foam, which after silica gel column chromatography was crystallized from dichloromethane/diethyl ether to give the title compound as a light grey solid (160 mg, 34%); MS: m/e=470.5 (M+H$^+$).

Example 171

[2-((R)-Indan-1-ylamino)-quinolin-6-yl]-carbamic acid methyl ester

To a solution of (R)—N²-indan-1-yl-quinoline-2,6-diamine (1.2 g, 4.36 mmol) and pyridine (0.35 mL, 4.36 mmol) in dichloromethane (25 mL) at 0° C. was added 4-nitrophenyl chloroformate (878 mg, 4.6 mmol) and the mixture was stirred at 23° C. for 2 h resulting in a yellow suspension. Added tetrahydrofuran, filtered the solid off, dissolved in dichloromethane and methanol, coated on silica gel. Removal of the solvent in vacuum left a brown foam, which after silica gel column chromatography was crystallized from dichloromethane/diethyl ether to give the title compound as a yellow foam (500 mg, 34%); MS: m/e=334.2 (M+H$^+$).

Example 172 rac-N²-(7-Methoxy-indan-1-yl)-quinoline-2,6-diamine

Step A: rac-7-Methoxy-indan-1-ylamine: A mixture of 7-methoxy-indan-1-one oxime (CAS no: 908108-58-7, (E)-oxime 179899-16-2) (4.59 g, 25.9 mmol) in ethanol (500 mL) with 10% palladium on carbon (4.59 g) was hydrogenated at 23° C. and atmospheric pressure for 16 h. Filtered the catalyst off, washed with ethanol, evaporated the filtrate totally and dried in high vacuum to give the title compound as a brown oil (2.7 g, 64%); MS: m/e=164.2 (M+H$^+$).

Step B: rac-(7-Methoxy-indan-1-yl)-(6-nitro-quinolin-2-yl)-amine: A mixture of 2-chloro-6-nitro-quinoline (1.8 g, 8.62 mmol) in 1-methyl-2-pyrrolidone (5 mL) with the above described 7-methoxy-indan-1-ylamine (1.69 g, 10.35 mmol) and N-ethyldiisopropylamine (2.22 mL, 12.94 mmol) was stirred at 140° C. for 2 h. Cooled to 23° C., poured onto water and extracted twice with ethyl acetate, dried over Na$_2$SO$_4$ and evaporated totally to give a crude product which was purified by silica gel column chromatography with heptane/dichloromethane followed by trituration with diethyl ether to give the title compound as a yellow solid (2.3 g, 80%); MS: m/e=336.3 (M+H$^+$).

Step C: rac-N²-(7-methoxy-indan-1-yl)-quinoline-2,6-diamine: Prepared from the above described rac-(7-methoxy-indan-1-yl)-(6-nitro-quinolin-2-yl)-amine (2.3 g, 6.85 mmol) according to step B in general example 2 and obtained the title compound as a light brown solid (1.5 g, 71%); MS: m/e=306.2 (M+H$^+$).

Example 173 rac-N²-(4-Methoxy-2,3-dihydro-benzofuran-3-yl)-quinoline-2,6-diamine

Step A: 4-Methoxy-benzofuran-3-one oxime: A mixture of 4-methoxy-benzofuran-3-one (CAS no: 7169-35-9) (4.9 g, 19 mmol), sodium acetate (3.06 g, 38 mmol) and hydroxylamine hydrochloride (2.58 g, 38 mmol) in ethanol (40 mL) was refluxed for 6 h. Cooled to 23° C., filtered the precipitate off, washed with ethanol and dried in high vacuum to give the title compound as a white solid (5.93 g, 100%); MS: m/e=180.2 (M+H$^+$).

Step B: rac-4-Methoxy-2,3-dihydro-benzofuran-3-ylamine: A mixture of the above described 4-methoxy-benzofuran-3-one oxime (6.15 g, 34.3 mmol) in ethanol (500 mL) with 10% palladium on carbon (6.15 g) was hydrogenated at 23° C. and atmospheric pressure for 18 h. Filtered the catalyst off, washed with ethanol, evaporated the filtrate totally and dried in high vacuum to give the title compound as a light yellow oil (3.65 g, 64%); MS: m/e=166.2 (M+H$^-$).

Step C: rac-(4-Methoxy-2,3-dihydro-benzofuran-3-yl)-(6-nitro-quinolin-2-yl)-amine: A mixture of 2-chloro-6-nitro-quinoline (3.8 g, 18.2 mmol) in 1-methyl-2-pyrrolidone (5 mL) with the above described rac-4-methoxy-2,3-dihydro-benzofuran-3-ylamine (3.61 g, 21.9 mmol) and N-ethyldiisopropylamine (4.68 mL, 27.3 mmol) was stirred at 140° C. for 2 h. Cooled to 23° C., poured onto water and extracted twice with ethyl acetate, dried over Na$_2$SO$_4$ and evaporated totally to give a crude product which was purified by silica gel column chromatography with heptane/dichloromethane followed by trituration with diethyl ether to give the title compound as a yellow solid (4.0 g, 65%); MS: m/e=336.3 (M+H$^+$).

Step D: rac-N$^2$-(4-Methoxy-2,3-dihydro-benzofuran-3-yl)-quinoline-2,6-diamine: Prepared from the above described rac-(4-methoxy-2,3-dihydro-benzofuran-3-yl)-(6-nitro-quinolin-2-yl)-amine (3.9 g, 11.6 mmol) according to step B in general example 2 and obtained the title compound as a light brown solid (2.7 g, 76%); MS: m/e=308.2 (M+H$^+$).

Example 174 rac-N$^2$-[4-(2-Methoxy-ethoxy)-2,3-dihydro-benzofuran-3-yl]-quinoline-2,6-diamine Step A: 4-(2-Methoxy-ethoxy)-benzofuran-3-one: A mixture of 4-hydroxy-benzofuran-3-one (CAS no: 19278-81-0) (4.9 g, 9 mmol), potassium carbonate (1.66 g, 12 mmol) and 2-bromoethyl methylether (1.13 mL, 12 mmol) in N,N-dimethylformamide (20 mL) was stirred at 80° C. for 1.5 h. Cooled to 23° C., poured into 1 N HCl, extracted four times with ethyl acetate, dried combined organic layer over Na$_2$SO$_4$. Removal of the solvent in vacuum left a yellow residue which was purified by silica gel column chromatography with heptane/ethyl acetate to give the title compound as a white solid (1.3 g, 63%); MS: m/e=177.2 (M−OMe+H$^+$).

Step B: 4-(2-Methoxy-ethoxy)-benzofuran-3-one oxime: A mixture of the above described 4-(2-methoxy-ethoxy)-benzofuran-3-one (1.9 g, 9 mmol), sodium acetate (1.5 g, 19 mmol) and hydroxylamine hydrochloride (1.3 g, 19 mmol) in ethanol (15 mL) was refluxed for 4 h. Cooled to 23° C., filtered the precipitate off, washed with water and ethanol and dried in high vacuum to give the title compound as a white solid (1.45 g, 71%); MS: m/e=224.1 (M+H$^-$).

Step C: rac-4-(2-Methoxy-ethoxy)-2,3-dihydro-benzofuran-3-ylamine: A mixture of the above described 4-(2-methoxy-ethoxy)-benzofuran-3-one oxime (1.19 g, 5 mmol) in methanol (100 mL) and tetrahydrofuran (100 mL) with 10% palladium on carbon (1.42 g) was hydrogenated at 23° C. and atmospheric pressure for 5 days. Filtered the catalyst off, washed with tetrahydrofuran, evaporated the filtrate totally and dried in high vacuum to give the title compound as a red oil (1.15 g, 90%, ca. 90% purity, contains residual starting material); MS: m/e=193.1 (M−NH$_2$+H$^+$).

Step D: rac-[4-(2-Methoxy-ethoxy)-2,3-dihydro-benzofuran-3-yl]-(6-nitro-quinolin-2-yl)-amine: A mixture of 2-chloro-6-nitro-quinoline (1.04 g, 5.0 mmol) in 1-methyl-2-pyrrolidone (10 mL) with the above described rac-4-(2-methoxy-ethoxy)-2,3-dihydro-benzofuran-3-ylamine (1.14 g, 5.5 mmol) and N-ethyldiisopropylamine (1.27 mL, 7.5 mmol) was stirred at 140° C. for 2 h. Cooled to 23° C., poured onto water and extracted twice with ethyl acetate, dried over Na$_2$SO$_4$ and evaporated totally to give a crude product which was purified by silica gel column chromatography with heptane/dichloromethane followed by trituration with diethyl ether to give the title compound as an orange solid (1.24 g, 65%); MS: m/e=382.3 (M+H$^-$).

Step E: rac-N$^2$-[4-(2-Methoxy-ethoxy)-2,3-dihydro-benzofuran-3-yl]-quinoline-2,6-diamine: Prepared from the above described rac-[4-(2-methoxy-ethoxy)-2,3-dihydro-benzofuran-3-yl]-(6-nitro-quinolin-2-yl)-amine (1.24 g, 3.25 mmol) according to step B in general example 2 and obtained the title compound as a light brown foam (0.80 g, 70%); MS: m/e=352.3 (M+H$^+$).

Example 175 rac-N$^2$-(4-Ethoxy-2,3-dihydro-benzofuran-3-yl)-quinoline-2,6-diamine

Step A: 4-Ethoxy-benzofuran-3-one oxime: A mixture of 4-ethoxy-benzofuran-3-one (CAS no: 7169-36-0) (4.18 g, 23.5 mmol), sodium acetate (3.96 g, 48.3 mmol) and hydroxylamine hydrochloride (3.34 g, 48.1 mmol) in ethanol (30 mL) was refluxed for 16 h. Cooled to 23° C., diluted with water (50 mL), filtered the precipitate off, washed with water, ethanol and diethyl ether and dried in high vacuum to give the title compound as a white solid (4.2 g, 93%); MS: m/e=194.3 (M+H$^+$).

Step B: rac-4-Ethoxy-2,3-dihydro-benzofuran-3-ylamine: A mixture of the above described 4-ethoxy-benzofuran-3-one oxime (4.2 g, 21.7 mmol) in ethanol (200 mL) and tetrahydrofuran (200 mL) with 10% palladium on carbon (4.0 g) was hydrogenated at 23° C. and atmospheric pressure for 18 h. Filtered the catalyst off, washed with ethanol, evaporated the filtrate totally and dried in high vacuum to give the title compound as a light brown solid (3.7 g, 1:1 mixture of product and starting material); MS: m/e=163.3 (M+H$^+$).

Step C: rac-(4-Methoxy-2,3-dihydro-benzofuran-3-yl)-(6-nitro-quinolin-2-yl)-amine: A mixture of 2-chloro-6-nitro-quinoline (2.0 g, 9.6 mmol) in 1-methyl-2-pyrrolidone (5 mL) with the above described rac-4-ethoxy-2,3-dihydro-benzofuran-3-ylamine (3.78 g, ca. 10 mmol, max. 50% purity) and N-ethyldiisopropylamine (2.45 mL, 14.4 mmol) was stirred at 140° C. for 2 h. Cooled to 23° C., poured onto water and extracted twice with ethyl acetate, dried over Na$_2$SO$_4$ and evaporated totally to give a crude product which was purified by silica gel column chromatography with heptane/dichloromethane followed by trituration with diethyl ether to give the title compound as a yellow solid (0.60 g, 18%); MS: m/e=352.4 (M+H$^+$).

Step D: rac-N$^2$-(4-Ethoxy-2,3-dihydro-benzofuran-3-yl)-quinoline-2,6-diamine: Prepared from the above described rac-(4-ethoxy-2,3-dihydro-benzofuran-3-yl)-(6-nitro-quinolin-2-yl)-amine (0.6 g, 1.7 mmol) according to step B in general example 2 and obtained the title compound as a light brown solid (0.26 g, 45%); MS: m/e=322.2 (M+H$^+$).

Example 176

3-[2-((R)-Indan-1-ylamino)-quinolin-6-yl]-1-(1-isopropyl-piperidin-4-yl)-1-methyl-urea The title compound was prepared from (R)—N$^2$-indan-1-yl-quinoline-2,6-diamine (275 mg, 1.0 mmol), 4-nitrophenyl chloroformate (202 mg, 1.0 mmol) and (1-isopropyl-piperidin-4-yl)-methyl-amine dihydrochloride (CAS no: of free base 503126-34-9) (229 mg, 1.0 mmol) in accordance with the general method 4 described in example 170 step C and was obtained as an off-white solid (186 mg, 41%); MS: m/e=458.3 (M+H$^+$).

Example 177

3-[2-((R)-Indan-1-ylamino)-quinolin-6-yl]-1-methyl-1-((3-exo)-8-methyl-8-aza-bicyclo[3.2.1]oct-3-yl)-urea Step A: (3-exo)-(8-Methyl-8-aza-bicyclo[3.2.1]oct-3-yl)-carbamic acid ethyl ester: To a mixture of (3-exo)-8-methyl-8-aza-bicyclo[3.2.1]oct-3-ylamine dihydrochloride (CAS no: 340682-25-9) (0.533 g, 2.5 mmol) and K$_2$CO$_3$ (1.036 g, 7.5 mmol) in water (5 mL) at 0° C. was added ethyl chloroformate (0.262 mL, 2.75 mmol) and the mixture was stirred at 23° C. for 16 h. The reaction mixture saturated with solid NaCl, extracted five times with dichloromethane, the combined organic layers were dried over Na$_2$SO$_4$, filtered and the solvents evaporated to give the title compound as a white solid. (0.257 g, 48%); MS: m/e=213.2 (M+H$^+$).

Step B: (3-exo)-Methyl-(8-methyl-8-aza-bicyclo[3.2.1]oct-3-yl)-amine: A mixture of the above described (3-exo)-(8-methyl-8-aza-bicyclo[3.2.1]oct-3-yl)-carbamic acid ethyl ester (257 mg, 1.21 mmol) in tetrahydrofuran (5 mL) with lithium aluminum hydride (115 mg, 3.03 mmol) was refluxed for 16 h. Cooled to 0° C., added water (0.115 mL), then at 23° C. 15% NaOH solution (0.345 mL), then again water (0.115 mL), stirred at 23° C. for 30 min, filtered the solid off, washed with tetrahydrofuran, the filtrate was evaporated to give the title compound as a light yellow oil (0.175 g, 94%); MS: m/e=155.2 (M+H$^+$).

Step C: The title compound was prepared from (R)—N$^2$-indan-1-yl-quinoline-2,6-diamine (79 mg, 0.285 mmol), 4-nitrophenyl chloroformate (58 mg, 0.285 mmol) and the above described (3-exo)-methyl-(8-methyl-8-aza-bicyclo[3.2.1]oct-3-yl)-amine (44 mg, 0.285 mmol) in accordance with the general method 4 described in example 170 step C and was obtained as an off-white solid (35 mg, 27%); MS: m/e=456.3 (M+H$^+$).

Example 178

1-[2-((R)-Indan-1-ylamino)-quinolin-6-yl]-3-((7-exo)-9-isopropyl-3-oxa-9-aza-bicyclo[3.3.1]non-7-yl)-urea Step A: 9-Isopropyl-3-oxa-9-aza-bicyclo[3.3.1]nonan-7-one oxime: A mixture of 9-isopropyl-3-oxa-9-aza-bicyclo[3.3.1]nonan-7-one (CAS no: 99189-30-7)(1.25 g, 6.82 mmol) in ethanol (40 mL) and pyridine (0.8 mL, 10.2 mmol) with hydroxylamine hydrochloride (0.5 g, 7.23 mmol) was refluxed for 6 h. Cooled to 23° C., evaporated all volatiles, partitioned the residue between dichloromethane and sodium carbonate solution, reextracted the aqueous layer with tetrahydrofuran/ethyl acetate, all combined organic layers were dried over Na$_2$SO$_4$, filtered and the solvents evaporated to give the title compound as a dark brown solid. (1.0 g, 74%); MS: m/e=199.1 (M+H$^+$).

Step B: (7-exo)-9-Isopropyl-3-oxa-9-aza-bicyclo[3.3.1]non-7-ylamine dihydrochloride: A solution of the above described 9-isopropyl-3-oxa-9-aza-bicyclo[3.3.1]nonan-7-one oxime (0.99 g, 4.99 mmol) was treated with sodium in pentanol, followed by aqueous workup and HCl salt generation as described in Example 99 Step B. Obtained the title compound as an off-white solid (0.69 g, 54%); MS: m/e=185.2 (M+H$^+$).

Step C: 1-[2-((R)-Indan-1-ylamino)-quinolin-6-yl]-3-((7-exo)-9-isopropyl-3-oxa-9-aza-bicyclo[3.3.1]non-7-yl)-urea: The title compound was prepared from (R)—N$^2$-indan-1-yl-quinoline-2,6-diamine (275 mg, 1.0 mmol), 4-nitrophenyl chloroformate (202 mg, 1.0 mmol) and the above described (7-exo)-9-isopropyl-3-oxa-9-aza-bicyclo[3.3.1]non-7-ylamine dihydrochloride (257 mg, 1.0 mmol) in accordance with the general method 4 described in example 170 step C and was obtained as an off-white solid (109 mg, 22%); MS: m/e=486.2 (M+H$^+$).

Example 179 rac-1-(1-Isopropyl-piperidin-4-yl)-3-[2-(7-methoxy-indan-1-ylamino)-quinolin-6-yl]-1-methyl-urea The title compound was prepared from rac-N$^2$-(7-methoxy-indan-1-yl)-quinoline-2,6-diamine (Example 172) (153 mg, 0.5 mmol), 4-nitrophenyl chloroformate (101 mg, 0.5 mmol) and (1-isopropyl-piperidin-4-yl)-methyl-amine dihydrochloride (CAS no: of free base 503126-34-9) (115 mg, 0.5 mmol) in accordance with the general method 4 described in example 170 step C and was obtained as an off-white solid (122 mg, 50%); MS: m/e=488.2 (M+H$^+$).

Example 180 rac-1-(1-Isopropyl-piperidin-4-yl)-3-[2-(4-methoxy-2,3-dihydro-benzofuran-3-ylamino)-quinolin-6-yl]-urea The title compound was prepared from rac-N$^2$-(4-methoxy-2,3-dihydro-benzofuran-3-yl)-quinoline-2,6-diamine (Example 173) (200 mg, 0.62 mmol), 4-nitrophenyl chloroformate (125 mg, 0.62 mmol) and 1-isopropyl-piperidin-4-ylamine dihydrochloride (CAS no: 534596-29-7) (140 mg, 0.65 mmol) in accordance with the general method 4 described in example 170 step C and was obtained as an off-white solid (190 mg, 61%); MS: m/e=476.2 (M+H$^+$).

Example 181 rac-1-[2-(4-Ethoxy-2,3-dihydro-benzofuran-3-ylamino)-quinolin-6-yl]-3-(1-isopropyl-piperidin-4-yl)-urea The title compound was prepared from rac-N$^2$-(4-ethoxy-2,3-dihydro-benzofuran-3-yl)-quinoline-2,6-diamine (Example 175) (200 mg, 0.62 mmol), 4-nitrophenyl chloroformate (125 mg, 0.62 mmol) and 1-isopropyl-piperidin-4-ylamine dihydrochloride (CAS no: 534596-29-7) (134 mg, 0.62 mmol) in accordance with the general method 4 described in example 170 step C and was obtained as an off-white solid (190 mg, 62%); MS: m/e=490.1 (M+H$^+$).

Example 182 rac-1-(1-Isopropyl-piperidin-4-yl)-3-{2-[4-(2-methoxy-ethoxy)-2,3-dihydro-benzofuran-3-ylamino]-quinolin-6-yl}-urea The title compound was prepared from rac-N$^2$-[4-(2-methoxy-ethoxy)-2,3-dihydro-benzofuran-3-yl]-quinoline-2,6-diamine (Example 174) (200 mg, 0.57 mmol), 4-nitrophenyl chloroformate (115 mg, 0.57 mmol) and 1-isopropyl-piperidin-4-ylamine dihydrochloride (CAS no: 534596-29-7) (122 mg, 0.57 mmol) in accordance with the general method 4 described in example 170 step C and was obtained as an off-white solid (210 mg, 71%); MS: m/e=520.5 (M+H$^+$).

Example 183 rac-N-[2-(4-Methoxy-2,3-dihydro-benzofuran-3-ylamino)-quinolin-6-yl]-2-(4-methyl-piperazin-1-yl)-acetamide The title compound was prepared from rac-N$^2$-(4-methoxy-2,3-dihydro-benzofuran-3-yl)-quinoline-2,6-diamine (Example 173) (150 mg, 0.59 mmol) and commercially available (4-methyl-piperazin-1-yl)-acetic acid (77 mg, 0.68 mmol) in accordance with the general method 14 described in example 119 and was obtained as an off-white solid (210 mg, 96%); MS: m/e=448.3 (M+H$^+$).

Example 184 rac-N-[2-(4-Ethoxy-2,3-dihydro-benzofuran-3-ylamino)-quinolin-6-yl]-2-(4-methyl-piperazin-1-yl)-acetamide The title compound was prepared from rac-$N^2$-(4-ethoxy-2,3-dihydro-benzofuran-3-yl)-quinoline-2,6-diamine (Example 175) (200 mg, 0.49 mmol) and commercially available (4-methyl-piperazin-1-yl)-acetic acid (74 mg, 0.65 mmol) in accordance with the general method 14 described in example 119 and was obtained as an off-white solid (200 mg, 93%); MS: m/e=462.2 (M+H$^+$).

Example 185 rac-N-{2-[4-(2-Methoxy-ethoxy)-2,3-dihydro-benzofuran-3-ylamino]-quinolin-6-yl}-2-(4-methyl-piperazin-1-yl)-acetamide The title compound was prepared from rac-$N^2$-[4-(2-methoxy-ethoxy)-2,3-dihydro-benzofuran-3-yl]-quinoline-2,6-diamine (Example 174) (200 mg, 0.4 mmol) and commercially available (4-methyl-piperazin-1-yl)-acetic acid (68 mg, 0.6 mmol) in accordance with the general method 14 described in example 119 and was obtained as an off-white solid (160 mg, 76%); MS: m/e=492.3 (M+H$^+$).

Example 186 rac-1-((3-exo)-8-Isopropyl-8-aza-bicyclo[3.2.1]oct-3-yl)-3-[2-(7-methoxy-indan-1-ylamino)-quinolin-6-yl]-urea The title compound was prepared from rac-$N^2$-(7-methoxy-indan-1-yl)-quinoline-2,6-diamine (Example 172) (153 mg, 0.5 mmol), 4-nitrophenyl chloroformate (101 mg, 0.5 mmol) and (3-exo)-8-isopropyl-8-aza-bicyclo[3.2.1]oct-3-ylamine dihydrochloride (Example 170 step B) (121 mg, 0.5 mmol) in accordance with the general method 4 described in example 170 step C and was obtained as an off-white solid (42 mg, 17%); MS: m/e=500.1 (M+H$^+$).

Example 187 rac-3-[2-(5-Fluoro-indan-1-ylamino)-quinolin-6-yl]-1-(1-isopropyl-piperidin-4-yl)-1-methyl-urea The title compound was prepared from rac-$N^2$-(5-fluoro-indan-1-yl)-quinoline-2,6-diamine (Example 106) (200 mg, 0.681 mmol), 4-nitrophenyl chloroformate (137 mg, 0.681 mmol) and (1-isopropyl-piperidin-4-yl)-methyl-amine dihydrochloride (CAS no: of free base 503126-34-9) (156 mg, 0.681 mmol) in accordance with the general method 4 described in example 170 step C and was obtained as an off-white solid (260 mg, 80%); MS: m/e=476.3 (M+H$^+$).

Example 188 rac-1-((3-exo)-8-Isopropyl-8-aza-bicyclo[3.2.1]oct-3-yl)-3-[2-(7-methoxy-indan-1-ylamino)-quinolin-6-yl]-1-methyl-urea Step A: (3-exo)-(8-Isopropyl-8-aza-bicyclo[3.2.1]oct-3-yl)-carbamic acid ethyl ester: To a mixture of (3-exo)-8-isopropyl-8-aza-bicyclo[3.2.1]oct-3-ylamine dihydrochloride (Example 170 step B) (1.2 mg, 5.0 mmol) and K$_2$CO$_3$ (2.07 g, 15 mmol) in water (10 mL) at 0° C. was added ethyl chloroformate (0.524 mL, 5.5 mmol) and the mixture was stirred at 23° C. for 16 h. The reaction mixture saturated with solid sodium chloride, extracted five times with dichloromethane, the combined organic layers were dried over Na$_2$SO$_4$, filtered and the solvents evaporated to give the title compound as a light yellow solid. (0.820 g, 68%); MS: m/e=241.2 (M+H$^+$).

Step B: (3-exo)-(8-Isopropyl-8-aza-bicyclo[3.2.1]oct-3-yl)-methyl-amine: A mixture of the above described (3-exo)-(8-isopropyl-8-aza-bicyclo[3.2.1]oct-3-yl)-carbamic acid ethyl ester (900 mg, 3.75 mmol) in tetrahydrofuran (15 mL) with lithium aluminum hydride (355 mg, 9.36 mmol) was refluxed for 16 h. Cooled to 0° C., added water (0.355 mL), then at 23° C. 15% NaOH solution (1.065 mL), then again water (0.355 mL), stirred at 23° C. for 30 min, filtered the solid off, washed with tetrahydrofuran, the filtrate was evaporated to give the title compound as a light yellow oil (0.680 g, 100%); MS: m/e=183.2 (M+H$^+$).

Step C: The title compound was prepared from rac-$N^2$-(7-methoxy-indan-1-yl)-quinoline-2,6-diamine (Example 172) (153 mg, 0.5 mmol), 4-nitrophenyl chloroformate (101 mg, 0.5 mmol) and the above described (3-exo)-(8-isopropyl-8-aza-bicyclo[3.2.1]oct-3-yl)-methyl-amine (91 mg, 0.5 mmol) in accordance with the general method 4 described in example 170 step C and was obtained as a yellow solid (68 mg, 26%); MS: m/e=514.2 (M+H$^+$).

Example 189 rac-1-[1-(2-Hydroxy-ethyl)-piperidin-4-yl]-3-[2-(7-methoxy-indan-1-ylamino)-quinolin-6-yl]-urea The title compound was prepared from rac-$N^2$-(7-methoxy-indan-1-yl)-quinoline-2,6-diamine (Example 172) (200 mg, 0.655 mmol), 4-nitrophenyl chloroformate (132 mg, 0.655 mmol) and commercially available 4-amino-1-piperidine ethanol (94 mg, 0.655 mmol) in accordance with the general method 4 described in example 170 step C and was obtained as an off-white solid (160 mg, 26%); MS: m/e=476.2 (M+H$^+$).

Example 190 rac-Cyclopropanecarboxylic acid [2-(6-fluoro-indan-1-ylamino)-quinolin-6-yl]-amide The title compound was prepared in accordance with the general method 14 described in example 119 from rac-$N^2$-(6-fluoro-indan-1-yl)-quinoline-2,6-diamine and cyclopropanecarboxylic acid; MS: m/e=362.4 (M+H$^-$).

Example 191 rac-1-[1-(2-Hydroxy-2-methyl-propyl)-piperidin-4-yl]-3-[2-(7-methoxy-indan-1-ylamino)-quinolin-6-yl]-1-methyl-urea Step A: [1-(2-Hydroxy-2-methyl-propyl)-piperidin-4-yl]-carbamic acid ethyl ester: A mixture of commercially available ethyl piperidin-4-ylcarbamate (2.067 g, 12 mmol) and isobutylene oxide (868 mg, 12 mmol) in ethanol (15 mL) was irradiated in a microwave apparatus at 110° C. for 90 min. Purification by silica gel column chromatography with ethyl acetate gave the title compound as a colorless oil (2.838 g, 97%); MS: m/e=245.3 (M+H$^+$).

Step B: 2-Methyl-1-(4-methylamino-piperidin-1-yl)-propan-2-ol: A mixture of the above described [1-(2-hydroxy-2-methyl-propyl)-piperidin-4-yl]-carbamic acid ethyl ester (2.35 g, 10 mmol) in tetrahydrofuran (40 mL) with lithium aluminum hydride (913 mg, 24 mmol) was refluxed for 16 h. Cooled to 0° C., added water (0.913 mL), then at 23° C. 15% NaOH solution (2.739 mL), then again water (0.913 mL), stirred at 23° C. for 30 min, filtered the solid off, washed with tetrahydrofuran, the filtrate was evaporated to give the title compound as a colorless oil (1.80 g, 100%); MS: m/e=187.2 (M+H$^+$).

Step C: The title compound was prepared from rac-N$^2$-(7-methoxy-indan-1-yl)-quinoline-2,6-diamine (Example 172) (305 mg, 1.0 mmol), 4-nitrophenyl chloroformate (202 mg, 1.0 mmol) and the above 2-methyl-1-(4-methylamino-piperidin-1-yl)-propan-2-ol (186 mg, 1.0 mmol) in accordance with the general method 4 described in example 170 step C and was obtained as an off-white solid (286 mg, 55%); MS: m/e=518.2 (M+H$^+$).

Example 192

1-[1-(2-Hydroxy-2-methyl-propyl)-piperidin-4-yl]-3-[2-((R)-indan-1-ylamino)-quinolin-6-yl]-1-methyl-urea The title compound was prepared from (R)—N$^2$-indan-1-yl-quinoline-2,6-diamine (275 mg, 1.0 mmol), 4-nitrophenyl chloroformate (202 mg, 1.0 mmol) and 2-methyl-1-(4-methylamino-piperidin-1-yl)-propan-2-ol (Example 191 step B) (186 mg, 1.0 mmol) in accordance with the general method 4 described in example 170 step C and was obtained as an off-white solid (263 mg, 54%); MS: m/e=488.1 (M+H$^+$).

Example 193 rac-1-(1-Isopropyl-piperidin-4-yl)-3-[2-(4-methoxy-2,3-dihydro-benzofuran-3-ylamino)-quinolin-6-yl]-1-methyl-urea The title compound was prepared from rac-N$^2$-(4-methoxy-2,3-dihydro-benzofuran-3-yl)-quinoline-2,6-diamine (Example 173) (153 mg, 0.5 mmol), 4-nitrophenyl chloroformate (101 mg, 0.5 mmol) and (1-isopropyl-piperidin-4-yl)-methyl-amine dihydrochloride (CAS no: of free base 503126-34-9) (115 mg, 0.5 mmol) in accordance with the general method 4 described in example 170 step C and was obtained as an off-white solid (134 mg, 55%); MS: m/e=490.1 (M+H$^+$).

Example 194 rac-1-((3-exo)-8-Isopropyl-8-aza-bicyclo[3.2.1]oct-3-yl)-3-[2-(4-methoxy-2,3-dihydro-benzofuran-3-ylamino)-quinolin-6-yl]-1-methyl-urea The title compound was prepared from rac N$^2$-(4-methoxy-2,3-dihydro-benzofuran-3-yl)-quinoline-2,6-diamine (Example 173) (154 mg, 0.5 mmol), 4-nitrophenyl chloroformate (101 mg, 0.5 mmol) and (3-exo)-(8-isopropyl-8-aza-bicyclo[3.2.1]oct-3-yl)-methyl-amine (Example 188 step B) (91 mg, 0.5 mmol) in accordance with the general method 4 described in example 170 step C and was obtained as an off-white solid (160 mg, 62%); MS: m/e=516.0 (M+H$^+$).

Example 195 rac-Cyclopropanecarboxylic acid [2-(4-methoxy-2,3-dihydro-benzofuran-3-ylamino)-quinolin-6-yl]-amide The title compound was prepared from rac-N$^2$-(4-methoxy-2,3-dihydro-benzofuran-3-yl)-quinoline-2,6-diamine (Example 173) (154 mg, 0.5 mmol) and commercially available cyclopropanecarboxylic acid (40 ul, 0.5 mmol) in accordance with the general method 14 described in example 119 and was obtained as an off-white solid (68 mg, 36%); MS: m/e=376.3 (M+H$^+$).

Example 196

N-[2-((R)-Indan-1-ylamino)-quinolin-6-yl]-acetamide (R)—N$^2$-indan-1-yl-quinoline-2,6-diamine (551 mg, 2 mmol) was dissolved in acetic acid (5 mL) then acetic anhydride (378 ul, 4 mmol) was added and the mixture was stirred at for 16 h. The reaction mixture was extracted with ethyl acetate and sat. NaHCO$_3$-sol., the organic layers were combined, dried over MgSO$_4$, filtered and the solvents evaporated to give the title compound as a light brown foam (640 mg, 100%); MS: m/e=318.1 (M+H$^+$).

Example 197 rac-1-[2-(5-Fluoro-indan-1-ylamino)-quinolin-6-yl]-3-[1-(2-hydroxy-ethyl)-piperidin-4-yl]-urea The title compound was prepared from rac-N$^2$-(5-fluoro-indan-1-yl)-quinoline-2,6-diamine (Example 106) (240 mg, 0.818 mmol), 4-nitrophenyl chloroformate (165 mg, 0.818 mmol) and commercially available 4-amino-1-piperidine-ethanol (118 mg, 0.818 mmol) in accordance with the general method 4 described in example 170 step C and was obtained as an off-white solid (54 mg, 14%); MS: m/e=464.2 (M+H$^+$).

Example 198

(−)-N-[2-((S)-4-Methoxy-2,3-dihydro-benzofuran-3-ylamino)-quinolin-6-yl]-2-(4-methyl-piperazin-1-yl)-acetamide rac-N-[2-(4-Methoxy-2,3-dihydro-benzofuran-3-ylamino)-quinolin-6-yl]-2-(4-methyl-piperazin-1-yl)-acetamide (Example 183) was separated on chiral preparative HPLC using 30% ethanol in heptane. Obtained as a white solid (71 mg).

Example 199 rac-1-[1-(2-Hydroxy-2-methyl-propyl)-piperidin-4-yl]-3-[2-(4-methoxy-2,3-dihydro-benzofuran-3-ylamino)-quinolin-6-yl]-1-methyl-urea The title compound was prepared from rac-N$^2$-(4-methoxy-2,3-dihydro-benzofuran-3-yl)-quinoline-2,6-diamine (Example 173) (154 mg, 0.5 mmol), 4-nitrophenyl chloroformate (101 mg, 0.5 mmol) and 2-methyl-1-(4-methylamino-piperidin-1-yl)-propan-2-ol (Example 191 step B) (93 mg, 0.5 mmol) in accordance with the general method 4 described in example 170 step C and was obtained as a white solid (39 mg, 15%); MS: m/e=520.0 (M+H⁺).

Example 200 rac-N-2-(6-Fluoro-2,3-dihydro-benzofuran-3-yl)-quinoline-2,6-diamine

Step A: 6-Fluoro-benzofuran-3-one oxime: A mixture of 6-fluoro-benzofuran-3-one (CAS 351528-80-8) (5.93 g, 39 mmol), sodium acetate (6.587 g, 80 mmol) and hydroxylamine hydrochloride (5.553 g, 80 mmol) in ethanol (70 ml) was refluxed for 4 h. Cooled to 23° C., filtered the precipitate off, washed with aqueous ethanol and dried in high vacuum to give the title compound as a white solid (5.19 g, 80%, HPLC 1.489 min); MS (ISN) m/e=168.1 [(M−H)⁻].

Step B: rac-6-Fluoro-2,3-dihydro-benzofuran-3-ylamine: A mixture of the above described 6-fluoro-benzofuran-3-one oxime (5.38 g, 32 mmol; HPLC 1.489 min) and Raney-Nickel (2.4 g) in tetrahydrofuran (125 mL) and methanol (125 mL) was hydrogenated at 100 bar hydrogen-pressure at 50° C. for 18 h. Filtered the catalyst off, washed with methanol and tetrahydrofuran, all volatiles very removed in vacuum to give the crude product which was purified by Si—NH₂ column chromatography with n-heptane/ethyl acetate to give the title compound as a light brown liquid (1.65 g, 34%, HPLC 0.367 min 100%), MS (ISP) m/e=154.0 [(M+H)⁺].

Step C: rac-(6-Fluoro-2,3-dihydro-benzofuran-3-yl)-(6-nitro-quinolin-2-yl)-amine: A mixture of 2-chloro-6-nitro-quinoline (1.6 g, 7.67 mmol) in N-methyl-2-pyrrolidinone (15 ml) with the above described rac-6-fluoro-2,3-dihydro-benzofuran-3-ylamine (1.3 g, 8.43 mmol) and N-ethyldiisopropylamine (1.96 ml, 11.5 mmol) was stirred at 140° C. for 2 h. Cooled to room temperature, poured onto water and extracted twice with Ethyl acetate, dried over sodium sulfate and evaporated totally to give a crude product which was purified by silica gel column chromatography with heptane/dichloromethane followed by trituration with diethyl ether to give the title compound as a yellow solid (1.0 g, 40%); MS (ISP) m/e=326.2 (M+H⁺).

Step D: rac-N-2-(6-Fluoro-2,3-dihydro-benzofuran-3-yl)-quinoline-2,6-diamine: Prepared from the above described rac-(6-fluoro-2,3-dihydro-benzofuran-3-yl)-(6-nitro-quinolin-2-yl)-amine (1.0 g, 3.07 mmol) according to step B in general example 2 and obtained the title compound as a grey solid (0.56 g, 62%); MS (ISP) m/e=296.1 (M+H⁺).

Example 201 rac-N-[2-(7-Fluoro-indan-1-ylamino)-quinolin-6-yl]-2-methoxy-acetamide

The title compound was prepared in accordance with the general method 14 described in example 119 from rac-N-2-(7-fluoro-indan-1-yl)-quinoline-2,6-diamine and methoxy acetic acid; MS: m/e=366.3 (M+H⁺).

Example 202 rac-3-[2-(6-Fluoro-2,3-dihydro-benzofuran-3-ylamino)-quinolin-6-yl]-1-(1-isopropyl-piperidin-4-yl)-1-methyl-urea Prepared from rac-N-2-(6-fluoro-2,3-dihydro-benzofuran-3-yl)-quinoline-2,6-diamine (Example 200) (200 mg, 0.67 mmol), 4-nitrophenyl chloroformate (137 mg, 0.67 mmol) and (1-isopropyl-piperidin-4-yl)-methyl-amine dihydrochloride (CAS of free base 503126-34-9) (140 mg, 0.65 mmol) and diisopropylethyl amine (410 ul, 2.37 mmol) according to the procedure described for Example 170 step C. Obtained the title compound as an off-white solid (250 mg, 77%), MS (ISP) m/e=478.1 [(M+H)⁺].

Example 203 rac-N-[2-(6-Fluoro-2,3-dihydro-benzofuran-3-ylamino)-quinolin-6-yl]-2-(4-methyl-piperazin-1-yl)-acetamide The title compound was prepared in accordance with the general method 14 described in example 119 from rac-N-2-(6-fluoro-2,3-dihydro-benzofuran-3-yl)-quinoline-2,6-diamine (Example 200) (320 mg, 1.08 mmol) and (4-methylpiperazin-1-yl)-acetic acid (171 mg, 1.08 mmol). Obtained as an off-white foam (410 mg, 87%), MS (ISP) m/e=436.2 (M+H⁻).

Example 204

(−)-1-(1-Isopropyl-piperidin-4-yl)-3-[2-(4-methoxy-2,3-dihydro-benzofuran-3-ylamino)-quinolin-6-yl]-1-methyl-urea Rac-1-(1-Isopropyl-piperidin-4-yl)-3-[2-(4-methoxy-2,3-dihydro-benzofuran-3-ylamino)-quinolin-6-yl]-1-methyl-urea (Example 193) was separated on chiral preparative HPLC using 30% ethanol in heptane. Obtained as a light brown solid (43 mg).

Example 205

1-[1-(2-Hydroxy-ethyl)-piperidin-4-yl]-3-[2-((R)-indan-1-ylamino)-quinolin-6-yl]-1-methyl-urea Step A: 2-(4-Methylamino-piperidin-1-yl)-ethanol: To a solution of [1-(2-hydroxy-ethyl)-piperidin-4-yl]-carbamic acid tert-butyl ester (CAS m 558443-53-1) (5.71 g, 23 mmol) in tetrahydrofuran (100 ml) at 23° C. was added in portions lithium aluminum hydride (2.66 g, 70 mmol) and the mixture was stirred at 70° C. for 18 h. Then the reaction was cooled to 0° C., water (2.66 ml) was added very slowly, then NaOH 15% (7.98 ml) and water (2.66 ml). The mixture was stirred at 23° C. for 1.5 h, the precipitate was filtered off, washed with tetrahydrofuran and the organic layer was evaporated totally to give the title compound as a white solid (3.7 g, 100%), MS (ISP) m/e=159.3 [(M+H)⁺].

Step B: 1-[1-(2-Hydroxy-ethyl)-piperidin-4-yl]-3-[2-((R)-indan-1-ylamino)-quinolin-6-yl]-1-methyl-urea: Prepared from (R)—N-2-indan-1-yl-quinoline-2,6-diamine (Example 2) (200 mg, 0.726 mmol), 4-nitrophenyl chloroformate (146 mg, 0.726 mmol) and the above described 2-(4-methylamino-piperidin-1-yl)-ethanol (115 mg, 0.726 mmol) and diisopropylethyl amine (432 ul, 2.54 mmol) according to the procedure described for Example 170 step C. Obtained the title compound as an off-white solid (230 mg, 69%), MS (ISP) m/e=460.2 [(M+H)⁺].

Example 206 rac-1-[1-(2-Hydroxy-ethyl)-piperidin-4-yl]-3-[2-(7-methoxy-indan-1-ylamino)-quinolin-6-yl]-1-methyl-urea Prepared from rac-N-2-(7-methoxy-indan-1-yl)-quinoline-2,6-diamine (Example 172) (200 mg, 0.655 mmol), 4-nitrophenyl chloroformate (132 mg, 0.655 mmol) and the 2-(4-methylamino-piperidin-1-yl)-ethanol (Example 205 step A) (104 mg, 0.655 mmol) and diisopropylethyl amine (390 ul, 2.29 mmol) according to the procedure described for Example 170 step C. Obtained the title compound as an off-white solid (250 mg, 78%), MS (ISP) m/e=490.4 [(M+H)⁻].

Example 207 rac-1-[1-(2-Hydroxy-ethyl)-piperidin-4-yl]-3-[2-(4-methoxy-2,3-dihydro-benzofuran-3-ylamino)-quinolin-6-yl]-1-methyl-urea Prepared from rac-N-2-(4-methoxy-2,3-dihydro-benzofuran-3-yl)-quinoline-2,6-diamine (Example 173) (200 mg, 0.651 mmol), 4-nitrophenyl chloroformate (131 mg, 0.651 mmol) and the 2-(4-methylamino-piperidin-1-yl)-ethanol (Example 205 step A) (103 mg, 0.651 mmol) and diisopropylethyl amine (388 ul, 2.28 mmol) according to the procedure described for Example 170 step C. Obtained the title compound as an off-white solid (230 mg, 72%), MS (ISP) m/e=492.3 [(M+H)⁻].

Example 208 rac-3-[2-(5-Fluoro-indan-1-ylamino)-quinolin-6-yl]-1-[1-(2-hydroxy-ethyl)-piperidin-4-yl]-1-methyl-urea Prepared from rac-N-2-(5-fluoro-indan-1-yl)-quinoline-2,6-diamine (Example 106) (200 mg, 0.682 mmol), 4-nitrophenyl chloroformate (137 mg, 0.682 mmol) and the 2-(4-methylamino-piperidin-1-yl)-ethanol (Example 205 step A) (108 mg, 0.682 mmol) and diisopropylethyl amine (406 ul, 2.39 mmol) according to the procedure described for Example 170 step C. Obtained the title compound as an off-white solid (240 mg, 74%), MS (ISP) m/e=478.4 [(M+H)⁻].

Example 209 rac-3-[2-(6-Fluoro-2,3-dihydro-benzofuran-3-ylamino)-quinolin-6-yl]-1-[1-(2-hydroxy-ethyl)-piperidin-4-yl]-1-methyl-urea Prepared from rac-N-2-(6-fluoro-2,3-dihydro-benzofuran-3-yl)-quinoline-2,6-diamine (Example 200) (200 mg, 0.677 mmol), 4-nitrophenyl chloroformate (137 mg, 0.677 mmol) and the 2-(4-methylamino-piperidin-1-yl)-ethanol (Example 205 step A) (107 mg, 0.677 mmol) and diisopropylethyl amine (400 ul, 2.37 mmol) according to the procedure described for Example 170 step C. Obtained the title compound as an off-white foam (230 mg, 71%), MS (ISP) m/e=480.1 [(M+H)⁻].

Example 210

N-[2-((R)-Indan-1-ylamino)-quinolin-6-yl]-2-(4-methyl-piperazin-1-yl)-acetamide

The title compound was prepared in accordance with the general method 14 described in example 119 from (R)—N-2-indan-1-yl-quinoline-2,6-diamine (Example 2) (275 mg, 1.0 mmol) and (4-methylpiperazin-1-yl)-acetic acid (158 mg, 1.0 mmol). Obtained as a light red foam (339 mg, 82%), MS (ISP) m/e=416.4 (M+H⁺).

Example 211

N-[2-((R)-Indan-1-ylamino)-quinolin-6-yl]-2,2-dimethylpropionamide (R)—N-2-Indan-1-yl-quinoline-2,6-diamine (Example 2) (275 mg, 1.0 mmol) was dissolved in pyridine (3 ml), pivaloyl chloride (123 ul, 1 mmol) was added and the mixture was stirred at 23° C. for 18 h. All volatiles were removed in vacuum, the residue was directly subjected to chromatography with n-heptane/ethyl acetate to give the title compound as a light brown solid (182 mg, 51%), MS (ISP) m/e=360.2 (M+H⁺).

Example 212 rac-N-[2-(7-Methoxy-indan-1-ylamino)-quinolin-6-yl]-2-morpholin-4-yl-acetamide

The title compound was prepared in accordance with the general method 14 described in example 119 from rac-N-2-(7-methoxy-indan-1-yl)-quinoline-2,6-diamine and morpholin-4-yl-acetic acid; MS: m/e=431.5 (M−H⁻).

Example 213 rac-2-(2-Dimethylamino-ethylamino)-N-[2-(7-methoxy-indan-1-ylamino)-quinolin-6-yl]-acetamide Step A: rac-2-Chloro-N-[2-(7-methoxy-indan-1-ylamino)-quinolin-6-yl]-acetamide: rac-N-2-(7-methoxy-indan-1-yl)-quinoline-2,6-diamine (1.0 g, 3.3 mmol) was dissolved in 25 mL ethyl acetate and 25 mL saturated sodium bicarbonate solution. Chloroacetyl chloride (407 mg, 3.6 mmol) was added at 0° C. and the reaction mixture was stirred at room temperature for 1 h. The mixture was extracted three times with ethyl acetate and combined organic layers were dried over sodium sulfate. Removal of the solvent in vacuum left a yellow residue which was purified by silica gel column chromatography with heptane/ethyl acetate to give the title compound as a white solid (611 mg, 49%). MS (ISN) m/e=380.5 [(M−H)⁻].

Step B: rac-2-(2-Dimethylamino-ethylamino)-N-[2-(7-methoxy-indan-1-ylamino)-quinolin-6-yl]-acetamide: rac-2-Chloro-N-[2-(7-methoxy-indan-1-ylamino)-quinolin-6-yl]-acetamide (150 mg, 0.39 mmol) was suspended N,N-dimethylethylendiamine (693 mg, 7.9 mmol) and placed in an ultrasound bath for 4 min. The mixture was diluted with 5 mL saturated sodium bicarbonate solution and was extracted three times with ethyl acetate and combined organic layers were dried over sodium sulfate. Removal of the solvent in vacuum left a yellow residue which was purified by silica gel column chromatography with dichloromethane/methanol to give the title compound as a white foam (149 mg, 87%). MS (ISN) m/e=432.5 [(M−H)⁻].

Example 214 rac-2-(4-Cyclopropyl-piperazin-1-yl)-N-[2-(7-methoxy-indan-1-ylamino)-quinolin-6-yl]-acetamide The title compound was prepared in accordance with the general method 14 described in example 213 from rac-N-2-(7-methoxy-indan-1-yl)-quinoline-2,6-diamine and, chloroacetyl chloride and 1-cyclopropylpiperazine; MS: m/e=472.3 (M+H⁺).

The invention claimed is:
1. A compound of formula (I)

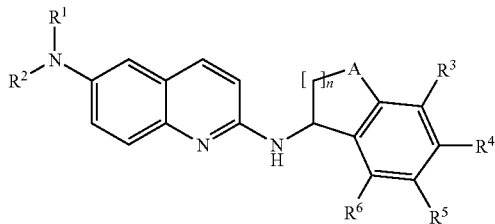

wherein
A is —CH$_2$— or —O—;
R$^1$ is hydrogen or alkyl;
R$^2$ is hydrogen,
  heterocycloalkyl,
  —(CH$_2$)$_a$—R$^a$, wherein R$^a$ is hydrogen, alkoxy, hydroxy, cyano, or NR$^i$R$^{ii}$, wherein R$^i$ and R$^{ii}$ are each independently hydrogen, alkyl or C(O)O-alkyl,
  allyl,
  —C(NH)—S—R$^b$, wherein R$^b$ is alkyl, cycloalkyl, haloalkyl, hydroxyalkyl, cyanoalkyl, or alkenyl,
  —C(NR$^c$)NR$^d$R$^e$, wherein R$^c$, R$^d$, and R$^e$ are each independently hydrogen, alkyl, cycloalkyl, heterocycloalkyl, or wherein R$^d$ and R$^e$ together with the nitrogen to which they are bound form a heterocycloalkyl,
  —C(O)R$^f$, wherein R$^f$ is alkyl, —(CH$_2$)$_b$-cycloalkyl, —(CH$_2$)$_b$—Oalkyl, —(CH$_2$)$_b$-heterocycloalkyl, —O-heterocycloalkyl, or —(CH$_2$)$_b$—NR$^{iii}$R$^{iv}$, wherein R$^{iii}$ and R$^{iv}$ are each independently hydrogen, alkyl, —C(O)Oalkyl, —(CH$_2$)$_b$-cycloalkyl, —(CH$_2$)$_a$—Oalkyl, bicyclic cycloalkyl, bicyclic cycloalkenyl, —(CH$_2$)$_b$-heterocycloalkyl, —(CH$_2$)$_a$-O-heterocycloalkyl, or —(CH$_2$)$_a$—NR'R", wherein R' and R" are each independently hydrogen, alkyl or cycloalkyl,
  —C(S)NR'R$^{vi}$, wherein R$^v$ and R$^{vi}$ are each independently H, alkyl or cycloalkyl,
  —S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or heterocycloalkyl, or
  —S(O)$_2$-heterocycloalkyl, or
R$^1$ and R$^2$ together with the N atom to which they are bound form a 5- or 6-membered heterocycloalkyl;
R$^3$, R$^4$, R$^5$ and R$^6$ are each independently selected from the group consisting of H, halo, alkyl, haloalkyl, hydroxyalkyl, cyanoalkyl, alkoxy, haloalkoxy, —O-alkylene-O-alkyl, hydroxyl, oxo, cyano, nitro and NR$^{ix}$R$^x$,
  wherein R$^{ix}$ and R$^x$ are each independently H or alkyl;
a is 1 to 6;
b is 0 to 6; and
n is 1 or 2, and wherein
heterocycloalkyl is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy; and wherein
cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, and alkyoxy;
or a pharmaceutically acceptable salt thereof.

2. The compound of claim 1, wherein a is 1 to 4.
3. The compound of claim 2, wherein a is 2.
4. The compound of claim 1, wherein b is 0 to 4.
5. The compound of claim 4, wherein b is 0 or 1.
6. The compound of claim 1, wherein R$^1$ is hydrogen or C$_{1-4}$alkyl.
7. The compound of claim 6, wherein R$^1$ is hydrogen.
8. The compound of claim 1, wherein R$^2$ is
hydrogen,
5- or 6-membered heterocycloalkyl,
—(CH$_2$)$_a$—R$^a$, wherein R$^a$ is hydrogen, alkoxy, hydroxy, cyano, or NR$^i$R$^{ii}$, wherein R$^i$ and R$^{ii}$ are each independently hydrogen, alkyl or C(O)O-alkyl,
allyl,
—C(NH)—S—R$^b$, wherein R$^b$ is alkyl, cycloalkyl, haloalkyl, hydroxyalkyl, cyanoalkyl, or alkenyl,
—C(NR$^c$)NR$^d$R$^e$, wherein R$^c$, R$^d$, and R$^e$ are each independently hydrogen, alkyl, cycloalkyl, 5- or 6-membered heterocycloalkyl, or wherein R$^d$ and R$^e$ together with the nitrogen to which they are bound form a 5- or 6-membered heterocycloalkyl,
—C(O)R$^f$, wherein R$^f$ is
alkyl,
—(CH$_2$)$_b$-cycloalkyl,
—(CH$_2$)$_b$—Oalkyl,
—(CH$_2$)$_b$-heterocycloalkyl, wherein the heterocycloalkyl is a 5- or 6-membered monocycle or a 7-, 8- or 9-membered bicycle,
—O-heterocycloalkyl, wherein the heterocycloalkyl is a 5- or 6-membered monocycle,
10- or 11-membered spirocyclic heterocycloalkyl, or
—(CH$_2$)$_b$—NR$^{iii}$R$^{iv}$, wherein R$^{iii}$ and R$^{iv}$ are each independently
hydrogen,
alkyl,
—C(O)Oalkyl,
—(CH$_2$)$_b$-cycloalkyl,
—(CH$_2$)$_a$—Oalkyl,
—(CH$_2$)$_a$—NR'R", wherein R' and R" are each independently hydrogen, alkyl or cycloalkyl,
7- or 8-membered bicyclic cycloalkyl or cycloalkenyl,
—(CH$_2$)$_b$-heterocycloalkyl, wherein the heterocycloalkyl is a 5- or 6-membered monocycle or a 7-, 8- or 9-membered bicycle, or
—(CH$_2$)$_a$—O-heterocycloalkyl, wherein the heterocycloalkyl is a 5- or 6-membered monocycle,
—C(S)NR'R$^{vi}$, wherein R$^v$ and R$^{vi}$ are each independently H, alkyl or cycloalkyl,
—S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or 5- or 6-membered heterocycloalkyl,
—S(O)$_2$-heterocycloalkyl, wherein the heterocycloalkyl is a 5- or 6-membered monocycle or a 7-, 8- or 9-membered bicycle, or
—S(O)$_2$-spirocyclic heteroalkyl, wherein the spirocyclic heteroalkyl is 10- or 11-membered;
a is 1 to 6,
b is 0 to 6, and wherein
heterocycloalkyl is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy; and wherein cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, and alkyoxy.

9. The compound of claim 1, wherein R$^2$ is
hydrogen,
6-membered heterocycloalkyl,
—(CH$_2$)$_a$—NR$^i$R$^{ii}$, wherein R$^i$ and R$^{ii}$ are each independently hydrogen, alkyl or C(O)O-alkyl,
allyl,
—C(=NH)—S-alkyl
—C(=NR$^c$)NR$^d$R$^e$, wherein R$^c$, R$^d$, and R$^e$ are each independently hydrogen, alkyl, cycloalkyl, 6-membered heterocycloalkyl, or wherein R$^d$ and R$^e$ together with the nitrogen to which they are bound form a 6-membered heterocycloalkyl,
—C(O)R$^f$, wherein R$^f$ is
alkyl,
—(CH$_2$)$_b$-cycloalkyl,
—(CH$_2$)$_b$—Oalkyl,
—(CH$_2$)$_b$-heterocycloalkyl, wherein the heterocycloalkyl is a 5- or 6-membered monocycle or a 7-membered bicycle, or
—O-heterocycloalkyl, wherein the heterocycloalkyl is a 6-membered monocycle, 10-membered spirocyclic heterocycloalkyl,
—(CH$_2$)$_b$—NR$^{iii}$R$^{iv}$, wherein R$^{iii}$ and R$^{iv}$ are each independently
hydrogen,
alkyl,
—C(O)Oalkyl,
—(CH$_2$)$_b$-cycloalkyl,
—(CH$_2$)$_a$—Oalkyl,
7-membered bicyclic cycloalkyl,
—(CH$_2$)$_b$-heterocycloalkyl, wherein the heterocycloalkyl is a 5- or 6-membered monocycle or a 8- or 9-membered bicycle,
—(CH$_2$)$_a$—O-heterocycloalkyl, wherein the heterocycloalkyl is a 6-membered monocycle, or
—(CH$_2$)$_a$—NR'R'', wherein R' and R'' are each independently alkyl or cycloalkyl,
—C(S)NH$_2$,
—S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or 6-membered heterocycloalkyl,
—S(O)$_2$-heterocycloalkyl, wherein the heterocycloalkyl is a 5- or 6-membered monocycle or a 7-membered bicycle, or
—S(O)$_2$-spirocyclic heteroalkyl, wherein the spirocyclic heteroalkyl is 10- or 11-membered,
a is 1 to 6,
b is 0 to 6, and wherein
heterocycloalkyl is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy; and wherein cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, and alkyoxy.

10. The compound of claim 1, wherein R$^2$ is
hydrogen,
morpholin-4-yl, 4-methyl-piperazin-1-yl, or piperazin-1-yl,
—(CH$_2$)$_a$—NR$^i$R$^{ii}$, wherein R$^i$ and R$^{ii}$ are each independently hydrogen, alkyl or C(O)O-alkyl, allyl,
—C(=NH)—S-alkyl,
—C(=NR$^c$)NR$^d$R$^e$, wherein R$^c$ is H or alkyl, and R$^d$ and R$^e$ are each independently hydrogen, alkyl, cycloalkyl, 1-methyl-piperidin-4-yl, piperidin-4-yl, or wherein R$^d$ and R$^e$ together with the nitrogen to which they are bound form a morpholine ring, a piperazine ring, or a 4-methyl-piperazine ring,
—C(O)R$^f$, wherein R$^f$ is
alkyl,
—(CH$_2$)$_b$-cycloalkyl,
—(CH$_2$)$_b$—Oalkyl,
—(CH$_2$)$_b$-heterocycloalkyl, wherein the heterocycloalkyl is selected from the group consisting of morpholin-4-yl, tetrahydropyran-4-yl, 4-methyl-piperazin-1-yl, 4-isopropyl-piperazin-1-yl, piperazin-1-yl, thiomorpholin-4-yl, 4-hydroxy-4-methyl-piperidine-1-yl, (1S,4S)-2-oxa-5-aza-bicyclo[2.2.1]heptan-5-yl, (1R,5S)-8-oxa-3-aza-bicyclo[3.2.1]octan-3-yl, 4-hydroxymethyl-piperidine-1-yl, 4-tert-butyl-piperazine-1-yl, 4-methyl-piperidine-1-yl, and piperidine-1-yl,
—O-heterocycloalkyl, wherein the heterocycloalkyl is 4-methyl-piperidine-1-yl, or piperidine-1-yl,
2-oxa-8-aza-spiro[4.5]decan-8-yl,
—(CH$_2$)$_b$—NR$^{iii}$R$^{iv}$, wherein R$^{iii}$ and R$^{iv}$ are each independently
hydrogen,
alkyl,
—C(O)Oalkyl,
—(CH$_2$)$_b$-cycloalkyl, wherein cycloalkyl is selected from cyclohexyl, 4-hydroxycyclohexyl, cyclopropyl, 2-phenyl-cycloprop-1-yl, or cyclopentyl,
—(CH$_2$)$_a$—Oalkyl,
—(CH$_2$)$_a$—NR'R'', wherein R' and R'' are each independently alkyl or cycloalkyl, bicyclo[2.2.1]heptanyl, or
—(CH$_2$)$_b$-heterocycloalkyl, wherein the heterocycloalkyl is 4-methyl-piperazin-1-yl, tetrahydro-pyran-4-yl, 1-methyl-piperidin-4-yl, 1-benzyl-pyrrolidin-3-yl, 1,1-dioxo-tetrahydro-thiophen-3-yl, morpholin-4-yl, piperidin-4-yl, 1-tert-butoxycarbonyl-piperidin-4-yl, 1-cyclopropyl-piperidin-4-yl, 1-isopropyl-piperidin-4-yl, 1-(2-methoxyethyl)-piperidin-4-yl, 1-(2-fluoroethyl)-piperidin-4-yl, 1-(3,3,3-trifluoropropyl)-piperidin-4-yl, 1-(2-methylsulfanyl-ethyl)-piperidin-4-yl, 3-(endo)-9-methyl-9-aza-bicyclo[3.3.1]non-3-yl, 1-(3,3,3-trifluoro-propionyl)-piperidin-4-yl, 1,1-dioxo-hexahydro-thiopyran-4-yl, 3-endo-(8-methyl-8-aza-bicyclo[3.2.1]oct-3-yl, 1-(2-fluoroacetyl)-piperidin-4-yl, 1-methyl-pyrrolidin-3-yl, 1-methoxycarbonyl-piperidin-4-yl, (3-exo)-8-cyclopropyl-8-aza-bicyclo[3.2.1]oct-3-yl, (3-exo)-9-(2,2,2-trifluoro-ethyl)-9-aza-bicyclo[3.3.1]non-3-yl, (3-exo)-8-methyl-8-aza-bicyclo[3.2.1]oct-3-yl, (7-exo)-9-methyl-3-oxa-9-aza-bicyclo[3.3.1]non-7-yl, 1-methyl-pyrrolidin-3-yl, (3-exo)-9-cyclopropyl-9-aza-bicyclo[3.3.1]non-3-yl, (7-exo)-9-methyl-3-thia-9-aza-bicyclo[3.3.1]non-7-yl, 1-cyanomethyl-piperidin-4-yl, 1-(2-methanesulfonyl-ethyl)-piperidin-4-yl, (N,N-dimethylamino-carbonylmethylene)-piperidin-4-yl, 1-(2-hydroxy-ethyl)-piperidin-4-yl, (3-exo)-9-isopropyl-9-aza-bicyclo[3.3.1]non-3-yl, (3-exo)-8-cyclopropyl-8-aza-bicyclo[3.2.1]oct-3-yl, (3-exo)-8-isopropyl-8-aza-bicyclo[3.2.1]oct-3-yl, (1R,5S)-8-methyl-8-aza-bicyclo[3.2.1]oct-3-yl, (1R,5S)-9-isopropyl-3-oxa-9-aza-bicyclo[3.3.1]non-3-yl, or 1-(2-hydroxy-2-methyl-propyl)-piperidin-4-yl,

—C(S)NH$_2$,

—S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or tetrahydro-2H-pyran-4-yl, —S(O)$_2$-heterocycloalkyl, wherein the heterocycloalkyl is selected from the group consisting of pyrrolidin-1-yl, 3,3-difluoro-pyrrolidin-1-yl, morpholin-4-yl, 4-methyl-piperazin-1-yl, piperazin-1-yl, thiomorpholin-4-yl, 1,1-dioxo-thiomorpholin-4-yl, 4-methoxymethyl-piperidin-1-yl, 4-methoxy-piperidine-1-yl, (1S,4S)-2-oxa-5-azabicyclo[2.2.1]hept-5-yl, (1R,5S)-8-oxa-3-azabicyclo[3.2.1]oct-3-yl, or —S(O)$_2$-spirocyclic heteroalkyl, wherein the spirocyclic heteroalkyl is 2-oxa-8-aza-spiro[4.5]decan-8-yl, or 1,4-dioxa-8-aza-spiro[4.5]decanyl, a is 1 to 6, and b is 0 to 6.

11. The compound of claim 1, wherein R$^2$ is

—C(O)R$^f$, wherein R$^f$ is —(CH$_2$)$_b$-cycloalkyl, —(CH$_2$)$_b$-heterocycloalkyl, or —(CH$_2$)$_b$—NR$^{iii}$R$^{iv}$, wherein R$^{iii}$ and R$^{iv}$ are each independently hydrogen, alkyl, —C(O)Oalkyl, —(CH$_2$)$_b$-cycloalkyl, —(CH$_2$)$_a$—Oalkyl, bicyclic cycloalkyl, bicyclic cycloalkenyl, —(CH$_2$)$_b$-heterocycloalkyl, or —(CH$_2$)$_a$—NR'R", wherein R' and R" are each independently hydrogen, alkyl or cycloalkyl, —S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or heterocycloalkyl, or —S(O)$_2$-heterocycloalkyl, a is 1 to 6, preferably 1 to 4, more preferably 2, b is 0 to 6, preferably 0 to 4, more preferably 0 or 1, heterocycloalkyl is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy; and cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, and alkyoxy.

12. The compound of claim 1, wherein A is —CH$_2$— and n is 1 or 2 or wherein A is —O— and n is 1.

13. The compound of claim 12, wherein A is —CH$_2$— and n is 1.

14. The compound of claim 12, wherein A is —CH$_2$— and n is 2.

15. The compound of claim 12, wherein A is —O— and n is 1.

16. The compound of claim 1, wherein

R$^3$, R$^4$, R$^5$ and R$^6$ are each independently selected from the group consisting of H, halo, alkoxy, alkyl, haloalkoxy, or —O-alkylene-O-alkyl.

17. The compound of claim 16, wherein R$^3$ is H, halo, or alkyl.

18. The compound of claim 17, wherein R$^3$ is H, chloro, or methyl.

19. The compound of claim 16, wherein R$^4$ is H, halo, or alkyl.

20. The compound of claim 19, wherein R$^4$ is H, fluor, or methyl.

21. The compound of claim 16, wherein R$^5$ is H or halo.

22. The compound of claim 21, wherein R$^5$ is H, fluoro, or chloro.

23. The compound of claim 16, wherein R$^6$ is H, alkoxy, alkyl, halo, or —O-alkylene-O-alkyl.

24. The compound of claim 23, wherein R$^6$ is H, halo, C$_{1-4}$alkoxy, C$_{1-4}$alkyl, fluoro, or —O—CH$_2$CH$_2$OMe.

25. The compound of claim 16, wherein R$^3$, R$^4$, R$^5$, and R$^6$ all are H.

26. The compound of claim 16, wherein R$^3$, R$^4$, and R$^5$ are H and R$^6$ is alkoxy, alkyl, halo, or —O-alkylene-O-alkyl.

27. The compound of claim 16, wherein R$^3$, R$^5$, and R$^6$ are H and R$^4$ is halo.

28. The compound of claim 16, wherein R$^3$, R$^4$, and R$^6$ are H and R$^5$ is halo.

29. The compound of claim 16, wherein R$^3$ and R$^5$ are chloro, R$^4$ is H, and R$^6$ is methoxy.

30. The compound of claim 16, wherein R$^3$ is alkyl, R$^4$ and R$^5$ are H, and R$^6$ is alkoxy.

31. The compound of claim 16, wherein R$^3$ and R$^5$ are H, R$^4$ is alkyl, and R$^6$ is alkoxy.

32. The compound of claim 1 wherein not all of R$^1$, R$^2$, R$^3$, R$^4$, R$^5$, and R$^6$ are simultaneously H.

33. The compound of claim 1, selected from the group consisting of

N$^6$-(3-Dimethylamino-propyl)-N$^2$—(R)-indan-1-yl-quinoline-2,6-diamine;

(R)—N$^2$-Indan-1-yl-quinoline-2,6-diamine;

1-[2-((R)-Indan-1-ylamino)-quinolin-6-yl]-3-isopropyl-urea;

N$^6$-Allyl-N$^2$—(R)-indan-1-yl-quinoline-2,6-diamine;

1-Cyclohexyl-3-[2-((R)-indan-1-ylamino)-quinolin-6-yl]-urea;

1-[2-((R)-Indan-1-ylamino)-quinolin-6-yl]-3-((1S,2R)-2-phenyl-cyclopropyl)-urea;

1-[2-((R)-Indan-1-ylamino)-quinolin-6-yl]-3-methyl-urea;

1-tert-Butyl-3-[2-((R)-indan-1-ylamino)-quinolin-6-yl]-urea;

[2-((R)-Indan-1-ylamino)-quinolin-6-yl]-urea; and rac-1-[2-(2,3-Dihydro-benzofuran-3-ylamino)-quinolin-6-yl]-3-isopropyl-urea.

34. The compound of claim 1, selected from the group consisting of (+)-1-{2-[-(2,3-Dihydro-benzofuran-3-yl)amino]-quinolin-6-yl}-3-isopropyl-urea;

rac-1-Isopropyl-3-[2-(7-methoxy-indan-1-ylamino)-quinolin-6-yl]-urea;

(−)-1-Isopropyl-3-[2-(7-methoxy-indan-1-ylamino)-quinolin-6-yl]-urea;

rac-N$^2$-(8-Methoxy-1,2,3,4-tetrahydro-naphthalen-1-yl)-quinoline-2,6-diamine;

rac-1-Isopropyl-3-[2-(8-methoxy-1,2,3,4-tetrahydro-naphthalen-1-ylamino)-quinolin-6-yl]-urea;

4-Methyl-piperazine-1-carboxylic acid [2-((R)-indan-1-ylamino)-quinolin-6-yl]-amide;

1-[2-((R)-Indan-1-ylamino)-quinolin-6-yl]-3-(2-methoxy-ethyl)-urea;

1-(2-Dimethylamino-ethyl)-3-[2-((R)-indan-1-ylamino)-quinolin-6-yl]-urea;
1-[2-((R)-Indan-1-ylamino)-quinolin-6-yl]-3-(tetrahydro-pyran-4-yl)-urea; and
1-[2-((R)-Indan-1-ylamino)-quinolin-6-yl]-3-(1-methyl-piperidin-4-yl)-urea.

35. The compound of claim 1, selected from the group consisting of
1-Cyclopropyl-3-[2-((R)-indan-1-ylamino)-quinolin-6-yl]-urea;
Morpholine-4-carboxylic acid [2-((R)-indan-1-ylamino)-quinolin-6-yl]-amide;
1-Cyclopropylmethyl-3-[2-((R)-indan-1-ylamino)-quinolin-6-yl]-urea;
Thiomorpholine-4-carboxylic acid [2-((R)-indan-1-ylamino)-quinolin-6-yl]-amide;
1-(1-Benzyl-pyrrolidin-3-yl)-3-[2-((R)-indan-1-ylamino)-quinolin-6-yl]-urea;
1-Bicyclo[2.2.1]hept-2-yl-3-[2-((R)-indan-1-ylamino)-quinolin-6-yl]-urea;
1-(1,1-Dioxo-tetrahydro-thiophen-3-yl)-3-[2-((R)-indan-1-ylamino)-quinolin-6-yl]-urea;
1-Ethyl-1-(4-hydroxy-cyclohexyl)-3-[2-((R)-indan-1-ylamino)-quinolin-6-yl]-urea;
1-[2-((R)-Indan-1-ylamino)-quinolin-6-yl]-3-(2-morpholin-4-yl-ethyl)-urea; and
4-Hydroxy-4-methyl-piperidine-1-carboxylic acid [2-((R)-indan-1-ylamino)-quinolin-6-yl]-amide.

36. The compound of claim 1, selected from the group consisting of
2-Oxa-8-aza-spiro[4.5]decane-8-carboxylic acid [2-((R)-indan-1-ylamino)-quinolin-6-yl]-amide;
1-[2-(Cyclopropyl-methyl-amino)-ethyl]-3-[2-((R)-indan-1-ylamino)-quinolin-6-yl]-urea;
(1S,4S)-2-Oxa-5-aza-bicyclo[2.2.1]heptane-5-carboxylic acid [2-((R)-indan-1-ylamino)-quinolin-6-yl]-amide;
(1R,5 S)-8-Oxa-3-aza-bicyclo[3.2.1]octane-3-carboxylic acid [2-((R)-indan-1-ylamino)-quinolin-6-yl]-amide;
rac-1-[2-(2,3-Dihydro-benzofuran-3-ylamino)-quinolin-6-yl]-3-(1-methyl-piperidin-4-yl)-urea;
1-[2-((R)-Indan-1-ylamino)-quinolin-6-yl]-3-[2-(tetrahydro-pyran-2-yloxy)-ethyl]-urea;
4-Hydroxymethyl-piperidine-1-carboxylic acid [2-((R)-indan-1-ylamino)-quinolin-6-yl]-amide;
4-{3-[2-((R)-Indan-1-ylamino)-quinolin-6-yl]-ureido}-piperidine-1-carboxylic acid tert-butyl ester;
1-[2-((R)-Indan-1-ylamino)-quinolin-6-yl]-3-piperidin-4-yl-urea; and
rac-1-[2-(7-Methoxy-indan-1-ylamino)-quinolin-6-yl]-3-(1-methyl-piperidin-4-yl)-urea.

37. The compound of claim 1, selected from the group consisting of
1-(1-Cyclopropyl-piperidin-4-yl)-3-[2-((R)-indan-1-ylamino)-quinolin-6-yl]-urea;
1-[2-((R)-Indan-1-ylamino)-quinolin-6-yl]-3-(1-isopropyl-piperidin-4-yl)-urea;
1-[2-((R)-Indan-1-ylamino)-quinolin-6-yl]-3-[1-(2-methoxy-ethyl)-piperidin-4-yl]-urea;
rac-1-(1-Isopropyl-piperidin-4-yl)-3-[2-(7-methoxy-indan-1-ylamino)-quinolin-6-yl]-urea;
rac-1-[1-(2-Methoxy-ethyl)-piperidin-4-yl]-3-[2-(7-methoxy-indan-1-ylamino)-quinolin-6-yl]-urea;
rac-1-[1-(2-Fluoro-ethyl)-piperidin-4-yl]-3-[2-(7-methoxy-indan-1-ylamino)-quinolin-6-yl]-urea;
rac-1-[2-(7-Methoxy-indan-1-ylamino)-quinolin-6-yl]-3-[1-(3,3,3-trifluoro-propyl)-piperidin-4-yl]-urea;
1-[2-((R)-Indan-1-ylamino)-quinolin-6-yl]-3-[1-(2-methylsulfanyl-ethyl)-piperidin-4-yl]-urea;
1-[2-((R)-Indan-1-ylamino)-quinolin-6-yl]-3-((endo)-9-methyl-9-aza-bicyclo[3.3.1]non-3-yl)-urea; and
rac-1-[2-(7-Methoxy-indan-1-ylamino)-quinolin-6-yl]-(9-methyl-9-aza-bicyclo[3.3.1]non-3-yl)-urea.

38. The compound of claim 1, selected from the group consisting of
rac-1-[2-(7-Methoxy-indan-1-ylamino)-quinolin-6-yl]-3-[1-(2-methylsulfanyl-ethyl)-piperidin-4-yl]-urea;
rac-1-[2-(7-Methoxy-indan-1-ylamino)-quinolin-6-yl]-3-[1-(3,3,3-trifluoro-propionyl)-piperidin-4-yl]-urea;
rac-1-(1-Cyclopropyl-piperidin-4-yl)-3-[2-(7-methoxy-indan-1-ylamino)-quinolin-6-yl]-urea;
rac-1-(1,1-Dioxo-hexahydro-thiopyran-4-yl)-3-[2-(8-methoxy-1,2,3,4-tetrahydro-naphthalen-1-ylamino)-quinolin-6-yl]-urea;
rac-1-(1-Cyclopropyl-piperidin-4-yl)-3-[2-(8-methoxy-1,2,3,4-tetrahydro-naphthalen-1-ylamino)-quinolin-6-yl]-urea;
rac-1-[2-(8-Methoxy-1,2,3,4-tetrahydro-naphthalen-1-ylamino)-quinolin-6-yl]-3-endo-(9-methyl-9-aza-bicyclo[3.3.1]non-3-yl)-urea;
rac-1-[2-(8-Methoxy-1,2,3,4-tetrahydro-naphthalen-1-ylamino)-quinolin-6-yl]-3-(1-methyl-piperidin-4-yl)-urea;
rac-1-[1-(2-Methoxy-ethyl)-piperidin-4-yl]-3-[2-(8-methoxy-1,2,3,4-tetrahydro-naphthalen-1-ylamino)-quinolin-6-yl]-urea;
rac-1-[1-(2-Fluoro-ethyl)-piperidin-4-yl]-3-[2-(8-methoxy-1,2,3,4-tetrahydro-naphthalen-1-ylamino)-quinolin-6-yl]-urea; and
rac-endo-1-[2-(8-Methoxy-1,2,3,4-tetrahydro-naphthalen-1-ylamino)-quinolin-6-yl]-3-(8-methyl-8-aza-bicyclo[3.2.1]oct-3-yl)-urea.

39. The compound of claim 1, selected from the group consisting of
1-[1-(2-Fluoro-acetyl)-piperidin-4-yl]-3-[2-((R)-indan-1-ylamino)-quinolin-6-yl]-urea;
1-[2-((R)-Indan-1-ylamino)-quinolin-6-yl]-3-[1-(3,3,3-trifluoro-propionyl)-piperidin-4-yl]-urea;
1-[2-((R)-Indan-1-ylamino)-quinolin-6-yl]-3-[1-(3,3,3-trifluoro-propyl)-piperidin-4-yl]-urea;
1-[2-(8-Methoxy-1,2,3,4-tetrahydro-naphthalen-1-ylamino)-quinolin-6-yl]-3-((S)-1-methyl-pyrrolidin-3-yl)-urea;
rac-1-[2-(4,6-Dichloro-7-methoxy-indan-1-ylamino)-quinolin-6-yl]-3-isopropyl-urea;
N'-{2-[(1R)-2,3-dihydro-1H-inden-1-ylamino]quinolin-6-yl}-N,N-dimethylsulfamide;
rac-N'-[2-(2,3-dihydro-1-benzofuran-3-ylamino)quinolin-6-yl]-N,N-dimethylsulfamide;
rac-N'-{2-[(7-methoxy-2,3-dihydro-1H-inden-1-yl)amino]quinolin-6-yl}-N,N-dimethylsulfamide;
rac-N'-{2-[(8-Methoxy-1,2,3,4-tetrahydronaphthalen-1-yl)amino]quinolin-6-yl}-N,N-dimethylsulfamide; and
rac-N'-{2-[(4,6-Dichloro-7-methoxy-2,3-dihydro-1H-inden-1-yl)amino]quinolin-6-yl}-N,N-dimethylsulfamide.

40. The compound of claim 1, selected from the group consisting of
tert-butyl[({2-[(1R)-2,3-dihydro-1H-inden-1-ylamino]quinolin-6-yl}amino)sulfonyl]carbamate;
N-{2-[(1R)-2,3-dihydro-1H-inden-1-ylamino]quinolin-6-yl}sulfamide hydrochloride;
Pyrrolidine-1-sulfonic acid [2-((R)-indan-1-ylamino)-quinolin-6-yl]-amide;

3,3-Difluoro-pyrrolidine-1-sulfonic acid [2-((R)-indan-1-ylamino)-quinolin-6-yl]-amide;
(2-Methoxy-ethyl)-methyl-sulfonic acid [2-((R)-indan-1-ylamino)quinolin-6-yl]-amide;
Morpholine-4-sulfonic acid [2-((R)-indan-1-ylamino)-quinolin-6-yl]-amide;
4-Methyl-piperazine-1-sulfonic acid [2-((R)-indan-1-ylamino)-quinolin-6-yl]-amide;
Thiomorpholine-4-sulfonic acid [2-((R)-indan-1-ylamino)-quinolin-6-yl]-amide;
1,1-Dioxo-thiomorpholine-4-sulfonic acid [2-((R)-indan-1-ylamino)-quinolin-6-yl]-amide; and
N-{2-[(1R)-2,3-dihydro-1H-inden-1-ylamino]quinolin-6-yl}-N'-(tetrahydro-2H-pyran-4-yl)sulfamide.

41. The compound of claim 1, selected from the group consisting of
N'-{2-[(1R)-2,3-dihydro-1H-inden-1-ylamino]quinolin-6-yl}-N-methyl-N-(tetrahydro-2H-pyran-4-yl)sulfamide;
1,4-Dioxa-8-aza-spiro[4.5]decane-8-sulfonic acid [2-((R)-indan-1-ylamino)-quinolin-6-yl]-amide;
4-Methoxymethyl-piperidine-1-sulfonic acid [2-((R)-indan-1-ylamino)-quinolin-6-yl]-amide;
4-Methoxy-piperidine-1-sulfonic acid [2-((R)-indan-1-ylamino)-quinolin-6-yl]-amide;
N-cyclopropyl-N'-{2-[(1R)-2,3-dihydro-1H-inden-1-ylamino]quinolin-6-yl}-N-methylsulfamide;
N-(cyclopropylmethyl)-N'-{2-[(1R)-2,3-dihydro-1H-inden-1-ylamino]quinolin-6-yl}-N-methylsulfamide;
2-Oxa-8-aza-spiro[4.5]decane-8-sulfonic acid [2-((R)-indan-1-ylamino)-quinolin-6-yl]-amide;
(1S,4S)-2-Oxa-5-aza-bicyclo[2.2.1]heptane-5-sulfonic acid [2-((R)-indan-1-ylamino)-quinolin-6-yl]-amide;
(1S,5R)-8-Oxa-3-aza-bicyclo[3.2.1]octane-3-sulfonic acid [2-((R)-indan-1-ylamino)-quinolin-yl]-amide; and
(1S,4S)-2-Oxa-5-aza-bicyclo[2.2.1]heptane-5-sulfonic acid [2-(2,3-dihydro-benzofuran-3-ylamino)-quinolin-6-yl]-amide.

42. The compound of claim 1, selected from the group consisting of
(1S,4S)-2-Oxa-5-aza-bicyclo[2.2.1]heptane-5-sulfonic acid [2-(8-methoxy-1,2,3,4-tetrahydro-naphthalen-1-ylamino)-quinolin-6-yl]-amide;
N-Cyclopropyl-N'-{2-[(1R)-2,3-dihydro-1H-inden-1-ylamino]quinolin-6-yl}sulfamide;
rac-1-Isopropyl-3-[2-(7-methoxy-4-methyl-indan-1-ylamino)-quinolin-6-yl]-urea;
rac-N'-{2-[(7-Methoxy-4-methyl-2,3-dihydro-1H-inden-1-yl)amino]quinolin-6-yl}-N,N-dimethylsulfamide;
rac-1-[2-(7-Methoxy-4-methyl-indan-1-ylamino)-quinolin-6-yl]-3-(1-methyl-piperidin-4-yl)-urea;
4-{3-[2-((R)-Indan-1-ylamino)-quinolin-6-yl]-ureido}-piperidine-1-carboxylic acid methyl ester;
1-[1-(2-Fluoro-ethyl)-piperidin-4-yl]-3-[2-((R)-indan-1-ylamino)-quinolin-6-yl]-urea;
rac-1-[2-(4,6-dichloro-7-methoxy-indan-1-ylamino)-quinolin-6-yl]-3-(1-methyl-piperidin-4-yl)-urea;
1-((3-exo)-8-Cyclopropyl-8-aza-bicyclo[3.2.1]oct-3-yl)-3-[2-((R)-indan-1-ylamino)-quinolin-6-yl]-urea; and
1-[2-((R)-Indan-1-ylamino)-quinolin-6-yl]-3-[(3-exo)-9-(2,2,2-trifluoro-ethyl)-9-aza-bicyclo[3.3.1]non-3-yl]-urea.

43. The compound of claim 1, selected from the group consisting of
1-[2-((R)-Indan-1-ylamino)-quinolin-6-yl]-3-((3-exo)-8-methyl-8-aza-bicyclo[3.2.1]oct-3-yl)-urea;
rac-N²-(7-Methyl-indan-1-yl)-quinoline-2,6-diamine;
rac-1-Isopropyl-3-[2-(7-methyl-indan-1-ylamino)-quinolin-6-yl]-urea;
1-[2-((R)-Indan-1-ylamino)-quinolin-6-yl]-3-((7-exo)-9-methyl-3-oxa-9-aza-bicyclo[3.3.1]non-7-yl)-urea;
1-[2-(8-Methoxy-1,2,3,4-tetrahydro-naphthalen-1-ylamino)-quinolin-6-yl]-3-((R)-1-methyl-pyrrolidin-3-yl)-urea;
rac-N²-(5-Fluoro-indan-1-yl)-quinoline-2,6-diamine;
rac-1-[2-(5-Fluoro-indan-1-ylamino)-quinolin-6-yl]-3-isopropyl-urea;
{2-[2-((R)-Indan-1-ylamino)-quinolin-6-ylamino]-ethyl}-methyl-carbamic acid tert-butyl ester;
N²—(R)-Indan-1-yl-N-6-(2-methylamino-ethyl)-quinoline-2,6-diamine; and
1-((3-exo)-9-Cyclopropyl-9-aza-bicyclo[3.3.1]non-3-yl)-3-[2-((R)-indan-1-ylamino)-quinolin-6-yl]-urea.

44. The compound of claim 1, selected from the group consisting of
1-[2-((R)-Indan-1-ylamino)-quinolin-6-yl]-3-((7-exo)-9-methyl-3-thia-9-aza-bicyclo[3.3.1]non-7-yl)-urea;
4-Isopropyl-piperazine-1-carboxylic acid [2-((R)-indan-1-ylamino)-quinolin-6-yl]-amide;
4-tert-Butyl-piperazine-1-carboxylic acid [2-((R)-indan-1-ylamino)-quinolin-6-yl]-amide;
1-[2-((R)-Indan-1-ylamino)-quinolin-6-yl]-3-methyl-imidazolidin-2-one;
rac-1-[2-(5-Fluoro-indan-1-ylamino)-quinolin-6-yl]-3-(1-isopropyl-piperidin-4-yl)-urea;
N-[2-((R)-Indan-1-ylamino)-quinolin-6-yl]-isobutyramide;
2-Cyclopentyl-N-[2-((R)-indan-1-ylamino)-quinolin-6-yl]-acetamide;
rac-N-[2-(8-Methoxy-1,2,3,4-tetrahydro-naphthalen-1-ylamino)-quinolin-6-yl]-isobutyramide;
rac-2-Dimethylamino-N-[2-(8-methoxy-1,2,3,4-tetrahydro-naphthalen-1-ylamino)-quinolin-6-yl]-acetamide; and
rac-2-Methoxy-N-[2-(8-methoxy-1,2,3,4-tetrahydro-naphthalen-1-ylamino)-quinolin-6-yl]-acetamide.

45. The compound of claim 1, selected from the group consisting of
rac-N-[2-(8-Methoxy-1,2,3,4-tetrahydro-naphthalen-1-ylamino)-quinolin-6-yl]-2-morpholin-4-yl-acetamide;
{[2-((R)-Indan-1-ylamino)-quinolin-6-ylcarbamoyl]-methyl}-arbamic acid tert-butyl ester;
2-Amino-N-[2-((R)-indan-1-ylamino)-quinolin-6-yl]-acetamide;
1-Methyl-piperidine-4-carboxylic acid [2-((R)-indan-1-ylamino)-quinolin-6-yl]-amide;
rac-N-[2-(8-Methoxy-1,2,3,4-tetrahydro-naphthalen-1-ylamino)-quinolin-6-yl]-2-(tetrahydro-pyran-4-yl)-acetamide;
rac-2-Dimethylamino-N-[2-(7-methoxy-indan-1-ylamino)-quinolin-6-yl]-acetamide;
rac-N-[2-(6-Fluoro-indan-1-ylamino)-quinolin-6-yl]-2-(4-methyl-piperazin-1-yl)-acetamide;
rac-(N)-[2-(7-Methoxy-indan-1-ylamino)-quinolin-6-yl]-isobutyramide;
rac-1-Methyl-piperidine-4-carboxylic acid [2-(7-methoxy-indan-1-ylamino)-quinolin-6-yl]-amide; and
rac-1-Isopropyl-3-[2-(7-methoxy-5-methyl-indan-1-ylamino)-quinolin-6-yl]-urea.

46. The compound of claim 1, selected from the group consisting of
rac-1-[2-(7-Methoxy-5-methyl-indan-1-ylamino)-quinolin-6-yl]-3-(1-methyl-piperidin-4-yl)-urea;

rac-N'-{2-[(7-Methoxy-5-methyl-2,3-dihydro-1H-inden-1-yl)amino]quinolin-6-yl}-N,N-dimethylsulfamide;
1-(1-Cyanomethyl-piperidin-4-yl)-3-[2-((R)-indan-1-ylamino)-quinolin-6-yl]-urea;
1-[2-((R)-Indan-1-ylamino)-quinolin-6-yl]-3-[1-(2,2,2-trifluoro-ethyl)-piperidin-4-yl]-urea;
1-[2-((R)-Indan-1-ylamino)-quinolin-6-yl]-3-[1-(2-methanesulfonyl-ethyl)-piperidin-4-yl]-urea;
2-(4-{3-[2-((R)-Indan-1-ylamino)-quinolin-6-yl]-ureido}-piperidin-1-yl)-N,N-dimethylacetamide;
1-[1-(2-Hydroxy-ethyl)-piperidin-4-yl]-3-[2-((R)-indan-1-ylamino)-quinolin-6-yl]-urea;
[2-((R)-Indan-1-ylamino)-quinolin-6-yl]-carbamic acid isopropyl ester;
rac-N-[2-(7-Methoxy-indan-1-ylamino)-quinolin-6-yl]-2-(4-methyl-piperazin-1-yl)-acetamide; and
rac-Cyclopropanecarboxylic acid [2-(7-methoxy-indan-1-ylamino)-quinolin-6-yl]-amide.

47. The compound of claim 1, selected from the group consisting of
rac-Cyclopropanecarboxylic acid [2-(5-fluoro-indan-1-ylamino)-quinolin-6-yl]-amide;
rac-N-[2-(5-Fluoro-indan-1-ylamino)-quinolin-6-yl]-2-(4-methyl-piperazin-1-yl)-acetamide;
rac-$N^2$-(6-Fluoro-indan-1-yl)-quinoline-2,6-diamine;
rac-1-[2-(6-Fluoro-indan-1-ylamino)-quinolin-6-yl]-3-isopropyl-urea;
rac-$N^2$-(7-Fluoro-indan-1-yl)-quinoline-2,6-diamine;
rac-1-[2-(7-Fluoro-indan-1-ylamino)-quinolin-6-yl]-3-isopropyl-urea;
rac-N-[2-(5-Fluoro-indan-1-ylamino)-quinolin-6-yl]-2-(4-isopropyl-piperazin-1-yl)-acetamide;
(1S,4S)-2-Oxa-5-aza-bicyclo[2.2.1]heptane-5-sulfonic acid [2-(7-methoxy-indan-1-ylamino)-quinolin-6-yl]-amide;
[2-((R)-Indan-1-ylamino)-quinolin-6-yl]-thiourea; and
1-[2-((R)-Indan-1-ylamino)-quinolin-6-yl]-2-methyl-isothiourea hydroiodide.

48. The compound of claim 1, selected from the group consisting of
N-[2-((R)-Indan-1-ylamino)-quinolin-6-yl]-morpholine-4-carboxamidine;
N-[2-((R)-Indan-1-ylamino)-quinolin-6-yl]-N'-(1-methyl-piperidin-4-yl)-guanidine;
N-[2-((R)-Indan-1-ylamino)-quinolin-6-yl]-N-isopropyl-guanidine;
N-Cyclopropyl-N'-[2-((R)-indan-1-ylamino)-quinolin-6-yl]-guanidine;
rac-1-[2-(6-Fluoro-indan-1-ylamino)-quinolin-6-yl]-3-(1-isopropyl-piperidin-4-yl)-urea;
rac-1-[2-(7-Fluoro-indan-1-ylamino)-quinolin-6-yl]-3-(1-isopropyl-piperidin-4-yl)-urea;
rac-[2-(7-Fluoro-indan-1-ylamino)-quinolin-6-yl]-carbamic acid methyl ester;
rac-N-[2-(5-Fluoro-indan-1-ylamino)-quinolin-6-yl]-2-morpholin-4-yl-acetamide;
rac-N-[2-(5-Fluoro-indan-1-ylamino)-quinolin-6-yl]-acetamide;
rac-2-Cyclopropyl-N-[2-(5-fluoro-indan-1-ylamino)-quinolin-6-yl]-acetamide.

49. The compound of claim 1, selected from the group consisting of
rac-N-[2-(7-Fluoro-indan-1-ylamino)-quinolin-6-yl]-2-(4-methyl-piperazin-1-yl)-acetamide;
rac-Cyclopropanecarboxylic acid [2-(7-fluoro-indan-1-ylamino)-quinolin-6-yl]-amide;
$N^2$—(R)-Indan-1-yl-N6-morpholin-4-yl-quinoline-2,6-diamine;
$N^2$—(R)-Indan-1-yl-N6-(4-methyl-piperazin-1-yl)-quinoline-2,6-diamine;
(R)-Indan-1-yl-[6-(4-methyl-piperazin-1-yl)-quinolin-2-yl]-amine;
N-[2-((R)-Indan-1-ylamino)-quinolin-6-yl]-N',N''-diisopropyl-guanidine;
[2-((R)-Indan-1-ylamino)-quinolin-6-yl]-carbamic acid 1-methyl-piperidin-4-yl ester;
1-[2-((R)-Indan-1-ylamino)-quinolin-6-yl]-3-((3-exo)-9-isopropyl-9-aza-bicyclo[3.3.1]non-3-yl)-urea;
1-((3-exo)-8-Cyclopropyl-8-aza-bicyclo[3.2.1]oct-3-yl)-3-[2-((R)-indan-1-ylamino)-quinolin-6-yl]-1-methyl-urea; and
1-[2-((R)-Indan-1-ylamino)-quinolin-6-yl]-3-((3-exo)-8-isopropyl-8-aza-bicyclo[3.2.1]oct-3-yl)-urea.

50. The compound of claim 1, selected from the group consisting of
[2-((R)-Indan-1-ylamino)-quinolin-6-yl]-carbamic acid methyl ester;
rac-$N^2$-(7-Methoxy-indan-1-yl)-quinoline-2,6-diamine;
rac-$N^2$-(4-Methoxy-2,3-dihydro-benzofuran-3-yl)-quinoline-2,6-diamine;
rac-$N^2$-[4-(2-Methoxy-ethoxy)-2,3-dihydro-benzofuran-3-yl]-quinoline-2,6-diamine;
rac-$N^2$-(4-Ethoxy-2,3-dihydro-benzofuran-3-yl)-quinoline-2,6-diamine;
3-[2-((R)-Indan-1-ylamino)-quinolin-6-yl]-1-(1-isopropyl-piperidin-4-yl)-1-methyl-urea;
3-[2-((R)-Indan-1-ylamino)-quinolin-6-yl]-1-methyl-1-((3-exo)-8-methyl-8-aza-bicyclo[3.2.1]oct-3-yl)-urea;
1-[2-((R)-Indan-1-ylamino)-quinolin-6-yl]-3-((7-exo)-9-isopropyl-3-oxa-9-aza-bicyclo[3.3.1]non-7-yl)-urea;
rac-1-(1-Isopropyl-piperidin-4-yl)-3-[2-(7-methoxy-indan-1-ylamino)-quinolin-6-yl]-1-methyl-urea;
rac-1-(1-Isopropyl-piperidin-4-yl)-3-[2-(4-methoxy-2,3-dihydro-benzofuran-3-ylamino)-quinolin-6-yl]-urea; and
rac-1-[2-(4-Ethoxy-2,3-dihydro-benzofuran-3-ylamino)-quinolin-6-yl]-3-(1-isopropyl-piperidin-4-yl)-urea.

51. The compound of claim 1, selected from the group consisting of
rac-1-(1-Isopropyl-piperidin-4-yl)-3-{2-[4-(2-methoxy-ethoxy)-2,3-dihydro-benzofuran-3-ylamino]-quinolin-6-yl}-urea;
rac-N-[2-(4-Methoxy-2,3-dihydro-benzofuran-3-ylamino)-quinolin-6-yl]-2-(4-methyl-piperazin-1-yl)-acetamide;
rac-N-[2-(4-Ethoxy-2,3-dihydro-benzofuran-3-ylamino)-quinolin-6-yl]-2-(4-methyl-piperazin-1-yl)-acetamide;
rac-N-{2-[4-(2-Methoxy-ethoxy)-2,3-dihydro-benzofuran-3-ylamino]-quinolin-6-yl}-2-(4-methyl-piperazin-1-yl)-acetamide;
rac-1-((3-exo)-8-Isopropyl-8-aza-bicyclo[3.2.1]oct-3-yl)-3-[2-(7-methoxy-indan-1-ylamino)-quinolin-6-yl]-urea;
rac-3-[2-(5-Fluoro-indan-1-ylamino)-quinolin-6-yl]-1-(1-isopropyl-piperidin-4-yl)-1-methyl-urea;
rac-1-((3-exo)-8-Isopropyl-8-aza-bicyclo[3.2.1]oct-3-yl)-3-[2-(7-methoxy-indan-1-ylamino)-quinolin-6-yl]-1-methyl-urea;
rac-1-[1-(2-Hydroxy-ethyl)-piperidin-4-yl]-3-[2-(7-methoxy-indan-1-ylamino)-quinolin-6-yl]-urea;
rac-Cyclopropanecarboxylic acid [2-(6-fluoro-indan-1-ylamino)-quinolin-6-yl]-amide;

rac-1-[1-(2-Hydroxy-2-methyl-propyl)-piperidin-4-yl]-3-[2-(7-methoxy-indan-1-ylamino)-quinolin-6-yl]-1-methyl-urea; and
1-[1-(2-Hydroxy-2-methyl-propyl)-piperidin-4-yl]-3-[2-((R)-indan-1-ylamino)-quinolin-6-yl]-1-methyl-urea.

52. The compound of claim 1, selected from the group consisting of
rac-1-(1-Isopropyl-piperidin-4-yl)-3-[2-(4-methoxy-2,3-dihydro-benzofuran-3-ylamino)-quinolin-6-yl]-1-methyl-urea;
rac-1-((3-exo)-8-Isopropyl-8-aza-bicyclo[3.2.1]oct-3-yl)-3-[2-(4-methoxy-2,3-dihydro-benzofuran-3-ylamino)-quinolin-6-yl]-1-methyl-urea;
rac-Cyclopropanecarboxylic acid [2-(4-methoxy-2,3-dihydro-benzofuran-3-ylamino)-quinolin-6-yl]-amide;
N-[2-((R)-Indan-1-ylamino)-quinolin-6-yl]-acetamide;
rac-1-[2-(5-Fluoro-indan-1-ylamino)-quinolin-6-yl]-3-[1-(2-hydroxy-ethyl)-piperidin-4-yl]-urea;
(−)-N-[2-((S)-4-Methoxy-2,3-dihydro-benzofuran-3-ylamino)-quinolin-6-yl]-2-(4-methyl-piperazin-1-yl)-acetamide;
rac-1-[1-(2-Hydroxy-2-methyl-propyl)-piperidin-4-yl]-3-[2-(4-methoxy-2,3-dihydro-benzofuran-3-ylamino)-quinolin-6-yl]-1-methyl-urea;
rac-N-2-(6-Fluoro-2,3-dihydro-benzofuran-3-yl)-quinoline-2,6-diamine;
rac-N-[2-(7-Fluoro-indan-1-ylamino)-quinolin-6-yl]-2-methoxy-acetamide;
rac-3-[2-(6-Fluoro-2,3-dihydro-benzofuran-3-ylamino)-quinolin-6-yl]-1-(1-isopropyl-piperidin-4-yl)-1-methyl-urea; and
rac-N-[2-(6-Fluoro-2,3-dihydro-benzofuran-3-ylamino)-quinolin-6-yl]-2-(4-methyl-piperazin-1-yl)-acetamide.

53. The compound of claim 1, selected from the group consisting of
(−)-1-(1-Isopropyl-piperidin-4-yl)-3-[2-(4-methoxy-2,3-dihydro-benzofuran-3-ylamino)-quinolin-6-yl]-1-methyl-urea;
1-[1-(2-Hydroxy-ethyl)-piperidin-4-yl]-3-[2-((R)-indan-1-ylamino)-quinolin-6-yl]-1-methyl-urea;
rac-1-[1-(2-Hydroxy-ethyl)-piperidin-4-yl]-3-[2-(7-methoxy-indan-1-ylamino)-quinolin-6-yl]-1-methyl-urea;
rac-1-[1-(2-Hydroxy-ethyl)-piperidin-4-yl]-3-[2-(4-methoxy-2,3-dihydro-benzofuran-3-ylamino)-quinolin-6-yl]-1-methyl-urea;
rac-3-[2-(5-Fluoro-indan-1-ylamino)-quinolin-6-yl]-1-[1-(2-hydroxy-ethyl)-piperidin-4-yl]-1-methyl-urea;
rac-3-[2-(6-Fluoro-2,3-dihydro-benzofuran-3-ylamino)-quinolin-6-yl]-1-[1-(2-hydroxy-ethyl)-piperidin-4-yl]-1-methyl-urea;
N-[2-((R)-Indan-1-ylamino)-quinolin-6-yl]-2-(4-methyl-piperazin-1-yl)-acetamide;
N-[2-((R)-Indan-1-ylamino)-quinolin-6-yl]-2,2-dimethylpropionamide;
rac-N-[2-(7-Methoxy-indan-1-ylamino)-quinolin-6-yl]-2-morpholin-4-yl-acetamide;
rac-2-(2-Dimethylamino-ethylamino)-N-[2-(7-methoxy-indan-1-ylamino)-quinolin-6-yl]-acetamide; and
rac-2-(4-Cyclopropyl-piperazin-1-yl)-N-[2-(7-methoxy-indan-1-ylamino)-quinolin-6-yl]-acetamide.

54. A pharmaceutical composition comprising a therapeutically effective amount of a compound of formula (I)

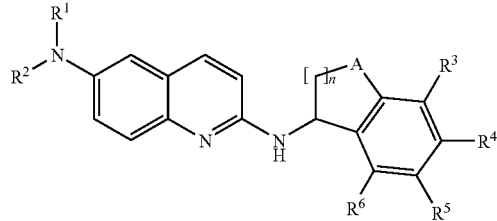

wherein
A is —CH$_2$— or —O—;
R$^1$ is hydrogen or alkyl;
R$^2$ is hydrogen,
heterocycloalkyl,
—(CH$_2$)$_a$—R$^a$, wherein R$^a$ is hydrogen, alkoxy, hydroxy, cyano, or NR$^i$R$^{ii}$, wherein R$^i$ and R$^{ii}$ are each independently hydrogen, alkyl or C(O)O-alkyl,
allyl,
—C(NH)—S—R$^b$, wherein R$^b$ is alkyl, cycloalkyl, haloalkyl, hydroxyalkyl, cyanoalkyl, or alkenyl,
—C(NR$^c$)NR$^d$R$^e$, wherein R$^c$, R$^d$, and R$^e$ are each independently hydrogen, alkyl, cycloalkyl, heterocycloalkyl, or wherein R$^d$ and R$^e$ together with the nitrogen to which they are bound form a heterocycloalkyl,
—C(O)R$^f$, wherein R$^f$ is alkyl, —(CH$_2$)$_b$-cycloalkyl, —(CH$_2$)$_b$—Oalkyl, —(CH$_2$)$_b$-heterocycloalkyl, —O-heterocycloalkyl, or —(CH$_2$)$_b$—NR$^{iii}$R$^{iv}$,
wherein R$^{iii}$ and R$^{iv}$ are each independently hydrogen, alkyl, —C(O)Oalkyl, —(CH$_2$)$_b$-cycloalkyl, —(CH$_2$)$_a$—Oalkyl, bicyclic cycloalkyl, bicyclic cycloalkenyl, —(CH$_2$)$_b$-heterocycloalkyl, —(CH$_2$)$_a$—O-heterocycloalkyl, or
—(CH$_2$)$_a$—NR'R", wherein R' and R" are each independently hydrogen, alkyl or cycloalkyl,
—C(S)NR'R$^{vi}$, wherein R$^v$ and R$^{vi}$ are each independently H, alkyl or cycloalkyl,
—S(O)$_2$NR$^{vii}$R$^{viii}$, wherein R$^{vii}$ and R$^{viii}$ are each independently H, alkyl, —C(O)Oalkyl, alkylene-O alkyl, cycloalkyl, or heterocycloalkyl, or
—S(O)$_2$-heterocycloalkyl, or
R$^1$ and R$^2$ together with the N atom to which they are bound form a 5- or 6-membered heterocycloalkyl;
R$^3$, R$^4$, R$^5$ and R$^6$ are each independently selected from the group consisting of H, halo, alkyl, haloalkyl, hydroxyalkyl, cyanoalkyl, alkoxy, haloalkoxy, —O-alkylene-O-alkyl, hydroxyl, oxo, cyano, nitro and NR$^{ix}$R$^x$,
wherein R$^{ix}$ and R$^x$ are each independently H or alkyl;
a is 1 to 6;
b is 0 to 6; and
n is 1 or 2, and wherein
heterocycloalkyl is unsubstituted or substituted with one or more substituents independently selected from the group consisting of alkyl, hydroxy, hydroxyalkyl, benzyl, oxo, —C(O)Oalkyl, cycloalkyl, alkylene-O-alkyl, —C(O)haloalkyl, cyanoalkyl, alkylene-S(O)$_2$-alkyl, -alkylene-C(O)N(alkyl)$_2$, halo, haloalkyl and alkyoxy; and wherein
cycloalkyl is unsubstituted or substituted with one or more substituents independently selected from the group consisting of alkyl, hydroxy, hydroxyalkyl, phenyl, oxo, cyanoalkyl, -alkylene-C(O)N(alkyl)$_2$, hydroxyalkyl, haloalkyl, halo, and alkyoxy;
or a pharmaceutically acceptable salt thereof and a pharmaceutically acceptable carrier.

* * * * *